(12) United States Patent
Shimoyama et al.

(10) Patent No.: US 10,234,429 B2
(45) Date of Patent: Mar. 19, 2019

(54) SENSOR

(71) Applicants: THE UNIVERSITY OF TOKYO, Tokyo (JP); KABUSHIKI KAISHA TOSHIBA, Tokyo (JP)

(72) Inventors: Isao Shimoyama, Tokyo (JP); Kiyoshi Matsumoto, Tokyo (JP); Binh Khiem Nguyen, Tokyo (JP); Hidetoshi Takahashi, Tokyo (JP); Minh Dung Nguyen, Tokyo (JP); Hiroto Tamura, Tokyo (JP); Quang Khang Pham, Tokyo (JP); Takahiro Omori, Kanagawa (JP); Osamu Nishimura, Kanagawa (JP); Akihiro Kasahara, Kanagawa (JP)

(73) Assignees: Kabushiki Kaisha Toshiba, Tokyo (JP); The University of Tokyo, Tokyo (JP)

( * ) Notice: Subject to any disclaimer, the term of this patent is extended or adjusted under 35 U.S.C. 154(b) by 287 days.

(21) Appl. No.: 15/217,436

(22) Filed: Jul. 22, 2016

(65) Prior Publication Data

US 2016/0327523 A1 Nov. 10, 2016

Related U.S. Application Data

(63) Continuation of application No. PCT/JP2015/051407, filed on Jan. 20, 2015.

(30) Foreign Application Priority Data

Jan. 24, 2014 (JP) ................................ 2014-011851

(51) Int. Cl.
*G01N 29/14* (2006.01)
*G01H 3/00* (2006.01)
(Continued)

(52) U.S. Cl.
CPC ............... *G01N 29/14* (2013.01); *G01H 3/00* (2013.01); *G01H 11/08* (2013.01); *G01H 17/00* (2013.01);
(Continued)

(58) Field of Classification Search
CPC ............... G01N 29/14; G01N 29/2406; G01N 29/2437; G01H 3/00; G01H 11/08;
(Continued)

(56) References Cited

U.S. PATENT DOCUMENTS 5,313,025 A * 5/1994 Roessler ................ G01V 1/135
175/1
6,366,675 B1 4/2002 Toda
(Continued)

FOREIGN PATENT DOCUMENTS

| JP | 9-264879 | 10/1997 |
| JP | 2000-329612 | 11/2000 |

(Continued)

OTHER PUBLICATIONS

International Search Report issued by the Japanese Patent Office in International Application No. PCT/JP2015/051407, dated Apr. 21, 2015 (2 pages).
(Continued)

*Primary Examiner* — Justin Seo
*Assistant Examiner* — Rose M Miller
(74) *Attorney, Agent, or Firm* — Finnegan, Henderson, Farabow, Garrett & Dunner, L.L.P.

(57) ABSTRACT

According to embodiments, a sensor includes a structure body, a container, a liquid and a sensing unit. The structure body includes a supporter, and a film unit. The film unit includes a first region. The first region includes a first end portion supported by the supporter, and a first portion being displaceable. The film unit includes an opening. The con-
(Continued)

tainer is connected to the structure body. A first space is defined between the film unit and the container. The liquid is provided inside the first space. The sensing unit senses a displacement of the first portion accompanying a displacement of the liquid.

20 Claims, 35 Drawing Sheets

(51) Int. Cl.
    *H04R 23/02* (2006.01)
    *G01H 11/08* (2006.01)
    *G01H 17/00* (2006.01)
    *G01N 29/24* (2006.01)
    *H04R 17/02* (2006.01)
    *H04R 7/06* (2006.01)

(52) U.S. Cl.
    CPC ..... *G01N 29/2406* (2013.01); *G01N 29/2437* (2013.01); *H04R 17/025* (2013.01); *H04R 23/02* (2013.01); *H04R 7/06* (2013.01); *H04R 2201/003* (2013.01); *H04R 2410/00* (2013.01)

(58) Field of Classification Search
    CPC ...... G01H 17/00; H04R 17/025; H04R 23/02; H04R 7/06; H04R 2201/003; H04R 2410/00
    USPC .......... 73/587, 632; 310/322, 324, 334, 336, 310/367, 369
    See application file for complete search history.

(56) References Cited

U.S. PATENT DOCUMENTS

| | | |
|---|---|---|
| 2006/0060003 A1 | 3/2006 | Thaysen |
| 2007/0230721 A1* | 10/2007 | White .................. H04R 19/005 381/166 |
| 2012/0160030 A1* | 6/2012 | Pearce .................. B06B 1/0688 73/753 |
| 2014/0000378 A1 | 1/2014 | Shimoyama et al. |
| 2015/0078934 A1* | 3/2015 | Lucas ................. F04B 43/0054 417/413.1 |
| 2015/0096388 A1 | 4/2015 | Shimoyama et al. |
| 2015/0362394 A1 | 12/2015 | Shimoyama et al. |

FOREIGN PATENT DOCUMENTS

| | | |
|---|---|---|
| JP | 2006-512589 | 4/2005 |
| JP | 2012-150074 | 8/2012 |
| JP | 2013-234853 | 11/2013 |
| JP | 2014-142323 | 8/2014 |
| WO | WO 2012/102073 A1 | 8/2012 |
| WO | WO 2015/111581 A1 | 7/2015 |

OTHER PUBLICATIONS

Written Opinion of the International Searching Authority dated Apr. 21, 2015, issued by the Japanese Patent Office in the counterpart International Application No. PCT/JP2015/051407; 5 pages.

* cited by examiner

FIG. 3A
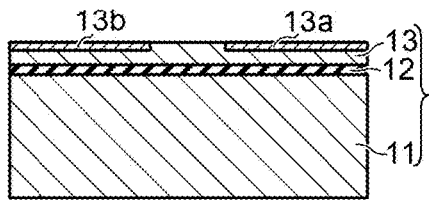
FIG. 3E
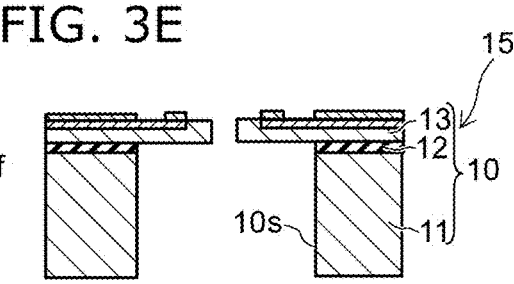
FIG. 3B
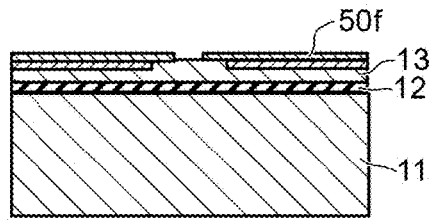
FIG. 3F
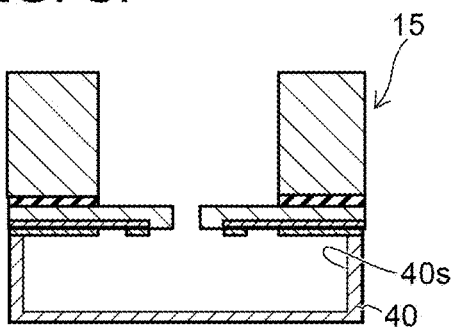
FIG. 3C
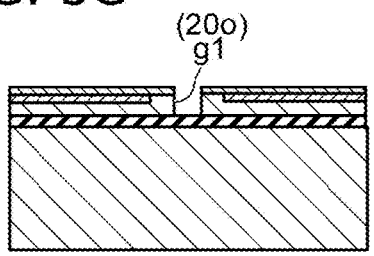
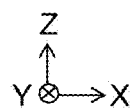
FIG. 3D
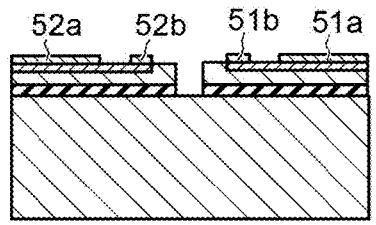

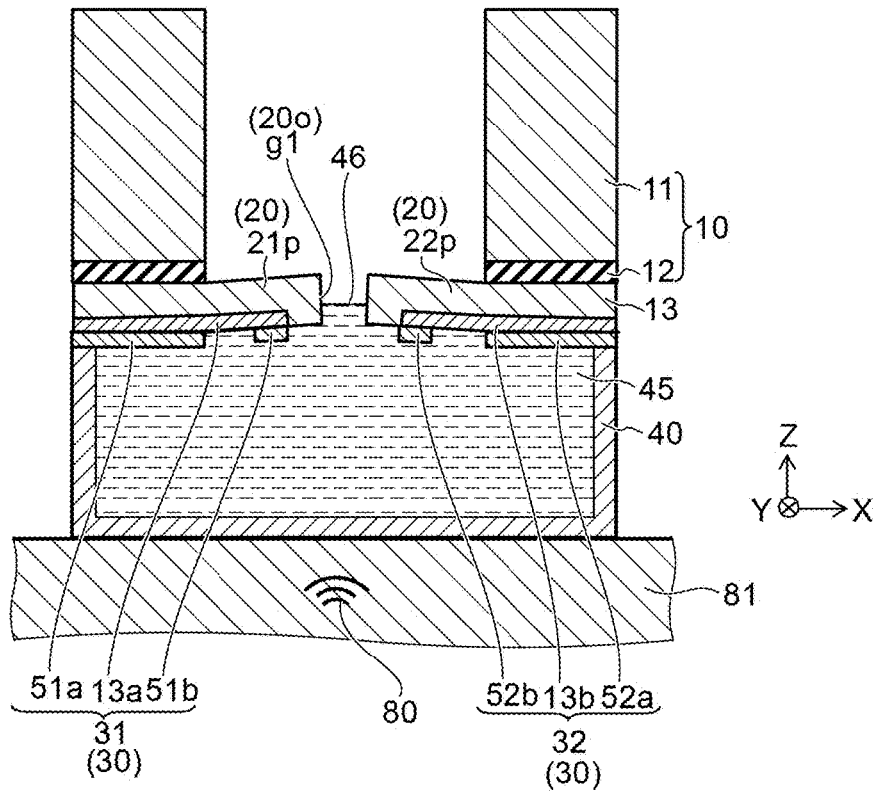
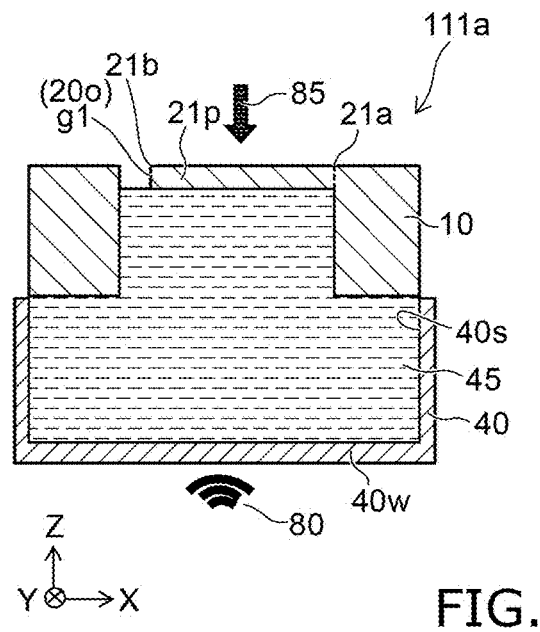
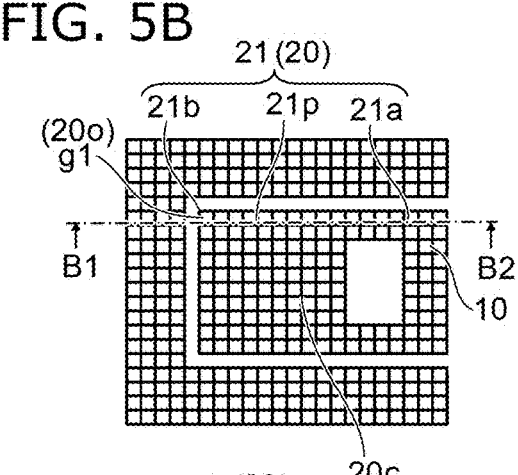
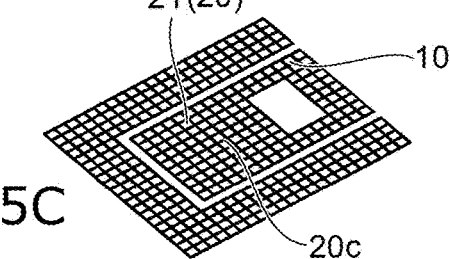

50.7kHz

300kHz

FIG. 35A
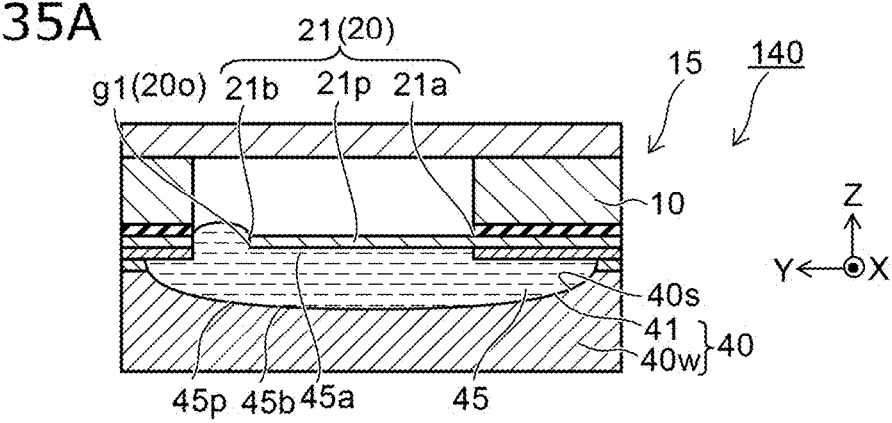
FIG. 35B
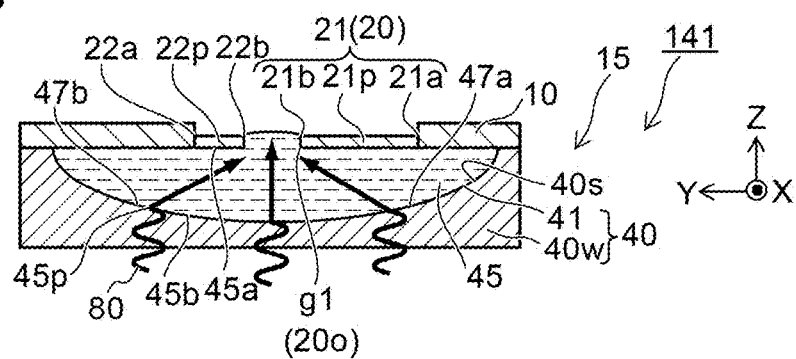
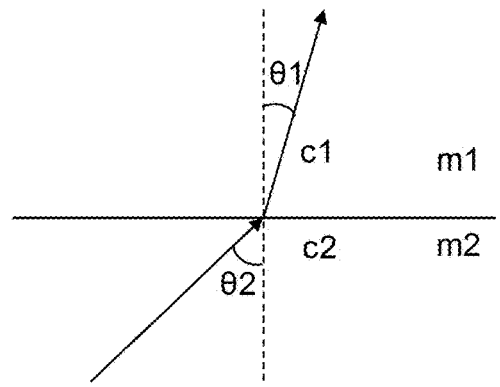
FIG. 36

FIG. 41
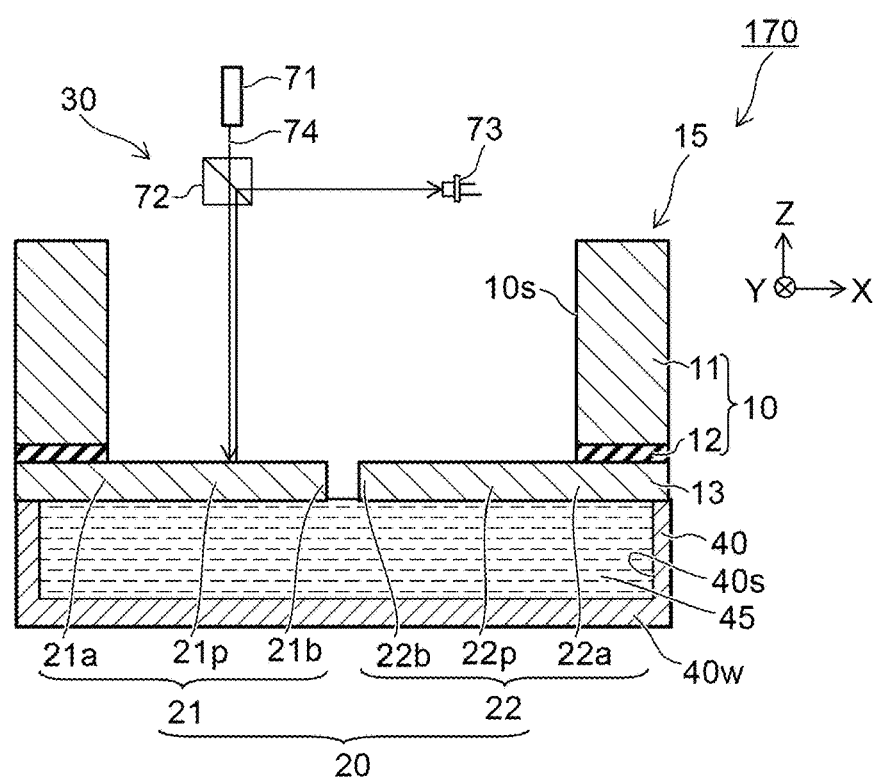
FIG. 42A
FIG. 42B
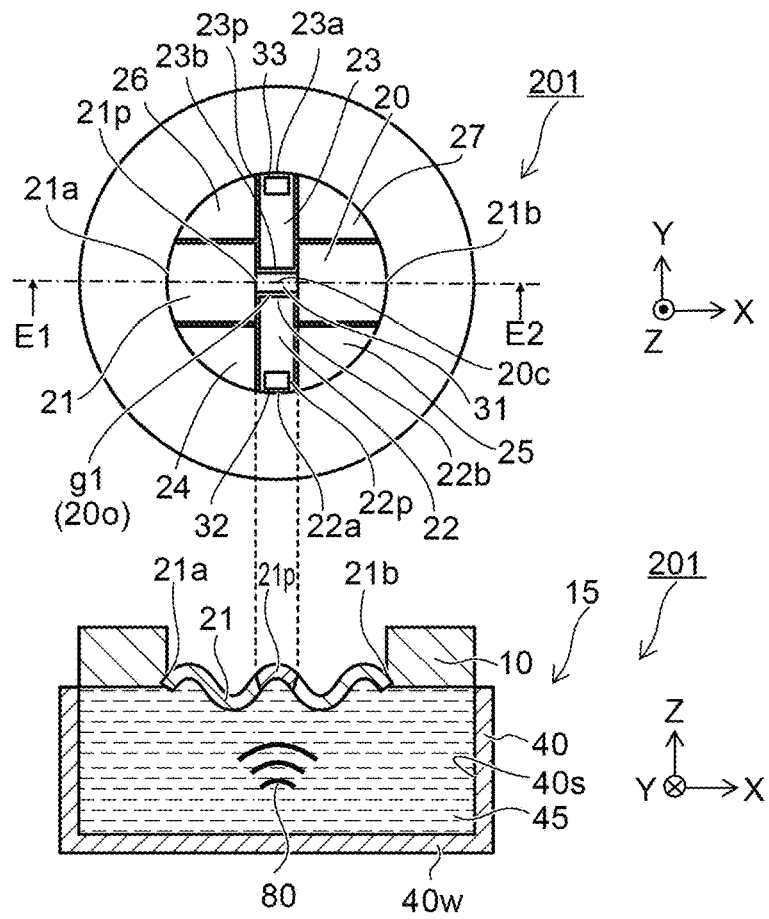

FIG. 44A
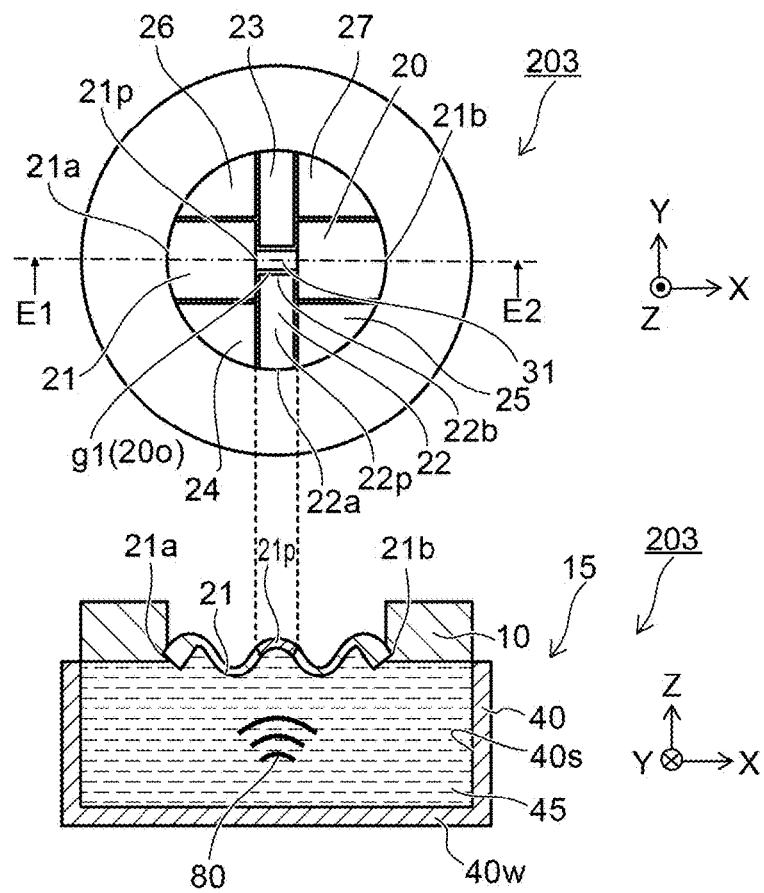
FIG. 44B
FIG. 44C
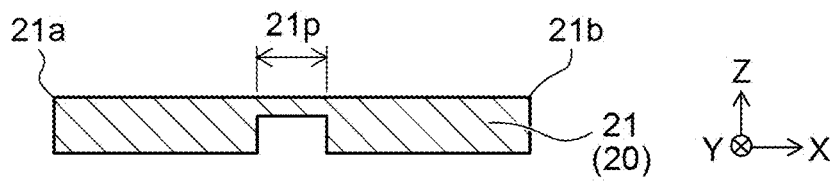
FIG. 44D
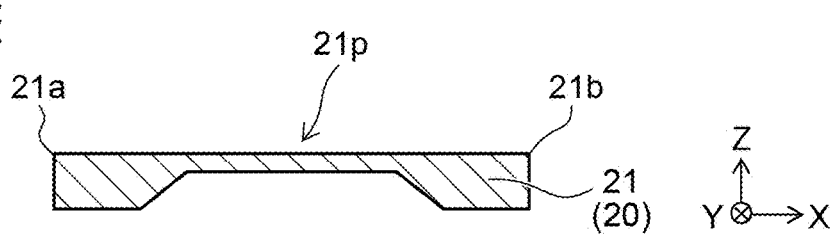
FIG. 44E

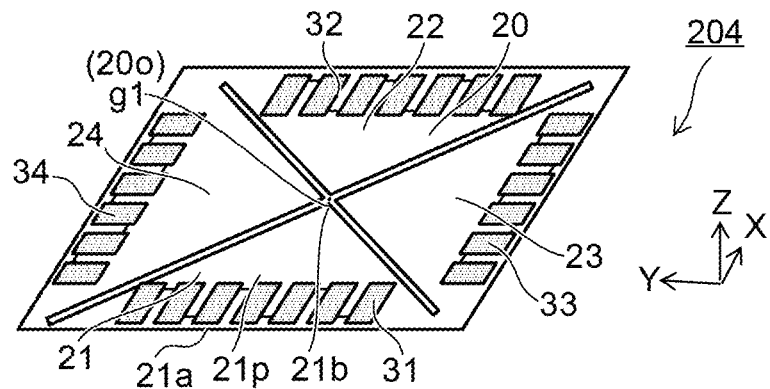
FIG. 45
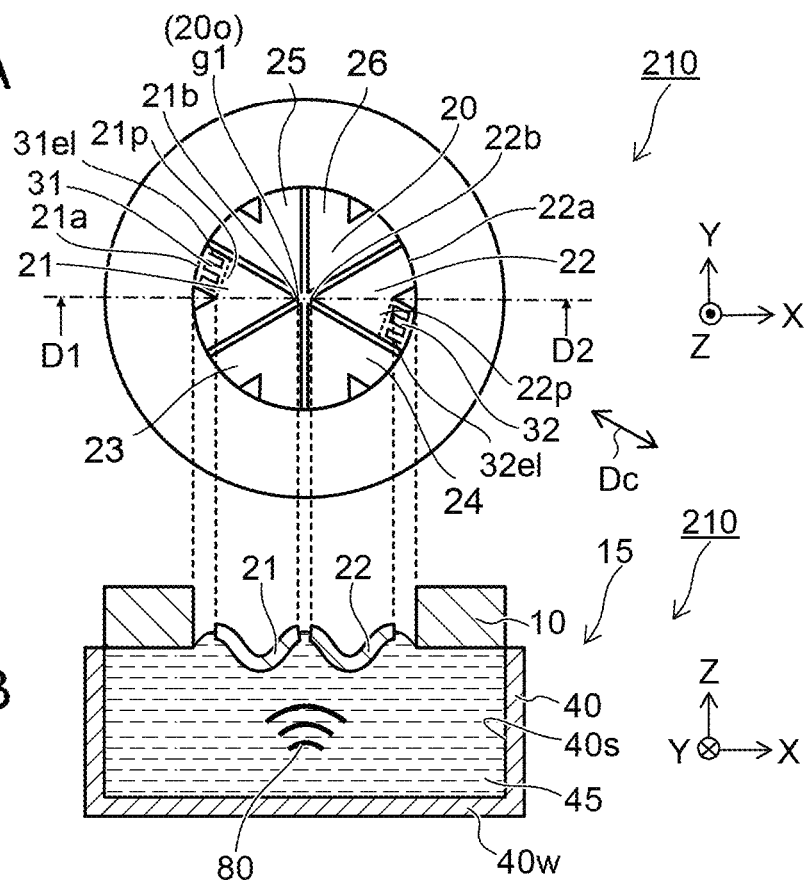
FIG. 46A
FIG. 46B

SENSOR

CROSS-REFERENCE TO RELATED APPLICATIONS

This is a continuation application of International Application PCT/JP2015/051407, filed on Jan. 20, 2015; the entire contents of which are incorporated herein by reference.

FIELD

Embodiments of the invention relate to a sensor.

BACKGROUND

For example, an AE (Acoustic Emission) sensor is a sensor that senses vibrations in the acoustic band and the ultrasonic band. AE is, for example, an elastic wave in the ultrasonic band occurring due to the occurrence and/or propagation of a crack. For example, the AE sensor is used in the sensed fatigue/degradation diagnosis, non-destructive testing, etc. It is desirable to the increase of the sensitivity of the sensor.

BRIEF DESCRIPTION OF THE DRAWINGS

FIG. 3A to FIG. 3F are schematic cross-sectional views in order of the processes, showing a method for manufacturing the sensor according to the first embodiment;

FIG. 4 is a schematic cross-sectional view showing an operation of the sensor according to the first embodiment;

FIG. 5A to FIG. 5C are schematic views showing another sensor according to the first embodiment;

FIG. 35A and FIG. 35B are schematic cross-sectional views showing sensors according to a second embodiment;

FIG. 36 is a schematic view showing a characteristic of the sensor according to the second embodiment;

FIG. 41 is a schematic cross-sectional view showing a sensor according to a fifth embodiment;

FIG. 42A and FIG. 42B are schematic views showing a sensor according to a sixth embodiment;

FIG. 44A to FIG. 44E are schematic views showing another sensor according to the sixth embodiment;

FIG. 45 is a schematic perspective view showing another sensor according to the sixth embodiment;

FIG. 46A and FIG. 46B are schematic views showing a sensor according to a seventh embodiment;

DETAILED DESCRIPTION

Figure 1A:
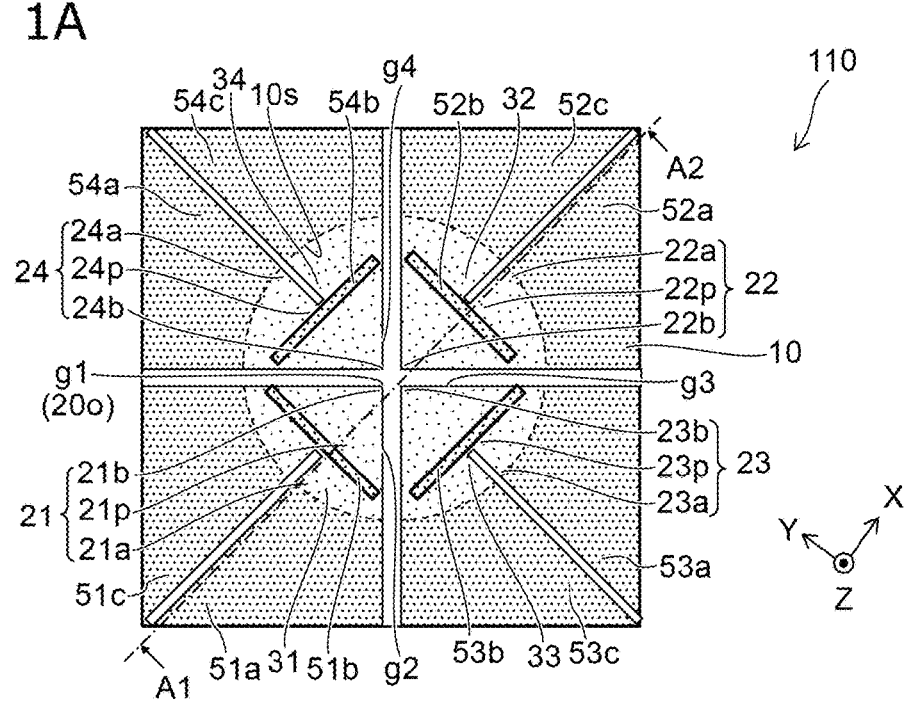
FIG. 1A and FIG. 1B are schematic views showing a sensor according to a first embodiment.

According to embodiments of the invention, a sensor includes a structure body, a container, a liquid and a sensing unit. The structure body includes a supporter, and a film unit. The film unit includes a first region. The first region includes a first end portion supported by the supporter, and a first portion being displaceable. The film unit includes an opening. The container is connected to the structure body. A first space is defined between the film unit and the container. The liquid is provided inside the first space. The sensing unit senses a displacement of the first portion accompanying a displacement of the liquid.

Various embodiments will be described hereinafter with reference to the accompanying drawings.

The drawings are schematic or conceptual. The size ratio between the portions is not necessarily identical to those in reality. Furthermore, the same portion may be shown with different dimensions or ratios in different figures.

In the present specification and drawings, the same elements as those described previously with reference to earlier figures are labeled with like reference numerals, and the detailed description thereof is omitted as appropriate.

First Embodiment

Figure 1B:
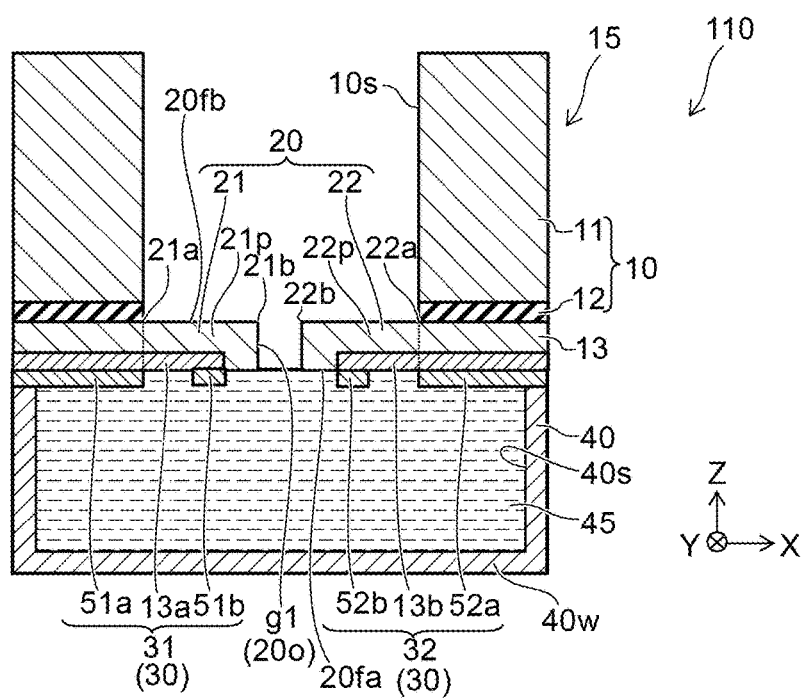

FIG. 1A and FIG. 1B are schematic views illustrating a sensor according to a first embodiment.

FIG. 1A is a schematic see-through plan view. FIG. 1B is a schematic cross-sectional view along line A1-A2 of FIG. 1A.

As shown in FIG. 1A and FIG. 1B, the sensor 110 according to the embodiment includes a structure body 15, a container 40, a liquid 45, and a sensing unit 30.

The structure body 15 includes a supporter 10 and a film unit 20.

The sensor 110 is, for example, an acoustic sensor. For example, the sensor 110 senses vibrations in the acoustic band and the ultrasonic band. For example, the sensor 110 senses AE. For example, AE is an elastic wave in the ultrasonic band occurring due to the occurrence and/or propagation of a crack. For example, the sensor 110 is used as a sensor that senses AE. For example, the sensor 110 is used in fatigue/degradation diagnosis that senses the occurrence of micro defects. For example, the sensor 110 is used in non-destructive testing, etc.

Figure 2A:
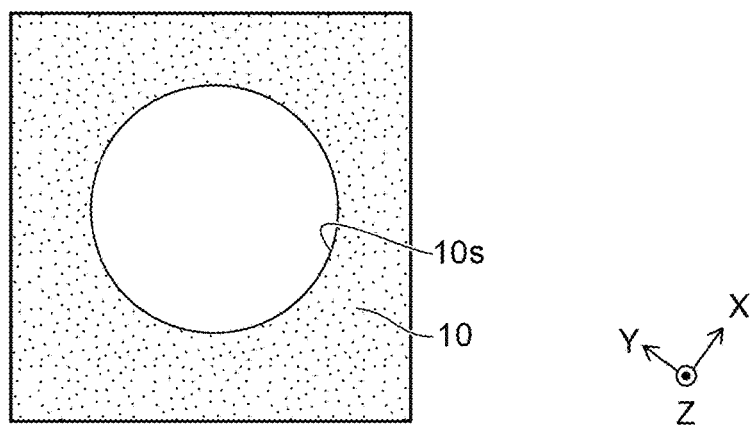
FIG. 2A to FIG. 2C are schematic plan views showing the sensor according to the first embodiment.
Figure 2B:
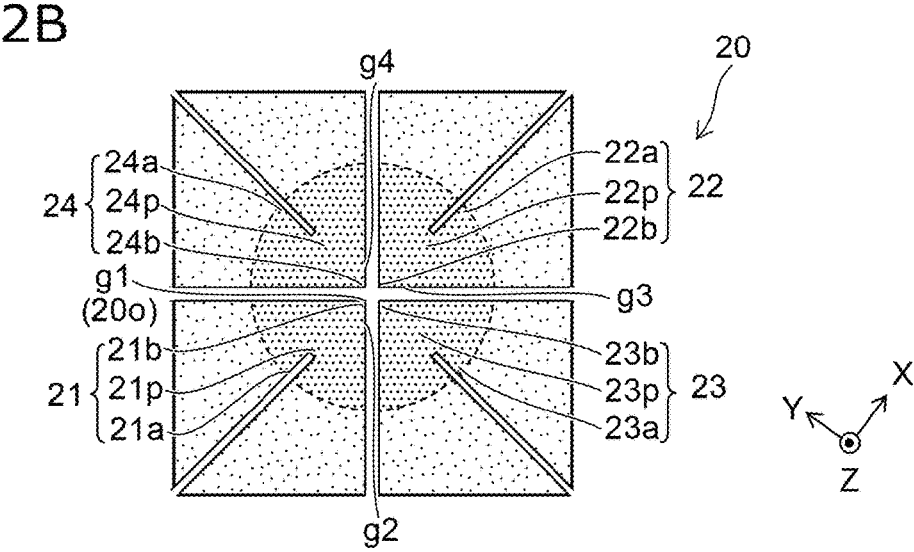
Figure 2C:
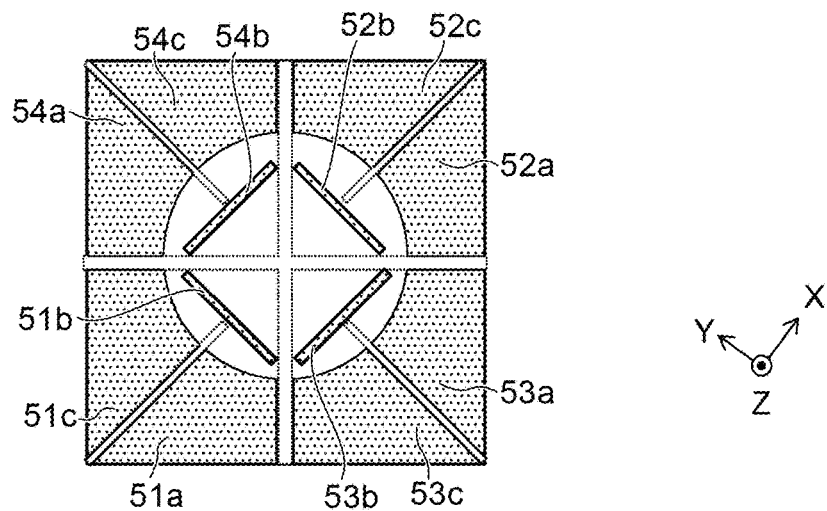

FIG. 2A to FIG. 2C are schematic plan views illustrating the sensor according to the first embodiment.

FIG. 2A shows the supporter 10. FIG. 2B shows the film unit 20. FIG. 2C shows electrodes described below.

The film unit 20 includes a first region 21. In the example, the film unit 20 further includes a second region 22, a third region 23, and a fourth region 24. The film unit 20 has an opening 20o.

The first region 21 includes a first end portion 21a, a first opposite end 21b, and a first portion 21p. The first end portion 21a is supported by the supporter 10. The first opposite end 21b is the end on the side opposite to the first end portion 21a. The first portion 21p is positioned between the first end portion 21a and the first opposite end 21b. As described below, the first portion 21p is displaceable. On the other hand, the first end portion 21a is a fixed end.

The second region 22 includes a second end portion 22a, a second opposite end 22b, and a second portion 22p. The second end portion 22a is supported by the supporter 10. The second opposite end 22b is the end on the side opposite to the second end portion 22a. The second portion 22p is positioned between the second end portion 22a and the second opposite end 22b. In the example, the second portion 22p is displaceable. The second end portion 22a is a fixed end.

The third region 23 includes a third end portion 23a, a third opposite end 23b, and a third portion 23p. The third end portion 23a is supported by the supporter 10. The third opposite end 23b is the end on the side opposite to the third end portion 23a. The third portion 23p is positioned between the third end portion 23a and the third opposite end 23b. In the example, the third portion is displaceable. The third end portion 23a is a fixed end.

The fourth region 24 includes a fourth end portion 24a, a fourth opposite end 24b, and a fourth portion 24p. The fourth end portion 24a is supported by the supporter 10. The fourth opposite end 24b is the end on the side opposite to the fourth end portion 24a. The fourth portion 24p is positioned between the fourth end portion 24a and the fourth opposite end 24b. In the example, the fourth portion 24p is displaceable. The fourth end portion 24a is a fixed end.

The first to fourth regions 21 to 24 each are, for example, cantilevers. As described below, for example, the film unit 20 may have the configuration of a two-end-supported beam or the configuration of a diaphragm.

In the example, a first gap g1 is provided between the first portion 21p and the second portion 22p. The first gap g1 is provided between the first opposite end 21b and the second opposite end 22b. The first gap g1 is used as the opening 20o.

For example, a second gap g2 (e.g., a slit) is provided between the first portion 21p and the third portion 23p. For example, a third gap g3 (e.g., a slit) is provided between the second portion 22p and the third portion 23p. For example, a fourth gap g4 (e.g., a slit) is provided between the second portion 22p and the fourth portion 24p. These gaps (slits) also are included in the opening 20o. By providing the gaps, for example, the first to fourth portions 21p to 24p are displaced easily.

The container 40 is connected to the structure body 15. The container 40 includes a wall 40w. The container 40 defines a first space 40s between the container 40 and the film unit 20. The film unit 20 has a first surface 20fa and a second surface 20fb. The first surface 20fa is the surface on the first space 40s side. The second surface 20fb is the surface on the side opposite to the first surface 20fa.

The liquid 45 is contained inside the first space 40s. For example, the liquid 45 contacts the first surface 20fa of the film unit 20. Because the opening 20o is provided in the film unit 20 as described above, one portion of the liquid 45 is exposed in the opening 20o. For example, in the case where the surface area of the opening 20o is small (the width is narrow), the liquid 45 substantially does not outflow from the opening 20o to the outside due to the surface tension of the liquid 45. One portion of the liquid 45 may contact the side surface of the film unit 20 in the opening 20o.

The sensing unit 30 senses the displacement of the first portion 21p. The displacement of the first portion 21p occurs with the displacement of the liquid 45. As described below, the displacement of the liquid 45 occurs based on a sound wave applied to the container 40. The sound wave is what is sensed by the sensor 110. For example, for a microphone, the frequency of the sound wave is not less than 10 Hz and not more than 20 kHz. For example, for an AE sensor, the frequency of the sound wave is not less than 10 kHz and not more than 3 MHz. For example, for an ultrasonic imaging apparatus, the frequency of the sound wave is 5 MHz or more.

In this specification, an acoustic sensor is taken to include applications in relatively low frequency bands and applications in the ultrasonic band. Also, in this specification, a sound wave includes any elastic wave propagating through any elastic body including gases, liquids, and solids. The acoustic sensor according to the embodiment includes, for example, an AE sensor of an application in the ultrasonic band. The acoustic sensor according to the embodiment may include, for example, a sensor for a relatively low frequency.

In the example, the sensing unit 30 further senses the displacement of the second portion 22p accompanying the displacement of the liquid 45, the displacement of the third portion 23p accompanying the displacement of the liquid 45, and the displacement of the fourth portion 24p accompanying the displacement of the liquid 45.

In the example, a cavity is provided in the supporter 10. In other words, the supporter 10 defines a second space 10s. Also, in the example, at least one portion of the first portion 21p is disposed between the second space 10s and the liquid 45. In the example, at least one portion of the second portion 22p, at least one portion of the third portion 23p, and at least one portion of the fourth portion 24p are further disposed between the second space 10s and the liquid 45.

In the example, for example, the supporter 10 and the film unit 20 are formed of an SOI (Silicon On Insulator) structure. In other words, the supporter 10 includes a base 11 and an insulating portion 12. The film unit 20 is formed from a thin film 13. The base 11 includes silicon. The insulating portion 12 includes silicon oxide. The thin film 13 includes silicon.

In the example, a piezoresistor is used as the sensing unit 30. In other words, an impurity is introduced to at least one portion of the thin film 13. An electrode is provided in the region where the impurity is introduced.

For example, the sensing unit 30 includes a first sensing element 31. The first sensing element 31 is provided at the first portion 21p of the first region 21.

In the example, the first sensing element 31 includes a crystal layer 13a of silicon, a first electrode 51a, and a second electrode 51b. The crystal layer 13a of silicon includes an impurity. The crystal layer 13a of silicon is, for example, monocrystalline silicon. One portion of the thin film 13 recited above is used as the crystal layer 13a of silicon.

In the example, the first sensing element 31 further includes a first counter electrode 51c. For example, a current is caused to flow in a path between the first electrode 51a and the second electrode 51b and between the second electrode 51b and the first counter electrode 51c. For example, stress is applied to the film unit 20; and the first portion 21p is displaced. Strain that accompanies the displacement occurs in the crystal layer 13a of silicon. Compressive strain or tensile strain occurs. The electrical resistance of the crystal layer 13a of silicon changes according to the strain. The displacement of the first portion 21p is sensed by sensing the change of the electrical resistance by causing the current to flow in the path recited above. In other words, the first sensing element 31 has a change of a resistance accompanying the displacement of the first portion 21p.

In the example, the sensing unit 30 includes second to fourth sensing elements 32 to 34. The second sensing element 32 is provided at the second portion 22p of the second region 22. A third sensing element 33 is provided at the third portion 23p of the third region 23. The fourth sensing element 34 is provided at the fourth portion 24p of the fourth region 24.

The second sensing element 32 includes, for example, a crystal layer 13b of silicon including an impurity, an electrode 52a, an electrode 52b, and an electrode 52c. The third sensing element 33 includes, for example, a crystal layer of silicon including an impurity (one portion of the thin film 13), an electrode 53a, an electrode 53b, and an electrode 53c. The fourth sensing element 34 includes, for example, a crystal layer of silicon including an impurity (one portion of the thin film 13), an electrode 54a, an electrode 54b, and an electrode 54c. Also, the second to fourth sensing elements 32 to 34 respectively sense the change of the electrical resistance accompanying the displacement for the second portion 22p to the fourth portion 24p.

As described below, the embodiment is not limited to the description recited above. The sensing elements (e.g., the first sensing element 31, etc.) may have at least one of the change of the resistance occurring with the displacement of the first portion 21p, the change of the voltage of the piezoelectricity occurring with the displacement of the first portion 21p, or the change of the electrostatic capacitance occurring with the displacement of the first portion 21p.

For example, a direction from the container 40 toward the supporter 10 is taken as a Z-axis direction (a first direction). One direction perpendicular to the Z-axis direction is taken as an X-axis direction. A direction perpendicular to the Z-axis direction and the X-axis direction is taken as a Y-axis direction.

For example, the film unit 20 substantially extends in the X-Y plane. In the example, the extension direction of the first region 21 of the film unit 20 is set to the X-axis direction. In other words, the direction from the first end portion 21a toward the first opposite end 21b is aligned with the X-axis direction. The direction from the first end portion 21a toward the first portion 21p is aligned with the X-axis direction.

FIG. 3A to FIG. 3F are schematic cross-sectional views in order of the processes, illustrating a method for manufacturing the sensor according to the first embodiment.

A SOI substrate 10f is prepared as shown in FIG. 3A. The SOI substrate 10f includes the base 11 (silicon), the insulating portion 12 (silicon oxide), and the thin film 13 (silicon). For example, the crystal layers 13a and 13b of silicon, etc., are formed by introducing an impurity into at least one portion of the thin film 13 (e.g., a silicon active layer). For example, thermal diffusion is used to introduce the impurity. For example, at least one of arsenic or phosphorus is used as the impurity. In such a case, an n-type semiconductor is obtained. Boron may be used as the impurity. In such a case, a p-type semiconductor is obtained.

As shown in FIG. 3B, an electrode film 50f that is used to form the electrodes is formed. For example, at least one of gold or aluminum is used as the electrode film 50f. The electrode film 50f is patterned into a prescribed configuration.

As shown in FIG. 3C, the thin film 13 (the silicon layer) is patterned using the patterned electrode film 50f as a mask. For example, ICP-RIE (Inductively Coupled Plasma Reactive Ion Etching) or the like is used in the patterning. Thereby, the opening 20o is made. The opening 20o includes gaps (the first gap g1, etc.), slits, etc. The widths of the slits are, for example, not less than 10 nm and not more than 100 µm.

The electrode film 50f is patterned as shown in FIG. 3D. Thereby, the electrodes (e.g., the first electrode 51a, the second electrode 51b, the electrode 52a, the electrode 52b, etc.) are formed.

As shown in FIG. 3E, one portion of the silicon used to form the base 11 is removed from the back surface of the SOI substrate 10f. For example, ICP-RIE is used in the removal. Further, one portion of the silicon oxide used to form the insulating portion 12 is removed. Thereby, the supporter 10 is formed. In other words, the second space 10s is made. The film unit 20 (the cantilever) is released from the support layer of silicon. Thereby, the second space 10s is made. The thin film 13 becomes the film unit 20. Thereby, the structure body 15 is formed.

The size (e.g., the length in the X-axis direction) of the film unit 20 is, for example, not less than 10 μm and not more than 1 mm. The thickness of the film unit 20 is, for example, not less than 50 nm and not more than 10 μm.

As shown in FIG. 3F, the container 40 and the structure body 15 are bonded. Thereby, the first space 40s is defined. The container 40 includes, for example, an organic material or an inorganic material. The container 40 may include, for example, silicone rubber. The container 40 may include, for example, PDMS (dimethylpolysiloxane). For example, a metal may be used as the container 40. For example, at least one of aluminum or iron (e.g., stainless steel) may be used as the container 40. In the embodiment, these materials are arbitrary.

The liquid 45 is filled into the first space 40s. Thereby, the sensor 110 is formed.

For example, silicone oil, water, or the like is used as the liquid 45. The thickness (e.g., the length in the Z-axis direction) of the liquid 45 is, for example, not less than 1 μm and not more than 10 mm.

FIG. 4 is a schematic cross-sectional view illustrating an operation of the sensor according to the first embodiment.

As shown in FIG. 4, the sensor 110 is mounted to a measurement object 81. The measurement object 81 is, for example, a building, etc. A sound wave 80 (e.g., a low frequency wave, an ultrasonic wave, etc., e.g., AE) is radiated from the measurement object 81. A surface wave 46 is formed in the front surface of the liquid 45 due to the sound wave 80. The film unit 20 is displaced according to the surface wave 46. Specifically, for example, the first to fourth portions 21p to 24p are displaced. The displacement is sensed by the sensing unit 30.

In the embodiment, the sound wave 80 can be sensed with high sensitivity by sensing the displacement of the film unit 20 (e.g., the first portion 21p, etc.) occurring due to the displacement of the liquid 45.

In the embodiment, the liquid 45 is contained inside the first space 40s defined by the container 40 and the film unit 20 in which the opening 20o is provided. For example, the portion of the liquid 45 contacting the container 40 is used as the fixed end of the liquid 45. A large displacement is obtained at the portion of the liquid 45 positioned at the opening 20o. Thereby, high sensitivity is obtained in the sensing of the sound wave 80.

In the sensor 110, in addition to the first portion 21p, the second to fourth portions 22p to 24p are provided in the film unit 20. A displacement occurs at these portions according to the displacement of the liquid 45. For example, highly-sensitive sensing becomes possible by sensing the displacements of these portions.

The thickness of the liquid 45 is sufficiently thicker than the thickness of the film unit 20. The thickness of the liquid 45 is, for example, not less than 5 times the thickness of the film unit 20. Thereby, the film unit 20 deforms along the deformation of the front surface of the liquid 45. Thereby, the displacement of the liquid 45 based on the sound wave 80 to be sensed is converted efficiently into the displacement of the first portion 21p. Thereby, highly-sensitive sensing becomes possible. The thickness of the liquid 45 may be, for example, not less than 10 times the thickness of the film unit 20. Further, the thickness may be 100 times or more.

For example, the thickness of the liquid 45 and the thickness of the wall 40w of the container 40 are selected appropriately by, for example, investigating the vibration characteristics beforehand by experiments and/or simulations. The waveform of the front surface of the liquid 45 is controlled appropriately. The thickness of the wall 40w is the thickness of the container 40 (the wall 40w) along a direction from the first space 40s inside the container 40 toward the space outside the container 40.

For example, an opening may be provided in the container 40 (the wall 40w); and the liquid 45 and the measurement object 81 may contact each other via the opening.

In the embodiment, for example, the cross section (the cross section cut by the X-Y plane) of the second space 10s is, for example, a circle. In such a case, for example, the surface wave 46 occurring at the front surface of the liquid 45 propagates from all of the end portions to the center without a phase difference. As a result, for example, high sensitivity is obtained.

For example, by downsizing the cross-sectional area of the second space 10s, the number of anti-nodes of the surface wave 46 occurring from the end portion to the center of the front surface of the liquid 45 decreases. Thereby, for example, the sensitivity of high frequency elastic waves improves.

A measurement example of characteristics of the sensor according to the embodiment will now be described.

FIG. 5A to FIG. 5C are schematic views illustrating another sensor according to the first embodiment.

FIG. 5A is a schematic cross-sectional view of the sensor 111a according to the embodiment. FIG. 5B is a schematic plan view showing the configuration of the film unit 20 of the sensor 111a. FIG. 5A is a line B1-B2 cross-sectional view of FIG. 5B. FIG. 5C is a schematic perspective view showing the configuration of the film unit 20.

In the sensor 111a as well, as shown in FIG. 5A to FIG. 5C, the opening 20o is provided in the film unit 20. In the example, the first region 21 is provided in the film unit 20. For example, the film unit 20 has a cantilever configuration.

As illustrated in FIG. 5A, the sound wave 80 is applied to the sensor 111a. The displacement of the film unit 20 at this time is sensed by a detector 85. In the example, a laser displacement detector is used as the detector 85. The sensing positions by the detector 85 are the intersections of the mesh shown in FIG. 5B and FIG. 5C. In the measurement results described below, the regions between the measurement points are interpolated and displayed as a surface.

The diameter (the maximum value of the width in the X-Y plane) of the second space 10s (the cavity) of the sensor 111a is 200 μm. The thickness of the liquid 45 is 3 mm. The thickness of the film unit 20 (the cantilever) is 300 nm. The thickness of the wall 40w of the container 40 is 500 μm. The film unit 20 includes silicon. The wall 40w includes PDMS. The liquid 45 includes silicone oil.

First, an example of the measurement results of the characteristics at a center position 20c of the film unit 20 will be described.

Figure 6A:
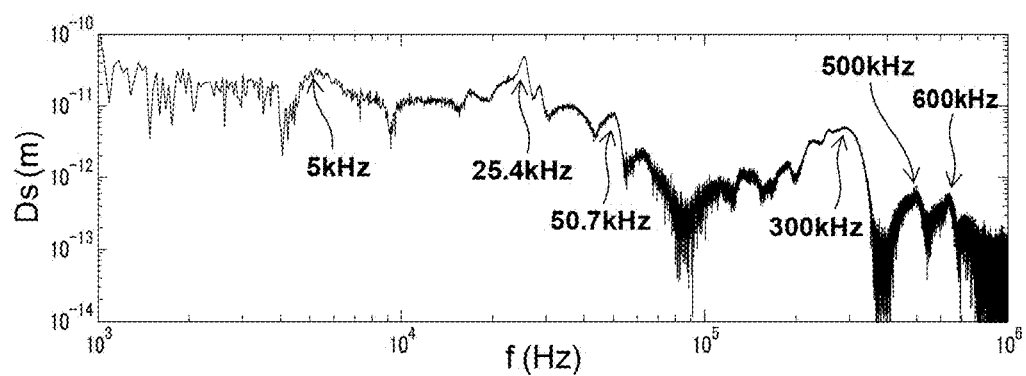
FIG. 6A and FIG. 6B are graphs showing characteristics of the other sensor according to the first embodiment.
Figure 6B:
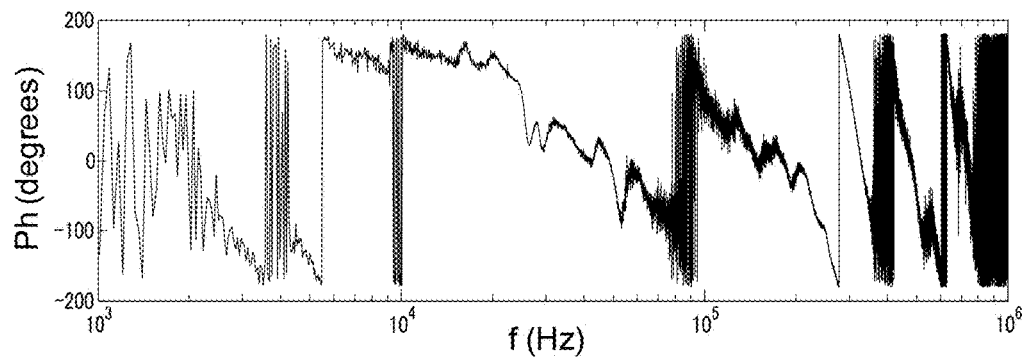
Figure 7:
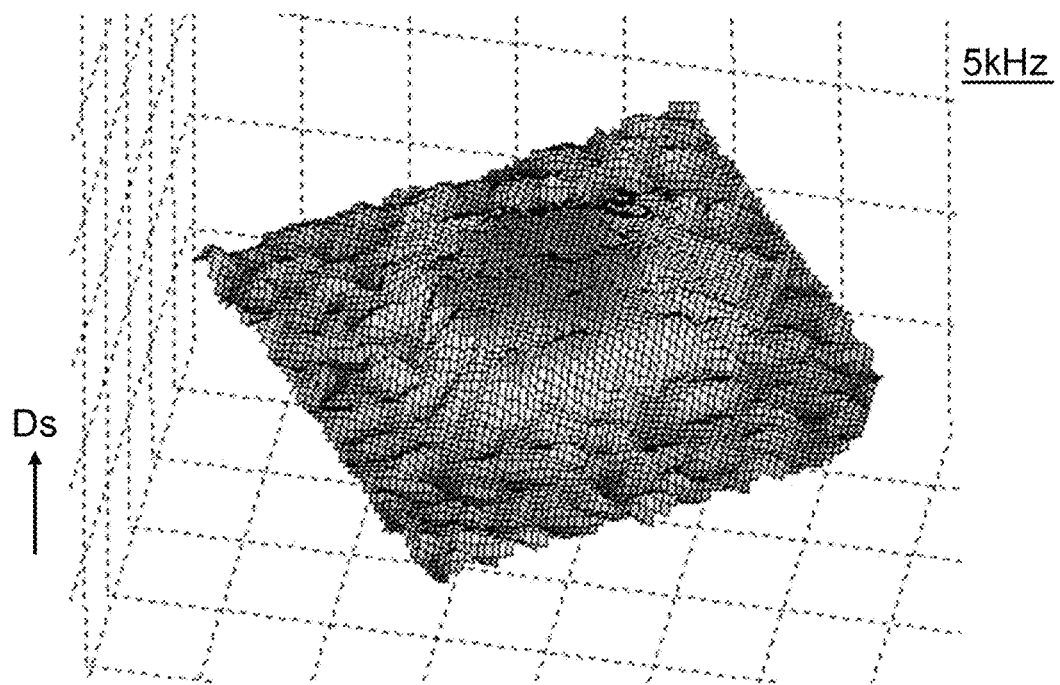
FIG. 7 is a schematic view showing the characteristics of the other sensor according to the first embodiment.
Figure 8:
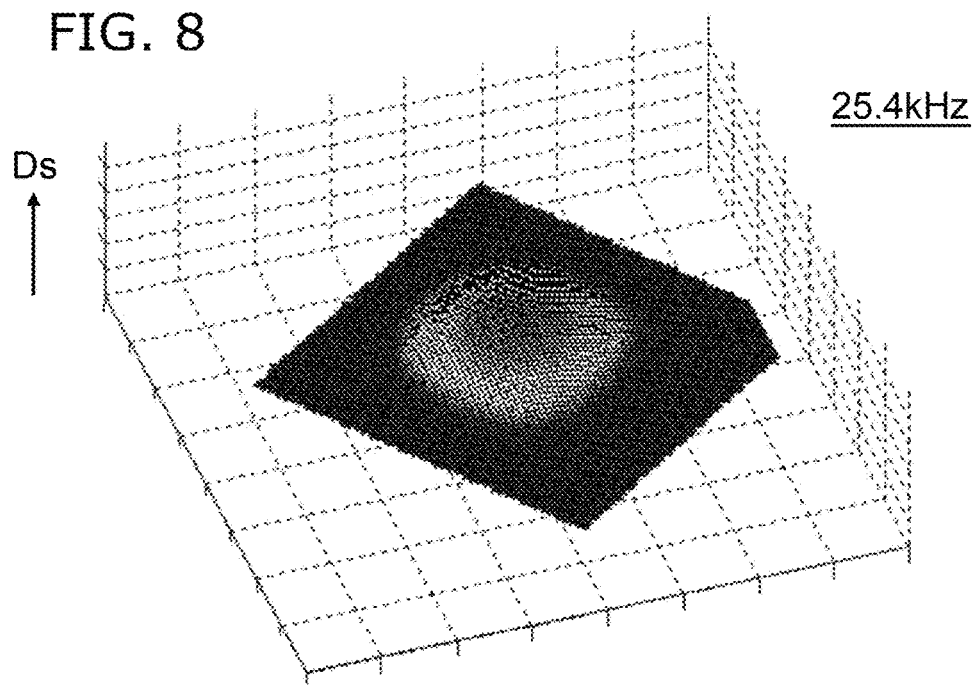
FIG. 8 is a schematic view showing the characteristics of the other sensor according to the first embodiment.
Figure 9:
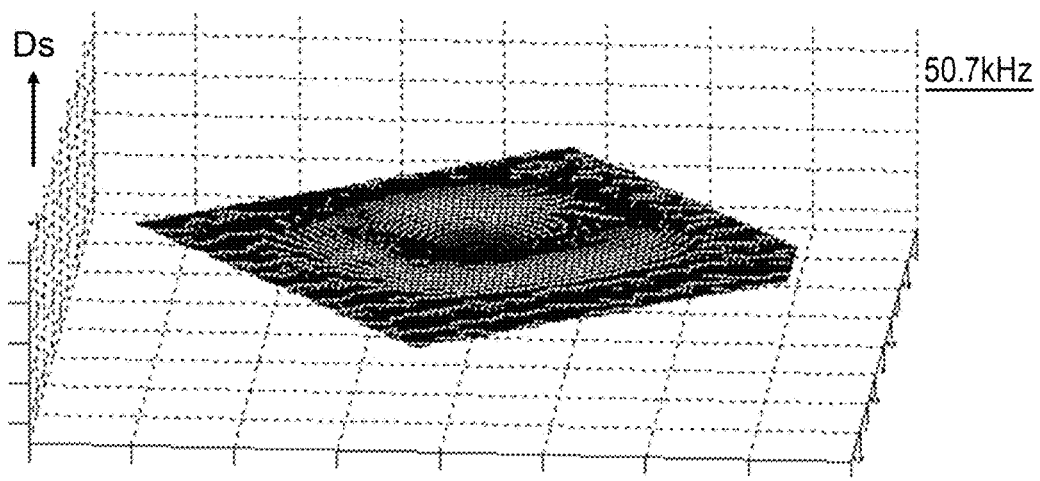
FIG. 9 is a schematic view showing the characteristics of the other sensor according to the first embodiment.
Figure 10:
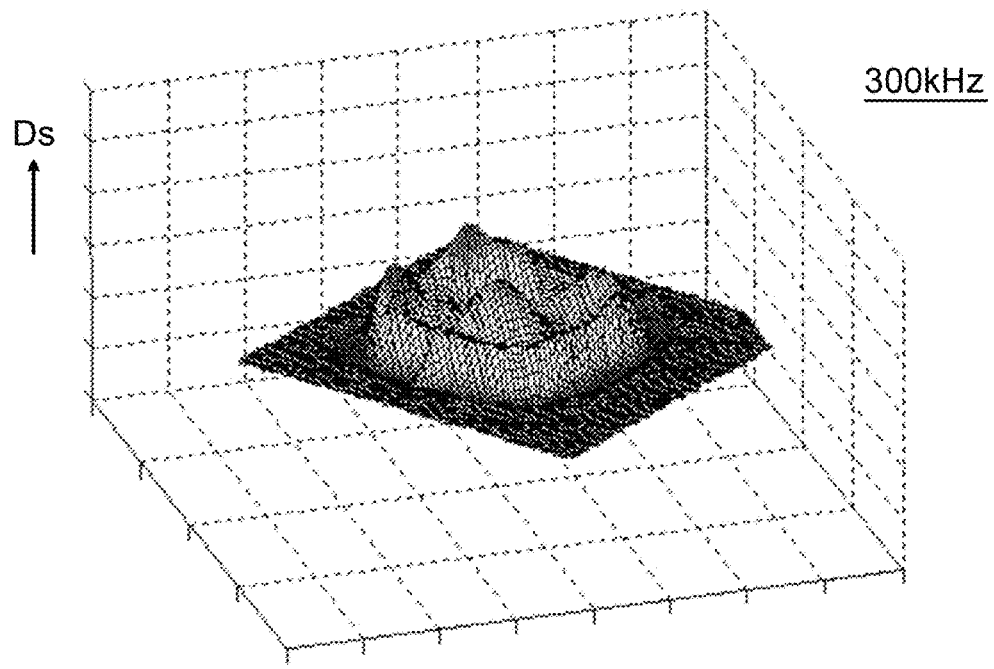
FIG. 10 is a schematic view showing the characteristics of the other sensor according to the first embodiment.
Figure 11:
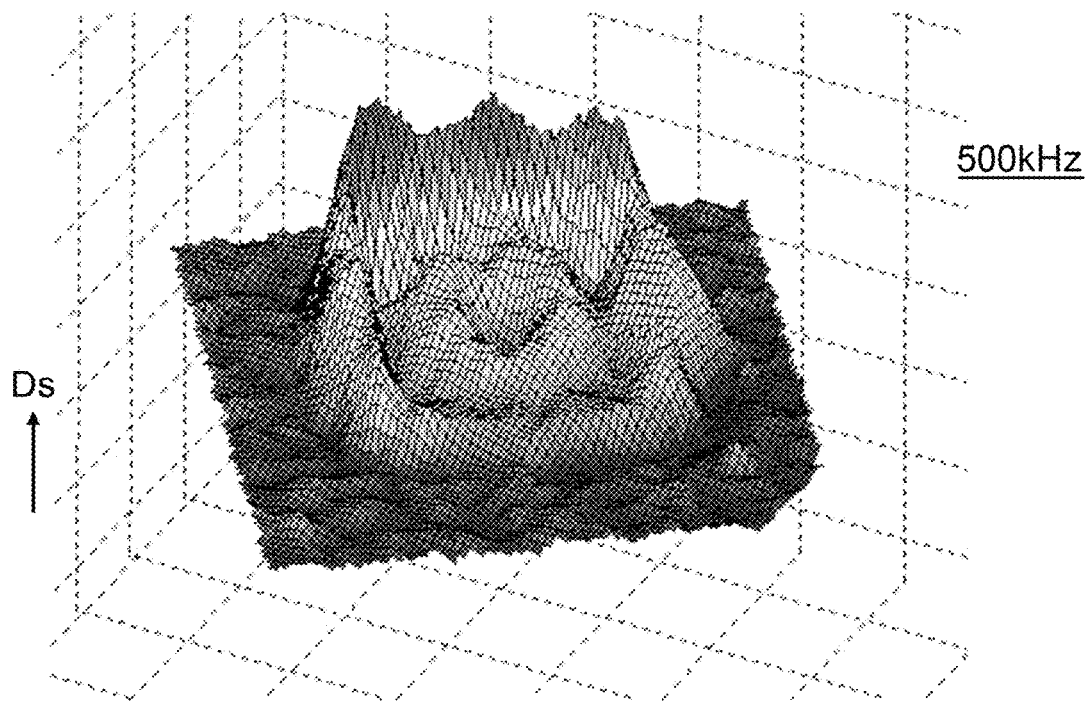
FIG. 11 is a schematic view showing the characteristics of the other sensor according to the first embodiment.
Figure 12:
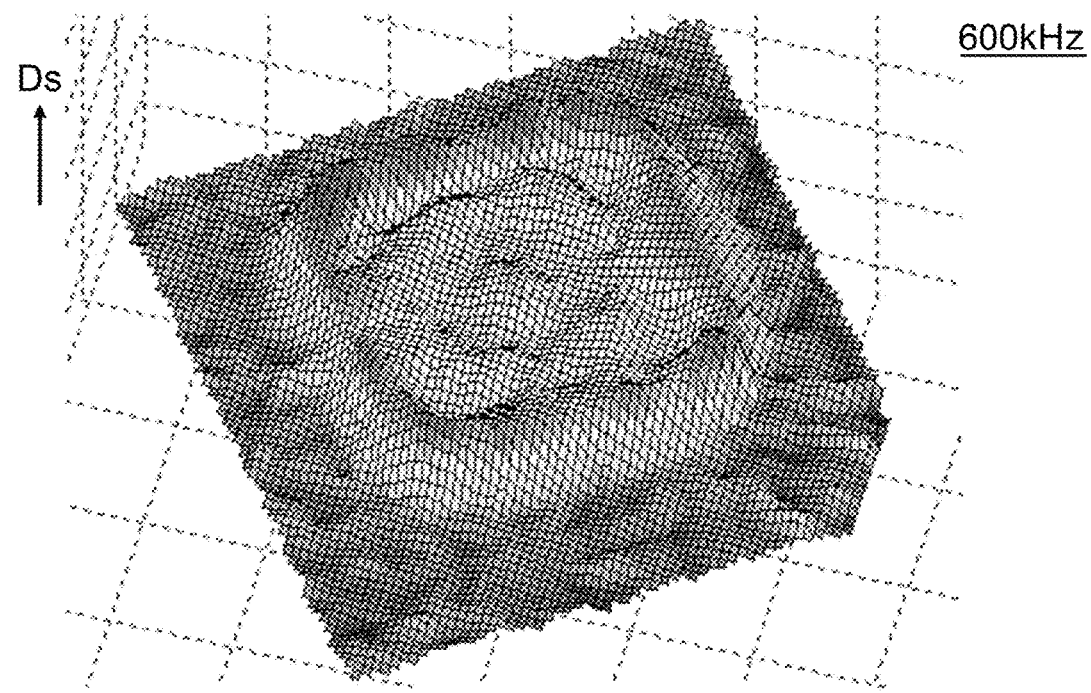
FIG. 12 is a schematic view showing the characteristics of the other sensor according to the first embodiment.

FIG. 6A and FIG. 6B are graphs illustrating characteristics of the other sensor according to the first embodiment.

These figures show measurement results of the frequency response characteristics of the sensor 111a. In these figures, the horizontal axis is a frequency f (Hz). The vertical axis of FIG. 6A is a displacement Ds (m). The vertical axis of FIG. 6B is a phase Ph (degrees).

As shown in FIG. 6A, peaks of the displacement Ds are observed when the frequency f is about 5 kHz, about 25.4 kHz, about 50.7 kHz, about 300 kHz, about 500 kHz, and about 600 kHz.

As shown in FIG. 6B, the phase Ph also changes with the change of the displacement Ds.

FIG. 7 to FIG. 12 are schematic views illustrating the characteristics of the other sensor according to the first embodiment.

These figures show the measurement results of the planar distribution of the displacement Ds of the film unit 20 (and the liquid 45) of the sensor 111a. FIG. 7 to FIG. 12 correspond respectively to the characteristics of the frequency f at 5 kHz, 25.4 kHz, 50.7 kHz, 300 kHz, 500 kHz, and 600 kHz.

As shown in FIG. 5 to FIG. 12, a surface wave due to free vibrations occurs in the liquid 45. By sensing the displacement Ds, the sound wave 80 of the high frequency f can be sensed with high sensitivity.

An example of characteristics of another sensor according to the embodiment will now be described.

Figure 13:
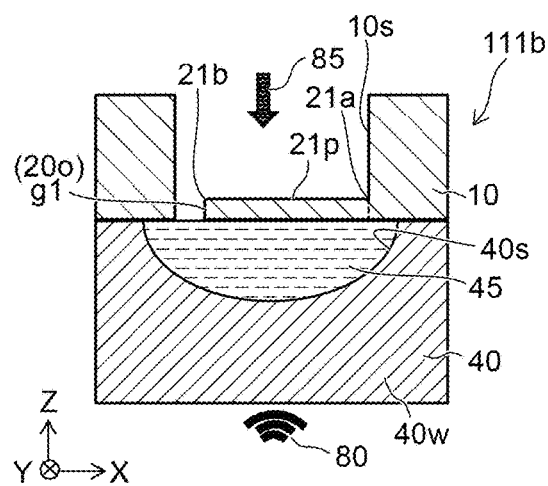
FIG. 13 is a schematic cross-sectional view showing the other sensor according to the first embodiment.

FIG. 13 is a schematic cross-sectional view illustrating the other sensor according to the first embodiment.

FIG. 13 illustrates the other sensor 111b according to the embodiment. The configuration of the film unit 20 of the sensor 111b is similar to that of the sensor 111a. In the sensor 111b, the configuration of the first space 40s in which the liquid 45 is contained is different from that of the sensor 111a.

In the sensor 111b, the diameter of the second space 10s (the cavity) is 200 μm. The thickness of the liquid 45 is 10 μm. The thickness of the film unit 20 is 300 nm. The thickness of the wall 40w of the container 40 is 3 mm. In other words, in the sensor 111b, the thickness of the liquid 45 is thinner than that of the sensor 111a. In the sensor 111b, the thickness of the wall 40w is thicker than that of the sensor 111a. In the sensor 111b as well, the film unit 20 includes silicon. The wall 40w includes PDMS. The liquid 45 includes silicone oil.

Figure 14A:
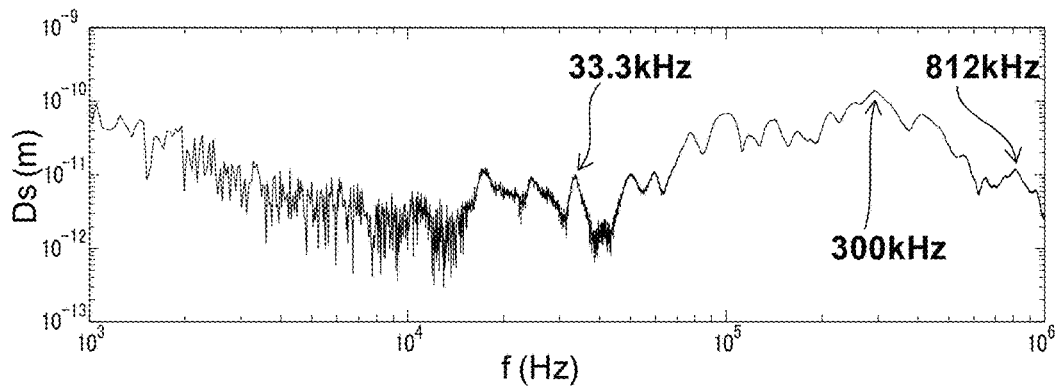
FIG. 14A and FIG. 14B are graphs showing characteristics of the other sensor according to the first embodiment.
Figure 14B:
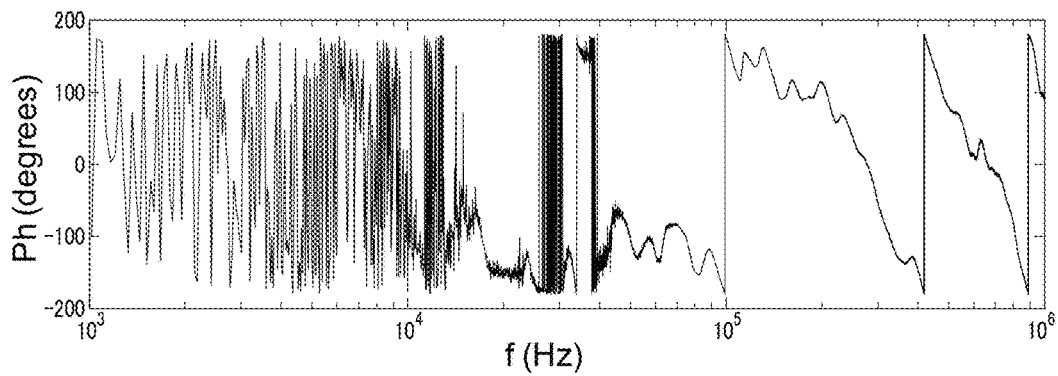

FIG. 14A and FIG. 14B are graphs illustrating characteristics of the other sensor according to the first embodiment.

These figures show measurement results of the frequency response characteristics of the sensor 111b.

As shown in FIG. 14A, peaks of the displacement Ds are observed when the frequency f is about 33.3 kHz, about 300 kHz, and about 812 kHz.

As shown in FIG. 14B, the phase Ph also changes with the change of the displacement Ds.

Figure 15:
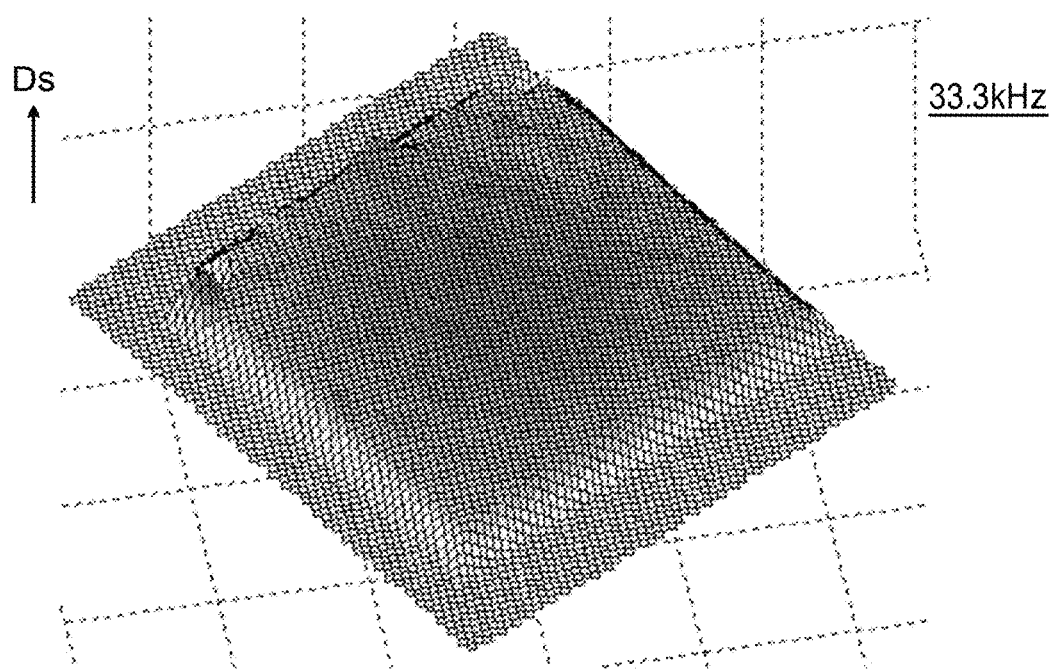
FIG. 15 is a schematic view showing characteristics of the other sensor according to the first embodiment.
Figure 16:
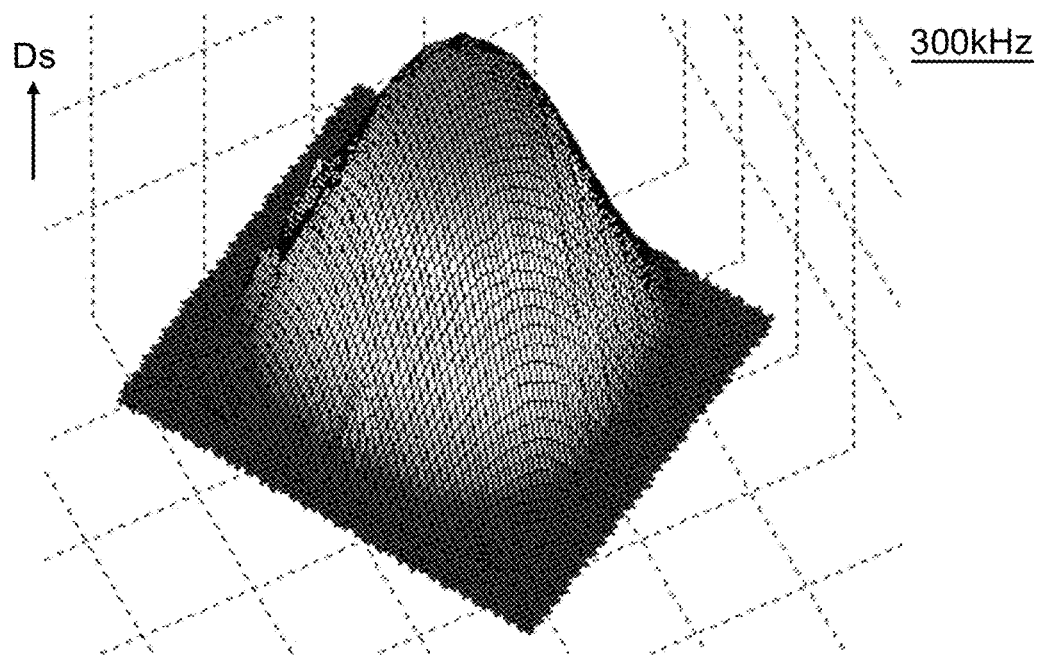
FIG. 16 is a schematic view showing characteristics of the other sensor according to the first embodiment.
Figure 17:
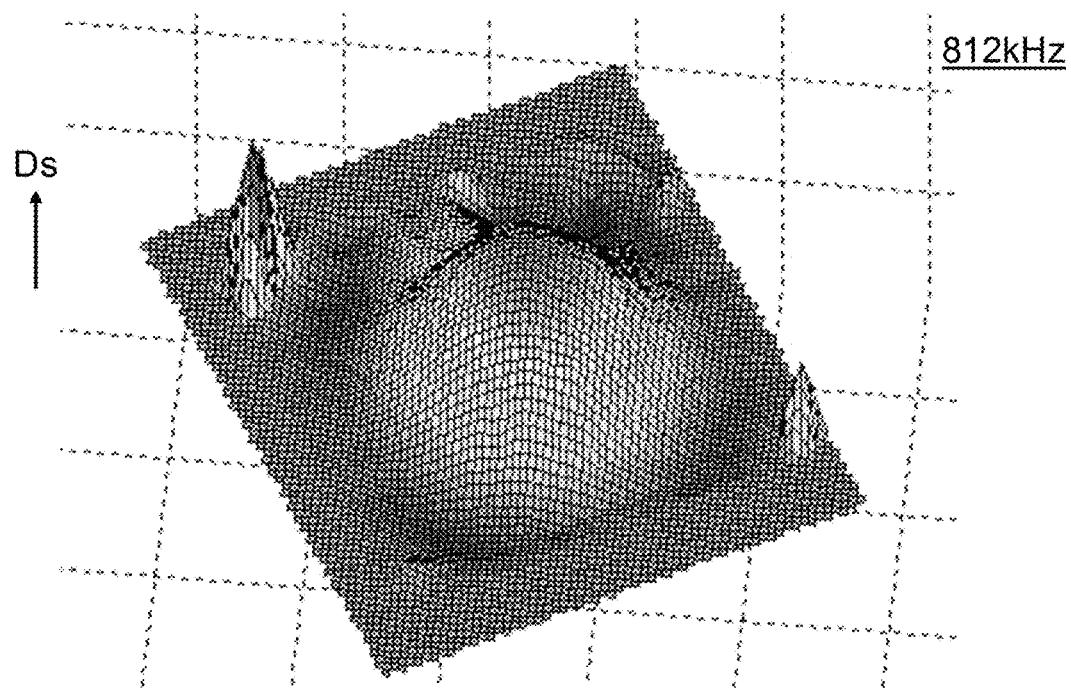
FIG. 17 is a schematic view showing characteristics of the other sensor according to the first embodiment.

FIG. 15 to FIG. 17 are schematic views illustrating characteristics of the other sensor according to the first embodiment.

These figures show the measurement results of the planar distribution of the displacement Ds of the film unit 20 (and the liquid 45) of the sensor 111b. FIG. 15 to FIG. 17 correspond respectively to the characteristics of the frequency f at 33.3 kHz, 300 kHz, and 812 kHz.

As shown in FIG. 15, in the case where the frequency f is relatively low, the displacement Ds (i.e., the displacement of the front surface of the liquid 45) positioned at the opening 20o is substantially aligned with the X-Y plane (a plane perpendicular to the Z-axis direction). Conversely, at a high frequency f as shown in FIG. 16, an extremely large displacement Ds occurs at the central portion of the film unit 20; and the displacement Ds is small at the peripheral portion of the film unit 20.

Based on these characteristics, the thickness of the liquid 45, etc., of the sensor are set appropriately.

For example, a piezoelectric AE sensor, microphone, or the like that utilizes the mechanical resonance of a piezoelectric element is used as an acoustic sensor that senses vibrations from the acoustic band to the ultrasonic band. Other methods for sensing the vibrations include electrostatic capacitance methods, resistance change methods, etc. High sensitivity is obtained easily in a piezoelectric sensor by utilizing the resonance characteristics of a piezoelectric ceramic. However, there are also problems such as the price being high, the size of the sensor being large, etc.

On the other hand, the popularity of microphones (acoustic sensors in the low frequency band) based on MEMS is increasing. The MEMS sensor is very advantageous for downsizing, price reduction, etc. There are expectations for MEMS sensors in not only pressure sensors and microphones but also in applications as sensors in the ultrasonic band.

In the MEMS sensor, a vibrating body such as a diaphragm, a cantilever, or the like is formed by, for example, a semiconductor process. The displacement and/or the strain is measured by the vibrating body and converted into a voltage. Thereby, the vibration is measured. The vibrating body has unique vibration characteristics according to the configuration and/or material properties of the vibrating body. A vibration displacement occurs in the vibrating body due to a vibration waveform input from the outside. The vibration displacement is extracted as an output by an appropriate method. In the case where the vibrating body is placed inside a gas, the amplitude becomes large particularly in the frequency band of the natural frequency vicinity; and as a result, high sensitivity is obtained at the natural frequency vicinity.

In the acoustic sensor of the low frequency band, a band lower than the primary natural frequency of the vibrating body is used. On the other hand, in the acoustic sensor of the ultrasonic band such as an AE sensor, etc., the sensitivity is high at the vicinity of the primary natural frequency.

Compared to the band of the natural frequency vicinity, the sensitivity decreases drastically in regions distal to the natural frequency. There is a method for increasing the bandwidth by providing damping by burying the entire sensor element inside a liquid. However, it is said that the sensitivity at the natural frequency vicinity also decreases greatly due to the damping.

In the embodiment, for example, the liquid 45 is encapsulated in the first space 40s on one surface of the film unit 20 (the vibrating body). Thereby, the vibration shape that occurs in the front surface of the liquid 45 due to the vibration is utilized. By encapsulating the liquid 45 in the first space 40s at the one surface, a larger amplitude (the displacement Ds) can be obtained than in the case where the entire vibrating body is buried inside the liquid 45. Thereby, sensing with high sensitivity becomes possible.

Compared to the characteristic vibration in air, a response in a wider band can be obtained for the vibration of the front surface of the liquid 45. By using the thin vibrating body, the vibrating body can be caused to vibrate in a configuration along the vibration occurring in the front surface of the liquid 45. In the embodiment, the vibration shape of the front surface of the liquid 45 is utilized actively.

In the embodiment, the sensing is performed at a position where the strain of the vibrating body is large. Thereby, high sensitivity can be obtained. An example of the position of the sensing is described below.

Figure 18A:
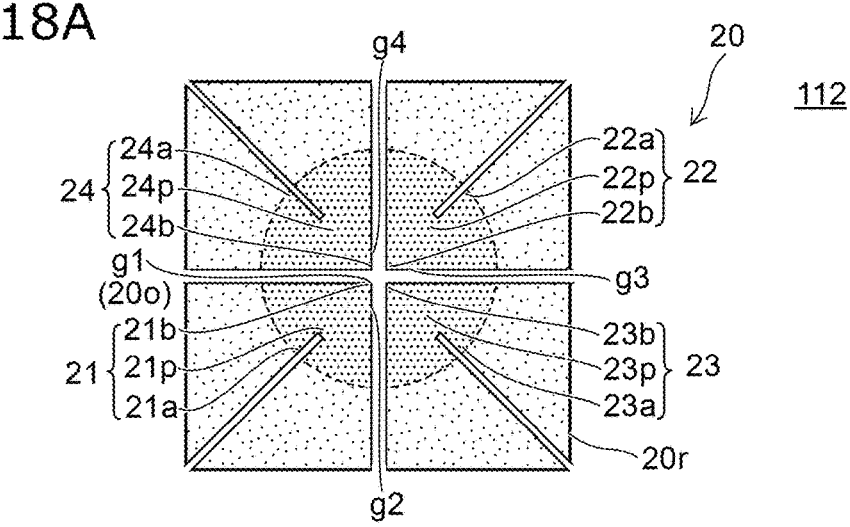
FIG. 18A and FIG. 18B are schematic plan views showing another sensor according to the first embodiment.
Figure 18B:
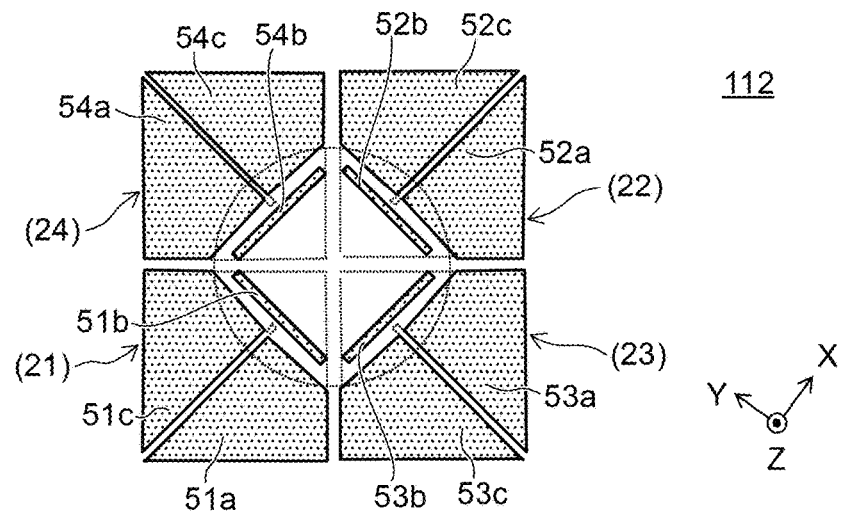
Figure 19A:
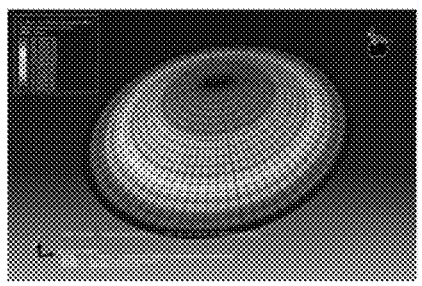
FIG. 19A to FIG. 19E are schematic perspective views showing characteristics of the other sensor according to the first embodiment.
Figure 19B:
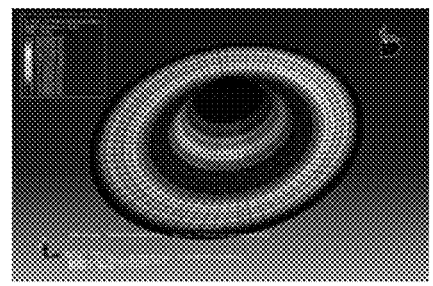
Figure 19C:
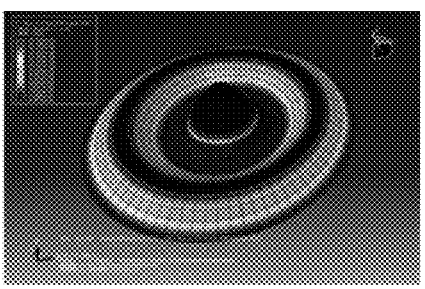
Figure 19D:
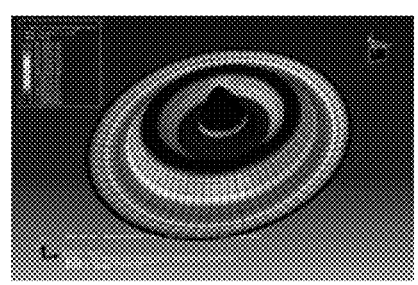
Figure 19E:
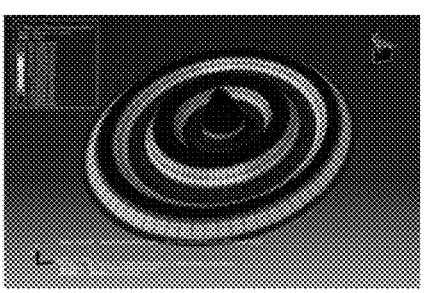

FIG. 18A and FIG. 18B are schematic plan views illustrating another sensor according to the first embodiment.

FIG. 18A illustrates the configuration of the film unit 20 of the other sensor 112 according to the embodiment. FIG. 18B illustrates the configurations of the electrodes of the sensor 112.

As shown in FIG. 18A, the configuration of the film unit 20 of the sensor 112 is similar to that of the sensor 110. On the other hand, as shown in FIG. 18B, the configurations of the electrodes are different from those of the sensor 110. Other than the configurations of the electrodes, the sensor 112 is similar to the sensor 110; therefore, a description other than the configurations of the electrodes is omitted.

In the sensor 112 as illustrated in FIG. 18B, the planar pattern of the second electrode 51b is a rectangle. Also, the portion (the side) of the first electrode 51a opposing the second electrode 51b is substantially parallel to the side of the first electrode 51a. On the other hand, the portion (the side) of the first counter electrode 51c opposing the second electrode 51b is substantially parallel to the side of the first electrode 51a. Such electrodes are provided to correspond to the first region 21. The electrodes that correspond to the second to fourth regions 22 to 24 also have similar pattern configurations.

Thus, in the embodiment, various modifications of the pattern configuration of the electrodes are possible. For example, the configurations of the electrodes may be configurations that are dependent on the configuration of the region of the film unit 20 (e.g., the sensor 110), or may be configurations independent of the configuration of the region of the film unit 20 (e.g., the sensor 112).

In the sensor 112, the pattern of the electrodes may be caused to match the crystal orientation of the silicon. In other words, in the sensor 112, for example, a current is caused to flow in the path between the first electrode 51a and the second electrode 51b. Further, the current is caused to flow in the path between the second electrode 51b and the first counter electrode 51c. On the other hand, a large change of the resistance with respect to the displacement of the displacement Ds is obtained in a designated crystal orientation. The direction of the path of the current is set to be aligned with an orientation in which a large change of the resistance is obtained. Thereby, sensing with higher sensitivity becomes possible.

In other words, in the sensor 112, the first sensing element 31 includes the crystal layer 13a (e.g., the monocrystalline layer) of silicon including the impurity, the first electrode 51a connected to one portion of the crystal layer 13a, and the second electrode 51b connected to one other portion of the crystal layer 13a. In such a case, the direction (in the example, the X-axis direction) from the first electrode 51a toward the second electrode 51b is aligned with one direction of the <110> direction or the <100> direction of the crystal layer 13a of silicon. Thereby, sensing with higher sensitivity becomes possible.

For example, in the case where the crystal layer 13a of silicon includes an n-type impurity, it is desirable for the direction from the first electrode 51a toward the second electrode 51b to be aligned with the monocrystal <100> direction of silicon. On the other hand, in the case where the crystal layer 13a of silicon includes a p-type impurity, it is desirable for the direction from the first electrode 51a toward the second electrode 51b to be aligned with the monocrystal <110> direction of silicon.

In the embodiment, for example, the change of the resistance for the sensing elements (the first sensing element 31, etc.) may be converted into a voltage difference using, for example, a bridge circuit. Further, the voltage difference may be amplified by an amplifier circuit (e.g., an operational amplifier, etc.). The signal of the voltage difference is used as the sense signal of the sound wave 80.

In the example, the direction from the first electrode 51a toward the second electrode 51b is tilted with respect to the extension direction of at least one portion of an outer edge 20r of the film unit 20 (referring to FIG. 18A). The configuration of the outer edge 20r of the film unit 20 corresponds to the exterior form of the element of the sensor. The configuration of the outer edge 20r of the film unit 20 is determined based on various design components. On the other hand, the crystal orientation of the crystal layer 13a is dependent on the wafer of silicon. By setting the direction from the first electrode 51a toward the second electrode 51b to be tilted with respect to the outer edge 20r of the film unit 20, an efficient arrangement of the element and highly-sensitive sensing are obtained.

In the sensors 110 and 112, the directions of the current (i.e., the direction in which the multiple electrodes are separated from each other) intersect (e.g., are orthogonal) for the multiple sensing elements. For example, in the first region 21 of the sensor 112, the first electrode 51a and the second electrode 51b are separated from each other along the X-axis direction. On the other hand, in the third region 23, the electrode 53a and the electrode 53b are separated from each other along the Y-axis direction. By setting the directions of the current to intersect (e.g., to be orthogonal), the sensing elements are arranged easily in directions in which, for example, the change of the piezoresistance is a maximum.

An example of the vibration characteristics of the film unit 20 will now be described.

In the following example, the planar configuration of the film unit 20 is a circle; and the periphery of the film unit 20 is fixed continuously. In other words, the film unit 20 is, for example, a circular diaphragm.

FIG. 19A to FIG. 19E are schematic perspective views illustrating characteristics of the other sensor according to the first embodiment.

These figures illustrate simulation results of the vibration characteristics of the film unit 20. FIG. 19A to FIG. 19E show the low-order to high-order natural frequency shapes of the circular diaphragm.

It can be seen from FIG. 19A to FIG. 19E that in the vibration state, a large strain occurs at portions proximal to the fixed end and the portions of the anti-nodes of the vibration.

On the other hand, for the cantilever (e.g., referring to FIG. 7 to FIG. 12 and FIG. 15 to FIG. 17), a large strain occurs in the fixed end portion.

Thus, the region where the large strain is obtained changes according to the configuration.

In the embodiment, the position of the sensing unit 30 (e.g., the first sensing element 31) is set at the position where the strain is large. For example, the film unit 20 has a position where the strain along the vibration shape of the front surface of the liquid 45 is large. The first sensing element 31 is disposed at this position. Thereby, the vibrations in the desired frequency band can be measured with high sensitivity. For example, the deformation is large in portions where the strain is large.

In the embodiment, the configuration of the sensor is arbitrary; the arrangement of the sensing elements also is arbitrary; and each may be modified independently.

Figure 20A:
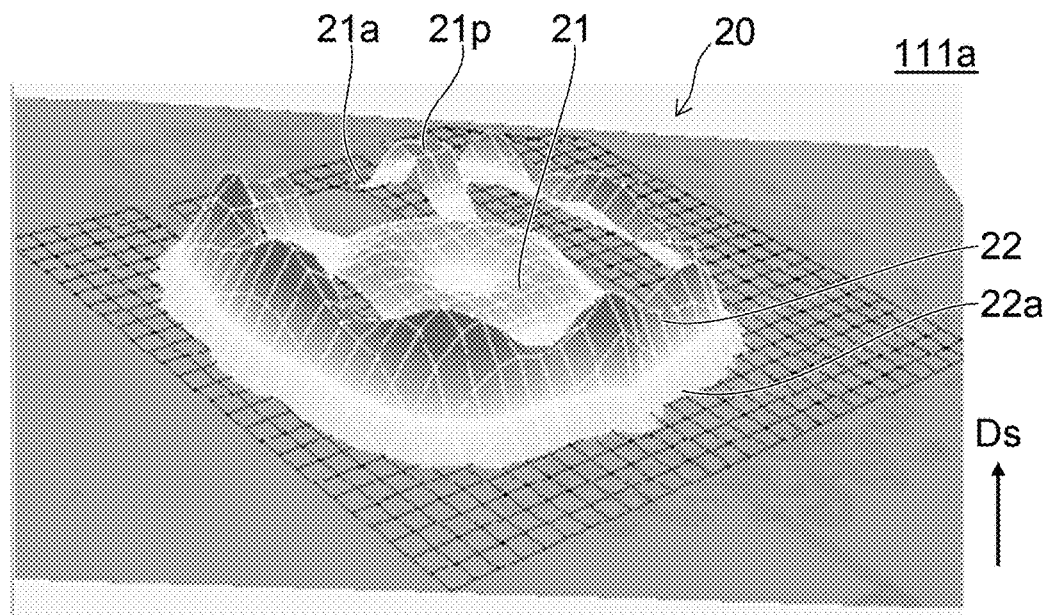
FIG. 20A and FIG. 20B are schematic perspective views showing characteristics of the other sensor according to the first embodiment.
Figure 20B:
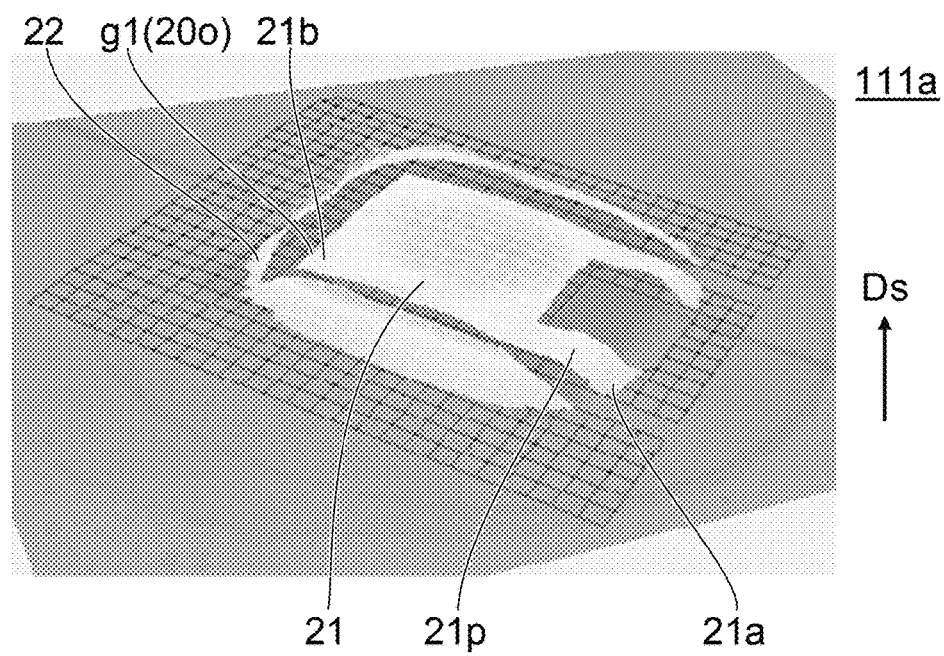

FIG. 20A and FIG. 20B are schematic perspective views illustrating characteristics of the other sensor according to the first embodiment.

These figures show the measurement results of the planar distribution of the displacement Ds of the film unit 20 (and the liquid 45) of the sensor 111a described above. In FIG. 20A, the frequency f is 300 kHz; and in FIG. 20B, the frequency f is 10 Hz.

It can be seen from FIG. 20A and FIG. 20B that the film unit 20 (in the example, the cantilever) is vibrationally excited by the liquid 45; and a large strain (the displacement Ds) occurs at the vicinity of the fixed end of the film unit 20. In other words, for example, a large strain (the displacement Ds) occurs at the vicinity of the first end portion 21a of the first region 21 of the film unit 20. Higher sensitivity is obtained by disposing the sensing elements at the portions where the large strain is obtained.

It can be seen from FIG. 20A that the large strain (the displacement Ds) is obtained not only in the first region 21 of the cantilever configuration but also in the region (the second region 22) surrounding the periphery of the first region 21. The sensing elements may be disposed in this region.

An example of the configuration of the film unit 20 and the arrangement of the sensing elements (e.g., the first sensing element 31, etc.) will now be described. Otherwise, the configuration is not shown hereinbelow for easier viewing of the drawings.

Figure 21A:
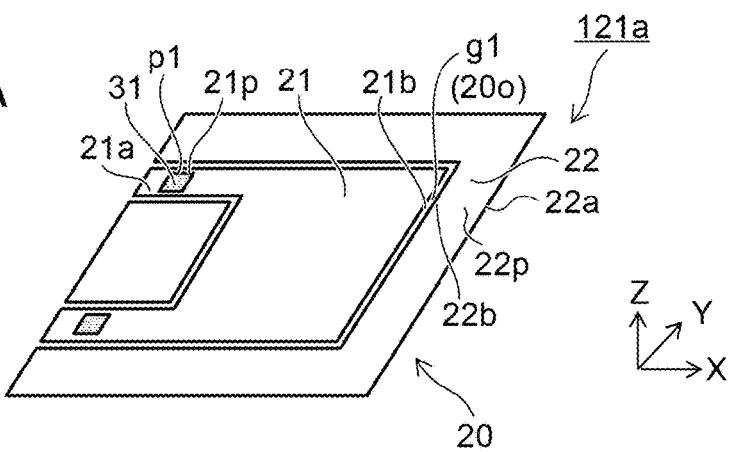
FIG. 21A to FIG. 21C are schematic perspective views showing other sensors according to the first embodiment.
Figure 21B:
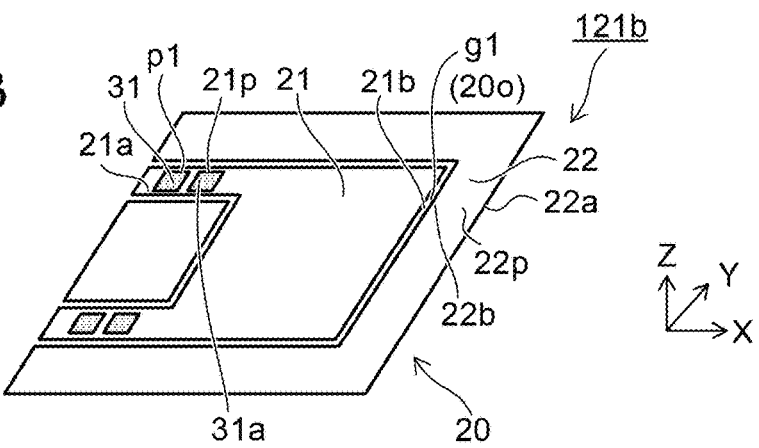
Figure 21C:
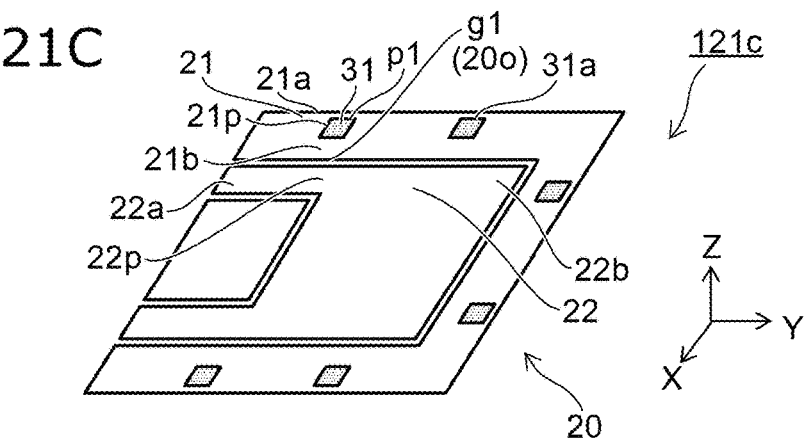

FIG. 21A to FIG. 21C are schematic perspective views illustrating other sensors according to the first embodiment.

In a sensor 121a as shown in FIG. 21A, the first region 21 of the film unit 20 has a cantilever configuration. The first sensing element 31 is disposed at the vicinity of the fixed end (the first end portion 21a) of the first region 21. In other words, the first portion 21p is proximal to the first end portion 21a.

In other words, in the sensor 121a, the first region 21 includes the first opposite end 21b on the side opposite to the first end portion 21a. Also, the first sensing element 31 is disposed at a first position p1 inside the first portion 21p. The distance between the first end portion 21a and the first position p1 is shorter than the distance between the first opposite end 21b and the first position p1.

By disposing the first sensing element 31 at the vicinity of the fixed end, for example, the first sensing element 31 is subjected to the large strain shown in FIG. 20A. Thereby, high sensitivity is obtained.

In the embodiment, for example, the position of the center between the first electrode 51a and the second electrode 51b can be used as the position where the first sensing element 31 is disposed.

In the sensor 121a, the pattern configuration of the film unit 20 is not point-symmetric. By setting the cantilever to have an asymmetric configuration, for example, a large strain can be caused to occur at a designated position of the film unit 20. By providing a sensing element at the position, highly-sensitive sensing can be performed.

In a sensor 121b as shown in FIG. 21B, multiple sensing elements (the first sensing element 31 and a second sensing element 31a) are disposed at the vicinity of the fixed end (the first end portion 21a) of the first region 21. By using the multiple sensing elements, for example, the interference of the phases can be suppressed; further, highly-sensitive sensing becomes possible.

In a sensor 121c as shown in FIG. 21C, the first region 21 is provided around the second region 22 having the cantilever configuration. Also, the sensing elements (the first sensing element 31 and the second sensing element 31a) are provided in the first region 21. In such a case as well, the sensing elements are subjected to the large strain shown in FIG. 20A.

In the sensor 121c, the first region 21 is aligned with the edge of the film unit 20. In other words, the length of the first region 21 extending from the first end portion 21a is shorter than the width. In other words, the length of the first region 21 from the first end portion 21a along the extension direction toward the first portion 21p is shorter than the length (the width) perpendicular to the extension direction recited above and perpendicular to the Z-axis direction (the first direction from the container 40 toward the supporter 10). The sensing elements may be disposed in such a first region 21.

In the example, multiple sensing elements are arranged along the outer edge of the first region 21 of the film unit 20. For example, the sensing unit 30 includes the first sensing element 31 and the second sensing element 31a provided at the first portion 21p. The direction from the first sensing element 31 toward the second sensing element 31a intersects the extension direction of the first region 21.

In the sensor 121b and the sensor 121c, multiple sensing elements are provided in one region. Thereby, for example, the fluctuation of the sensing, etc., can be suppressed. For example, the fluctuation of the sensing is affected by the fluctuation of the configuration of the film unit 20, the fluctuation of the thickness of the film unit 20, the fluctuation of the physical properties of the film unit 20, etc. Further, the fluctuation of the sensing is affected by the fluctuation of the characteristics of the sensing elements. By providing the multiple sensing elements, stable sensing having low fluctuation becomes possible.

Figure 22A:
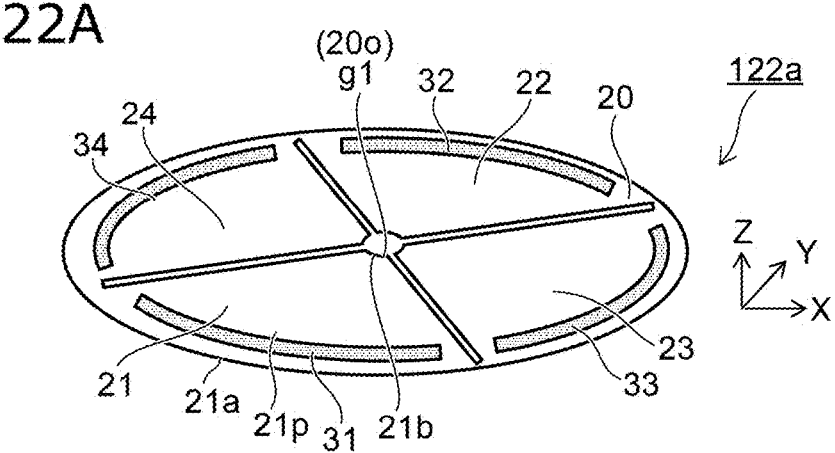
FIG. 22A to FIG. 22C are schematic perspective views showing other sensors according to the first embodiment.
Figure 22B:
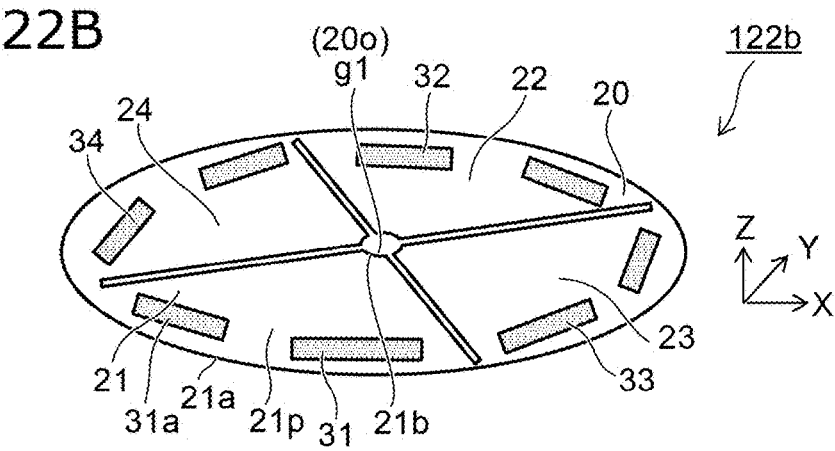
Figure 22C:
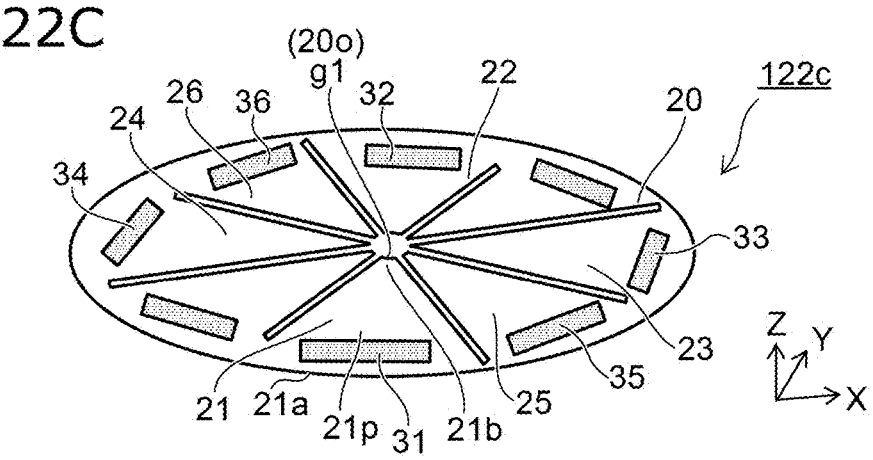

FIG. 22A to FIG. 22C are schematic perspective views illustrating other sensors according to the first embodiment.

In a sensor 122a as illustrated in FIG. 22A, the first to fourth regions 21 to 24 are provided in the film unit 20. The outer edge of the film unit 20 has an arc-like configuration. In the example, the opening 20o is positioned at the central portion of the film unit 20. The opening 20o includes a circular portion and slit portions having line configurations. The portion of the opening 20o positioned at the central portion is the circle. By setting the configuration of the central portion to be a circle, there are no sharp portions at the edge of the film unit 20. Thereby, for example, the reliability increases.

In a sensor 122b as illustrated in FIG. 22B, multiple sensing elements are provided in one region of the film unit 20. For example, the first sensing element 31 and the second sensing element 31a are provided in the first region 21. Thereby, for example, the fluctuation of the sensing, etc., can be suppressed.

In a sensor 122c as illustrated in FIG. 22C, the first to sixth regions 21 to 26 are provided in the film unit 20. A fifth sensing element 35 is provided on a fifth region 25. A sixth sensing element 36 is provided on the sixth region 26.

In the embodiment, the number of regions and the number of slits (or openings 20o) provided in the film unit 20 are arbitrary. The number of sensing elements provided in each of the multiple regions also is arbitrary.

Figure 23A:
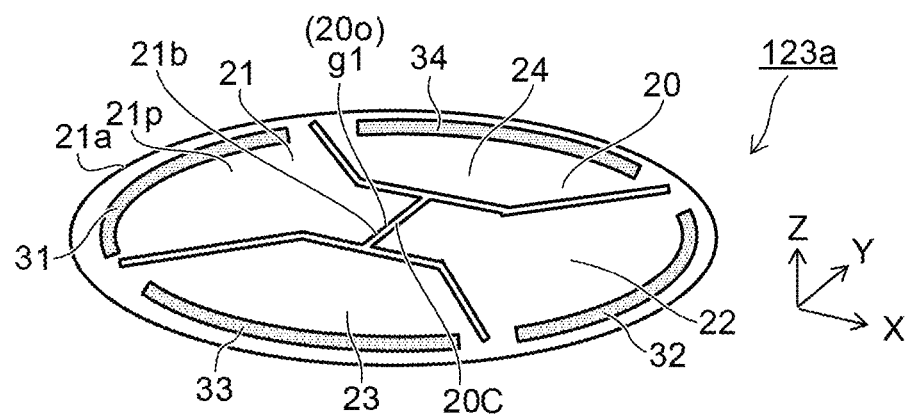
FIG. 23A and FIG. 23B are schematic perspective views showing other sensors according to the first embodiment.
Figure 23B:
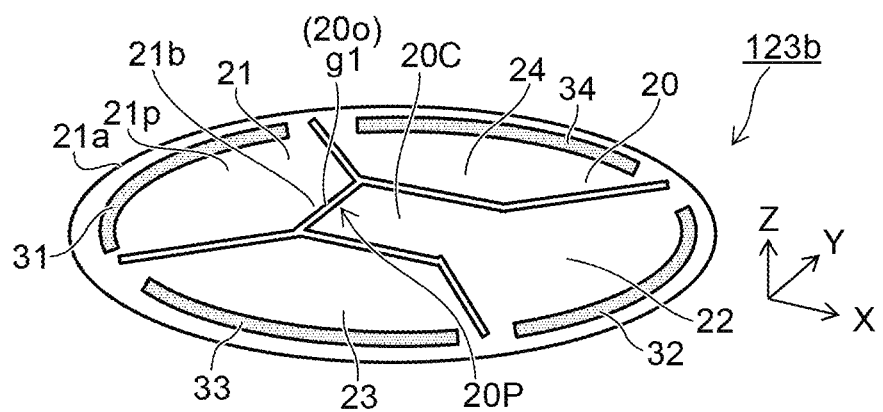

FIG. 23A and FIG. 23B are schematic perspective views illustrating other sensors according to the first embodiment.

In the film unit 20 in a sensor 123a as illustrated in FIG. 23A, the length in the extension direction of the first region 21 (the length between the first end portion 21*a* and the first opposite end 21*b*) and the length in the extension direction of the second region 22 each are longer than the length in the extension direction of the third region 23 and longer than the length in the extension direction of the fourth region 24. In other words, the configurations of the regions are different from each other. By setting the configurations of the regions to be different, the frequency at which the large strain is obtained changes. Highly-sensitive sensing in a wide frequency range becomes possible.

In the sensor 123*a*, a circle portion is not provided in the opening 20*o*. The opening 20*o* is made of gaps having slit configurations. Thereby, the outflowing from the opening 20*o* of the liquid 45 can be suppressed further.

In a sensor 123*b* as illustrated in FIG. 23B, the opening 20*o* is not provided at the central portion of the film unit 20. In other words, the film unit 20 includes a central portion 20C, and a peripheral portion 20P around the central portion 20C. In the sensor 123*b*, the opening 20*o* is positioned at the peripheral portion 20P. In the case where the opening 20*o* is provided at the central portion 20C of the film unit 20, the liquid 45 may outflow easily. By providing the opening 20*o* at the peripheral portion 20P, the outflow of the liquid 45 can be suppressed further.

Figure 24A:
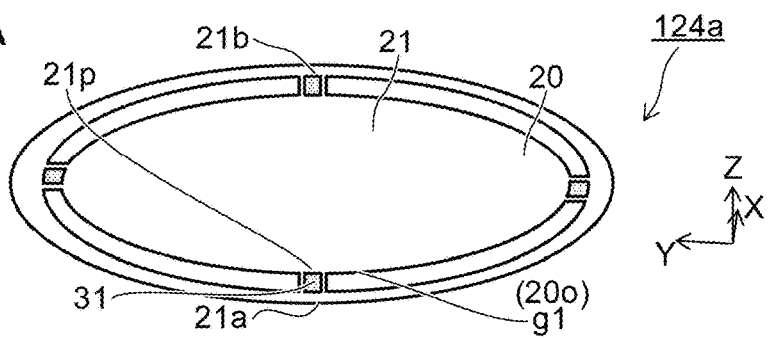
FIG. 24A and FIG. 24E are schematic perspective views showing other sensors according to the first embodiment.
Figure 24B:
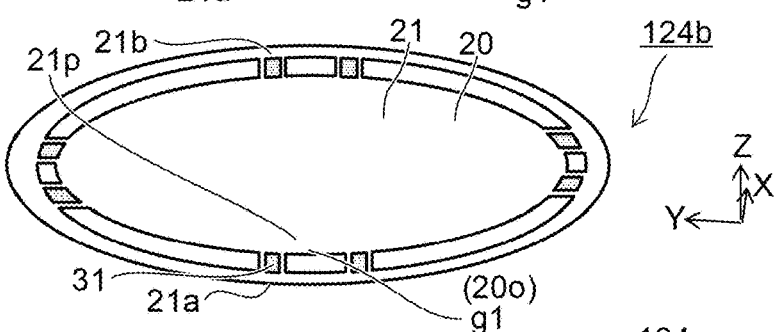
Figure 24C:
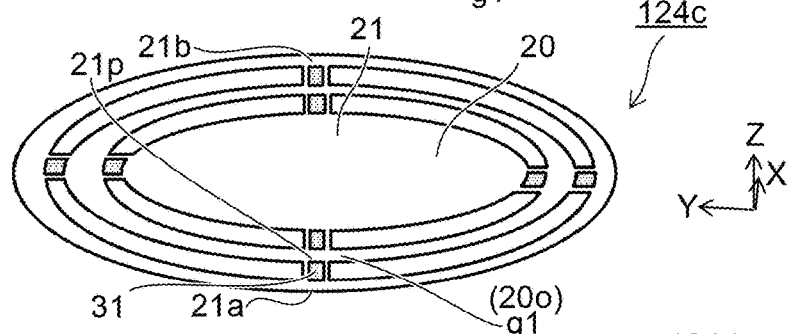
Figure 24D:
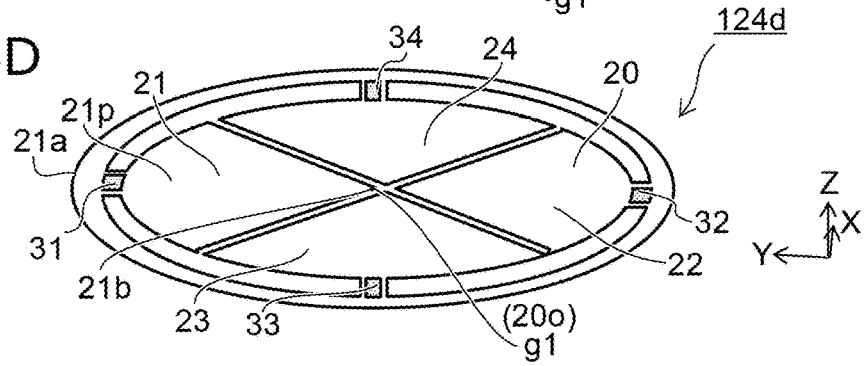
Figure 24E:
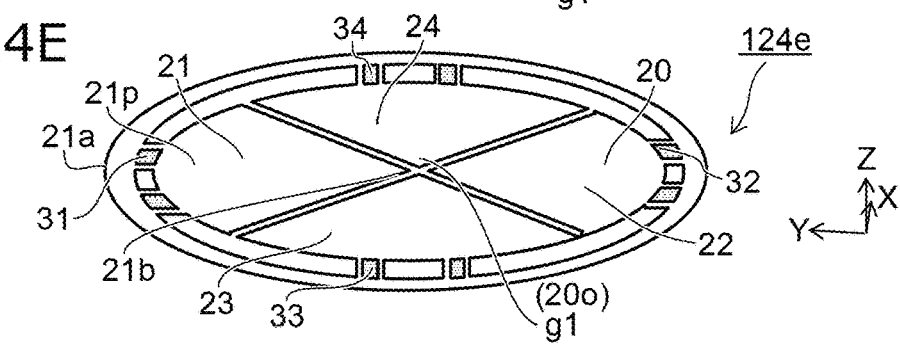

FIG. 24A and FIG. 24E are schematic perspective views illustrating other sensors according to the first embodiment.

In a sensor 124*a* as illustrated in FIG. 24A, the first region 21 of the film unit 20 includes four beams and a film supported by the beams. The sensing elements (the first sensing elements 31) are provided at the portions of the beams. In the example, the surface area of the sensing elements (e.g., the surface area of the variable resistance units) is extremely small compared to the surface area of the entire film unit 20. For example, in the case where a large strain occurs at the portions of the beams, the sensing elements may be disposed at only the portions of the beams.

In a sensor 124*b* as illustrated in FIG. 24B, multiple beams in the first region 21 of the film unit 20 are used as one set to support the film. In the example, four sets are provided. In the example, multiple beams are arranged in parallel.

In a sensor 124*c* as illustrated in FIG. 24C, multiple beams in the first region 21 of the film unit 20 are used as one set to support the film. In the example, four sets are provided. In the example, multiple beams are arranged in series.

In a sensor 124*d* as illustrated in FIG. 24D, the first to fourth regions 21 to 24 are provided in the film unit 20. Each of the regions is connected to the outer edge portion of the film unit 20 by a beam. The sensing elements are provided at the portions of the beams.

In a sensor 124*e* as shown in FIG. 24E, each of the first to fourth regions 21 to 24 of the film unit 20 is connected to the outer edge portion of the film unit 20 by multiple beams. The sensing elements are provided at portions of each of the multiple beams.

In the sensors 124*a* to 124*e*, the surface area of the portions (the beams) where the sensing elements are provided is extremely small compared to the surface area of the film unit 20. A large strain occurs easily in the beam. Thereby, the sensitivity of the sensing can be increased.

Figure 25:
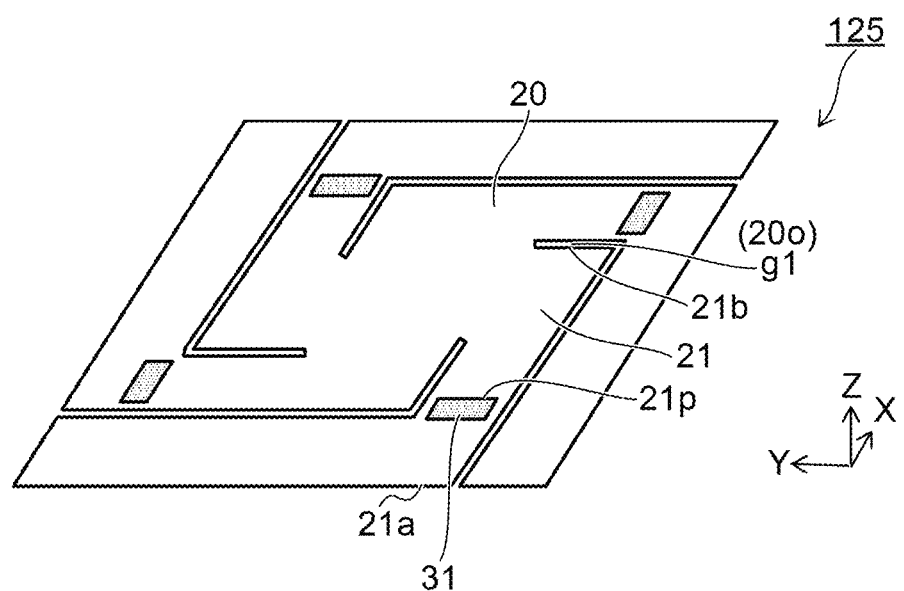
FIG. 25 is a schematic perspective view showing another sensor according to the first embodiment.

FIG. 25 is a schematic perspective view illustrating another sensor according to the first embodiment.

In a sensor 125 as illustrated in FIG. 25, the film unit 20 has a gammadion cross configuration. In the cantilever configuration, for example, twisting deformation occurs easily in the film unit 20. Conversely, in the gammadion cross configuration, the twisting deformation of the film unit 20 can be suppressed. As a result, the strain in the intended direction (e.g., the tensile strain) is obtained effectively.

Figure 26A:
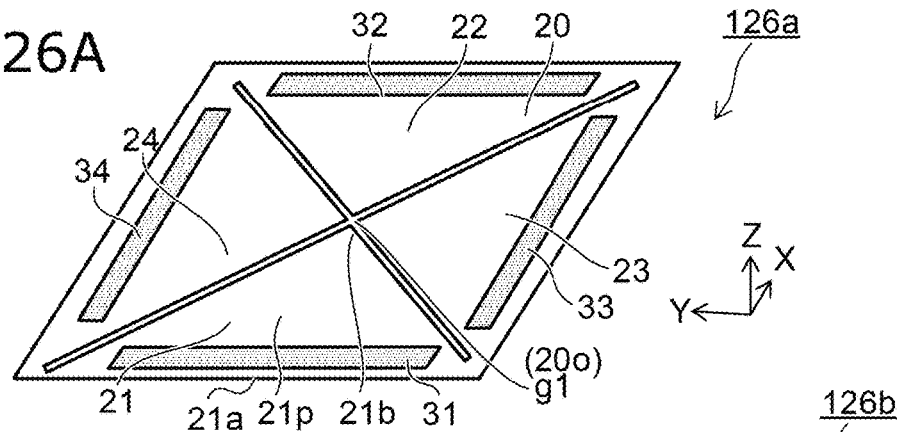
FIG. 26A to FIG. 26C are schematic views showing other sensors according to the first embodiment.
Figure 26B:
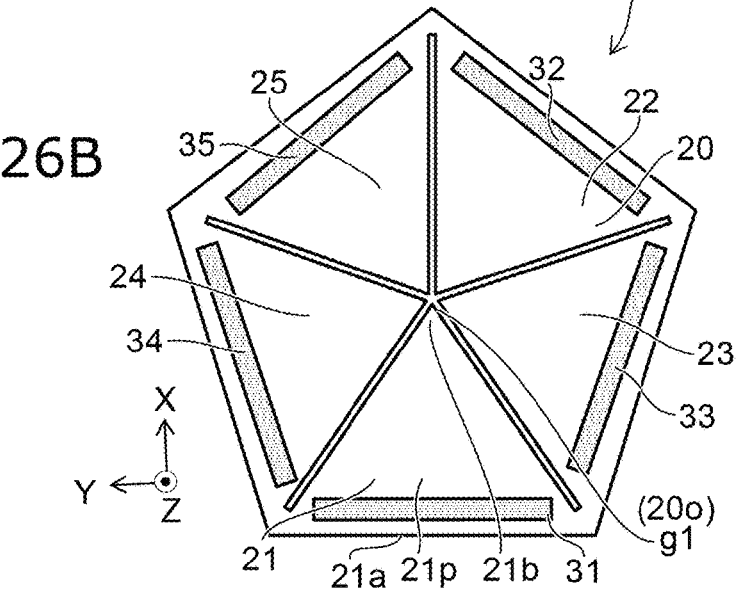
Figure 26C:
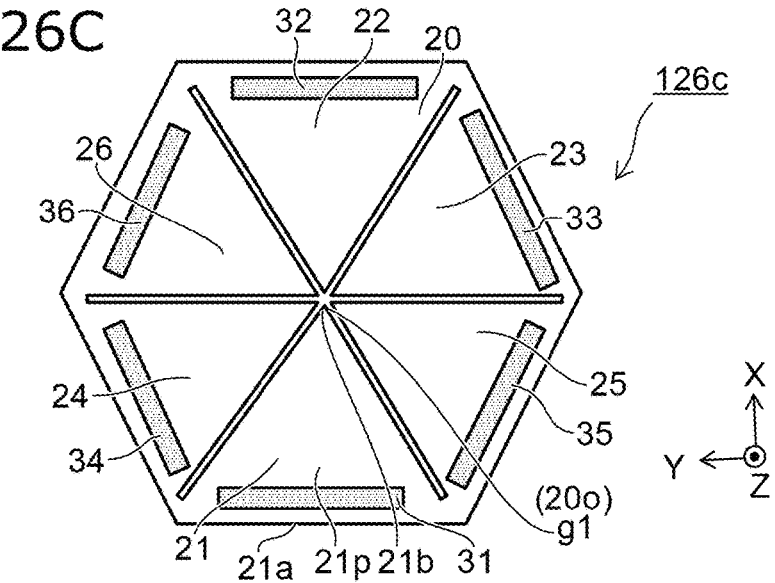

FIG. 26A to FIG. 26C are schematic views illustrating other sensors according to the first embodiment.

FIG. 26A is a schematic perspective view. FIG. 26B and FIG. 26C are schematic plan views.

In a sensor 126*a* as shown in FIG. 26A, the exterior form of the film unit 20 is a quadrilateral. The first to fourth regions 21 to 24 are provided. Slits are provided between the regions. Sensing elements are provided respectively in the regions.

In a sensor 126*b* as illustrated in FIG. 26B, the exterior form of the film unit 20 is a pentagon. The first to fifth regions 21 to 25 are provided. Slits are provided between the regions. Sensing elements (the first to fifth sensing elements 31 to 35) are provided respectively in the regions.

In a sensor 126*c* as illustrated in FIG. 26C, the exterior form of the film unit 20 is a hexagon. The first to sixth regions 21 to 26 are provided. Slits are provided between the regions. Sensing elements (the first to sixth sensing elements 31 to 36) are provided respectively in the regions.

For example, in the sensors 126*b* and 126*c*, the mixed input of asymmetric signals can be sensed by using the outputs of sensing elements provided at asymmetric positions inside the film unit 20. The fluctuation can be reduced by averaging the outputs of the multiple sensing elements. Thereby, the sensitivity can be increased further.

Figure 27A:
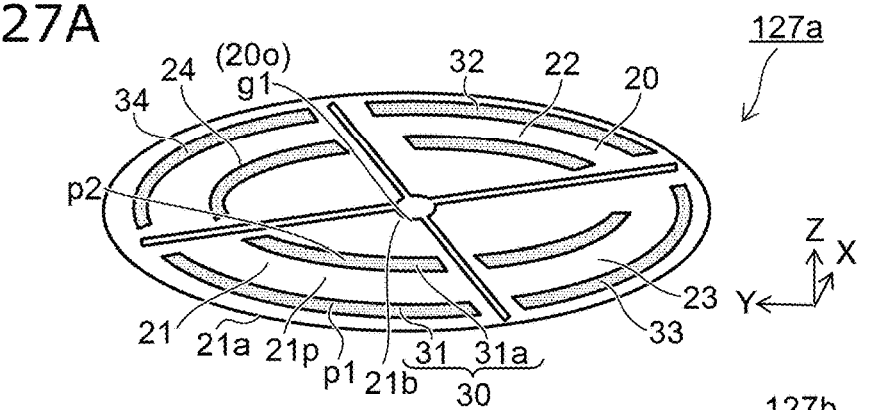
FIG. 27A and FIG. 27B are schematic perspective views showing other sensors according to the first embodiment.
Figure 27B:
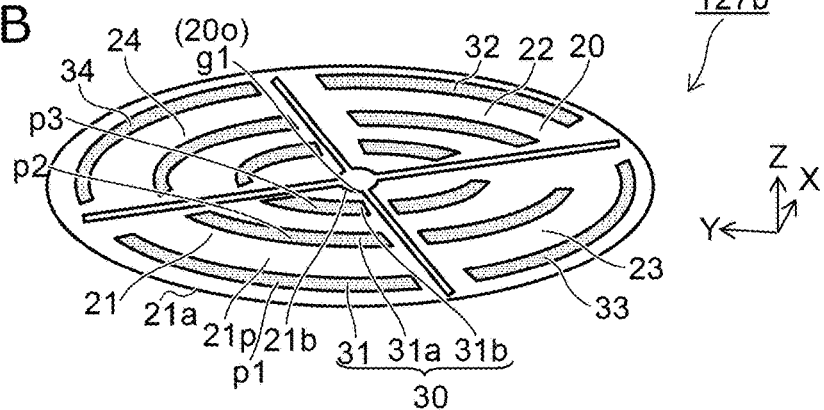

FIG. 27A and FIG. 27B are schematic perspective views illustrating other sensors according to the first embodiment.

In a sensor 127*a* as illustrated in FIG. 27A, multiple sensing elements are provided in each of the regions of the film unit 20. For example, the first sensing element 31 and the second sensing element 31*a* are provided in the first region 21.

In a sensor 127*b* as illustrated in FIG. 27B, the first sensing element 31, the second sensing element 31*a*, and a third sensing element 31*b* are provided in the first region 21.

The first sensing element 31 is provided between the first end portion 21*a* and the first opposite end 21*b*. The second sensing element 31*a* is provided between the first sensing element 31 and the first opposite end 21*b*. The third sensing element 31*b* is provided between the second sensing element 31*a* and the first opposite end 21*b*.

For example, in the sensor 127*a*, the sensing unit 30 includes the first sensing element 31 and the second sensing element 32. The first sensing element 31 is provided at the first position p1 of the first portion 21*p*. The second sensing element 31*a* is provided at a second position p2 of the first portion 21*p*. The first region 21 includes the first opposite end 21*b* on the side opposite to the first end portion 21*a*. The direction from the first position p1 toward the second position p2 is aligned with the direction from the first end portion 21*a* toward the first opposite end 21*b*.

For example, in the sensor 127*b*, the sensing unit 30 further includes the third sensing element 31*b*. The third sensing element 31*b* is provided at a third position p3 of the first portion 21*p*. The direction from the first position p1 toward the third position p3 is aligned with the direction from the first end portion 21*a* toward the first opposite end 21*b*.

For example, the position inside the film unit 20 where a large strain is obtained changes according to the frequency of the sound wave 80 applied to the liquid 45 and the film unit 20.

For example, the first sensing element 31 senses the sound wave 80 of about 25 kHz with high sensitivity. For example, the second sensing element 31a senses the sound wave 80 of about 50 kHz with high sensitivity. For example, the third sensing element 31b senses the sound wave 80 of about 300 kHz with high sensitivity.

In the sensors 127a and 127b, the sound wave 80 of a designated frequency can be sensed selectively with high sensitivity. The sum of and difference between the outputs of the multiple sensing elements may be utilized.

For example, by providing the multiple sensing elements in the radial direction from the central portion of the film unit 20 toward the outer edge, the sound wave 80 of different frequencies can be sensed with high sensitivity.

Figure 28A:
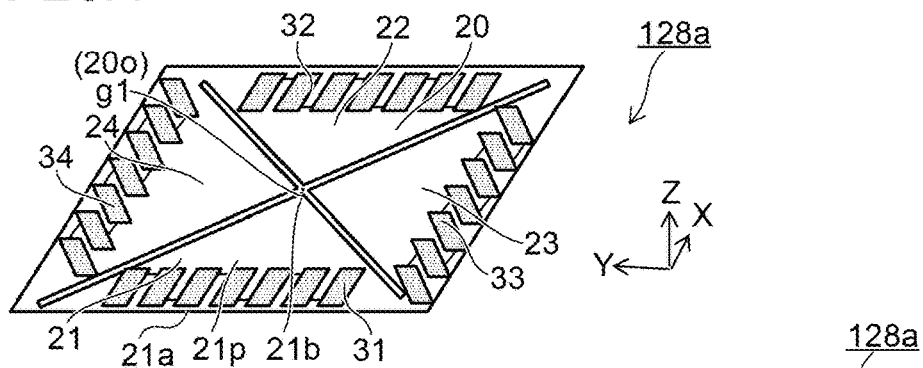
FIG. 28A and FIG. 28B are schematic perspective views showing other sensors according to the first embodiment.
Figure 28B:
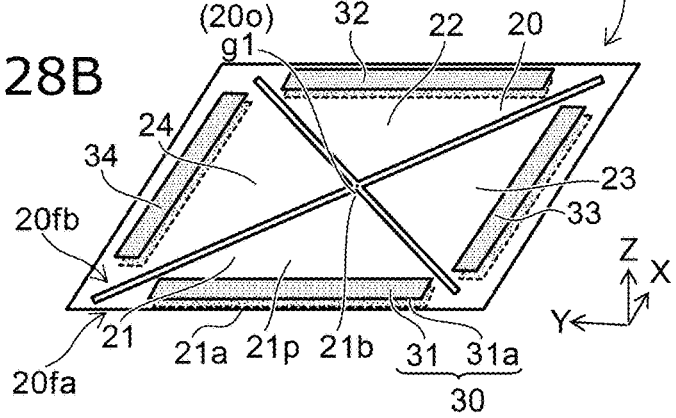
Figure 29:
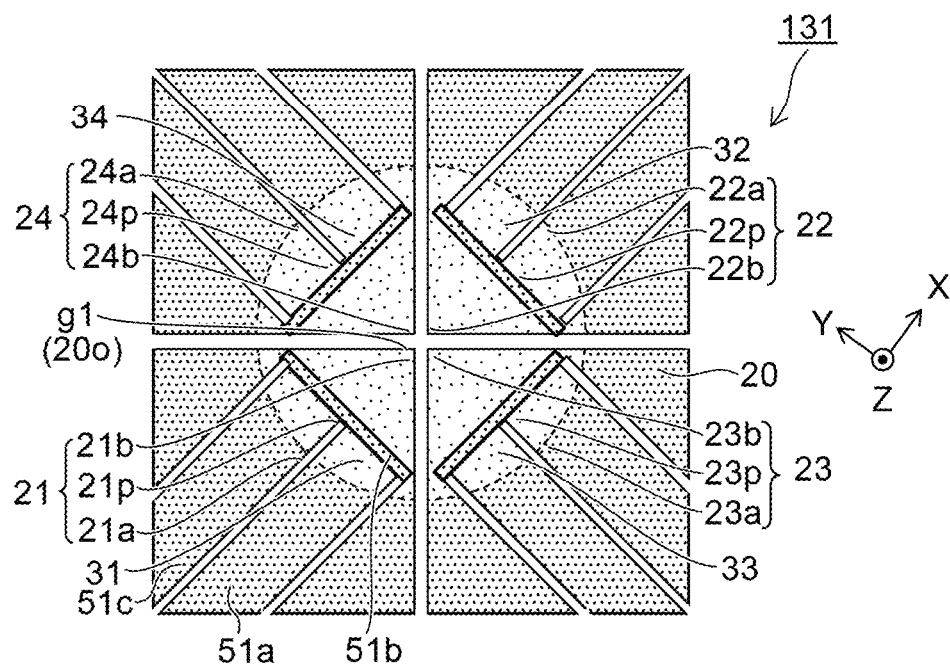
FIG. 29 is a schematic plan view showing other sensors according to the first embodiment.
Figure 30:
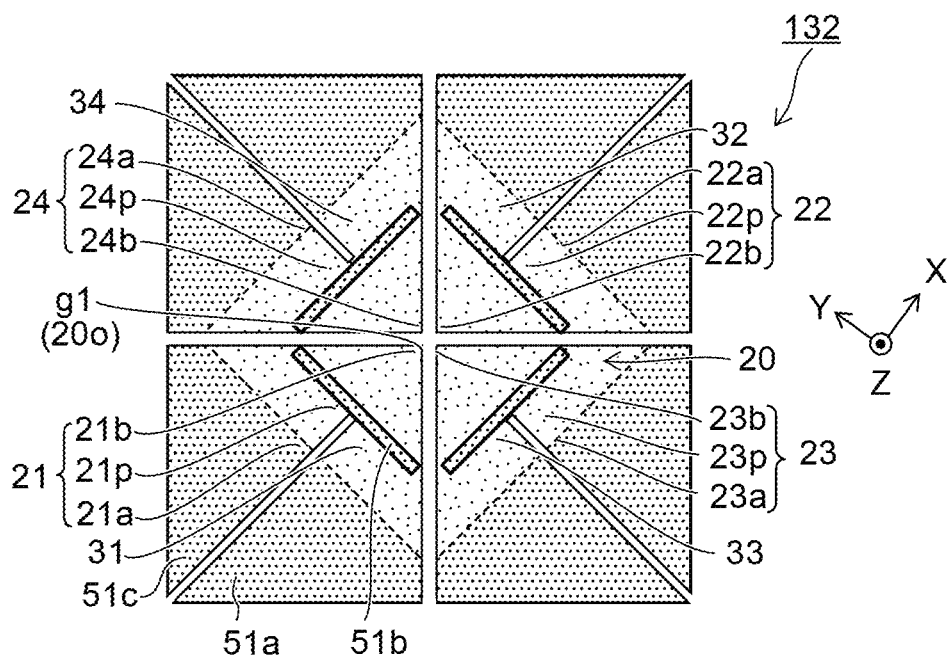
FIG. 30 is a schematic plan view showing other sensors according to the first embodiment.
Figure 31:
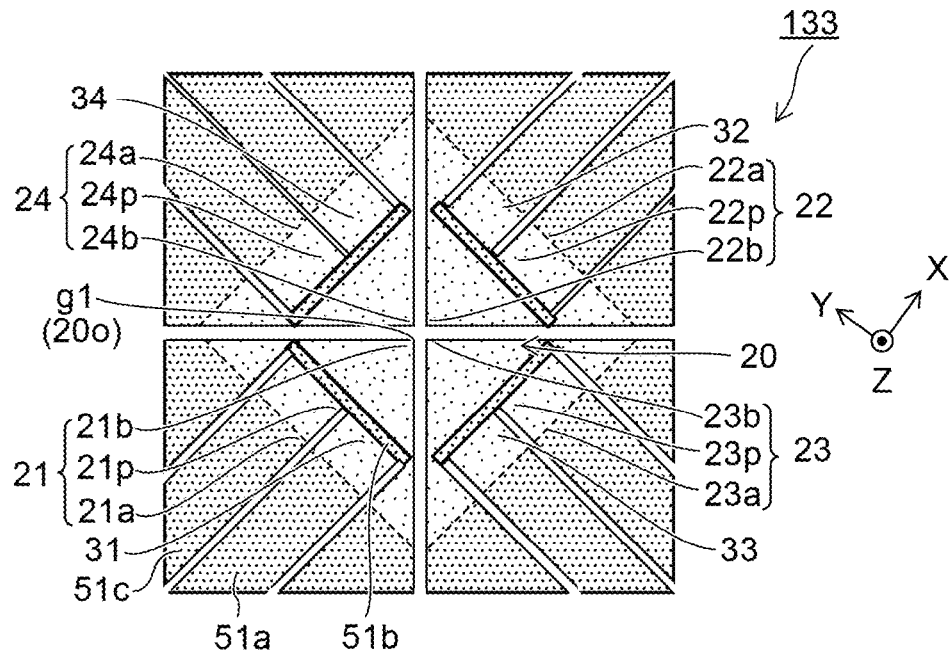
FIG. 31 is a schematic plan view showing other sensors according to the first embodiment.
Figure 32:
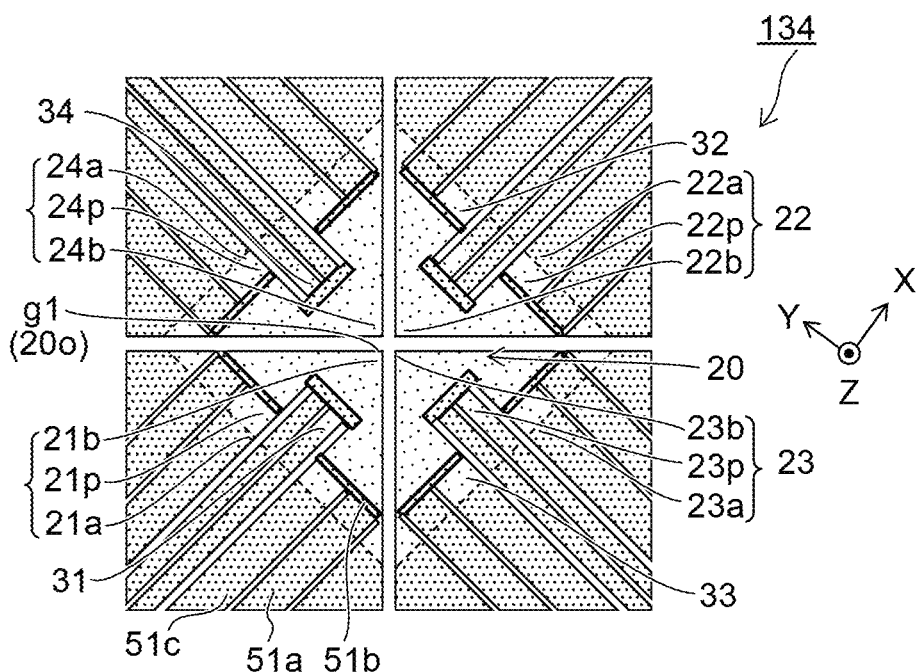
FIG. 32 is a schematic plan view showing other sensors according to the first embodiment.
Figure 33:
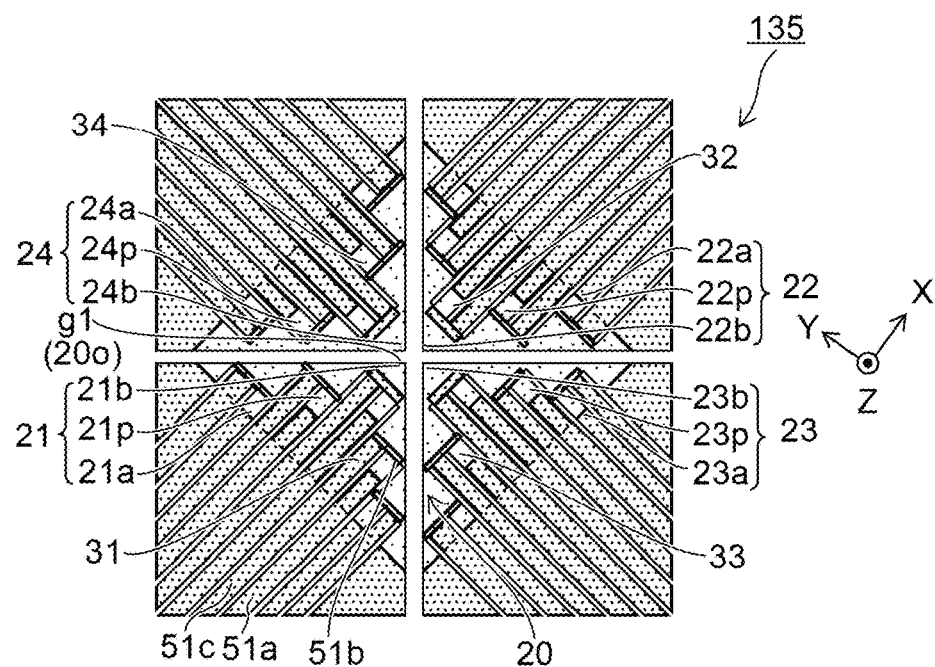
FIG. 33 is a schematic plan view showing other sensors according to the first embodiment.

FIG. 28A and FIG. 28B are schematic perspective views illustrating other sensors according to the first embodiment.

In a sensor 128a as illustrated in FIG. 28A, the first sensing element 31 includes multiple portions. The multiple portions are connected in a zigzag configuration. In such a configuration, the number of sensing elements that are provided in a limited region inside the film unit 20 can be increased. The total surface area of the sensing elements can be increased. Thereby, for example, the fluctuation can be suppressed.

In a sensor 128b as shown in FIG. 28B, sensing elements are provided on surfaces on two sides of the film unit 20. In other words, the film unit 20 has the first surface 20fa and the second surface 20fb. The first surface 20fa is the surface on the liquid 45 side (referring to FIG. 1B). The second surface 20fb is the surface on the side opposite to the first surface 20fa. The sensing unit 30 includes the first sensing element 31 provided on the first surface 20fa of the first portion 21p, and the second sensing element 31a provided on the second surface 20fb of the first portion 21p.

At least one of the first sensing element 31 or the second sensing element 31a has at least one of a change of a resistance accompanying the displacement of the first portion 21p, a change of an electrostatic capacitance accompanying the displacement of the first portion 21p, or a change of a voltage of piezoelectricity accompanying the displacement of the first portion 21p.

FIG. 29 to FIG. 34 are schematic plan views illustrating other sensors according to the first embodiment.

These drawings illustrate the film unit 20 and the electrodes.

In sensors 131 to 135 according to the embodiment as illustrated in FIG. 29 to FIG. 33, the first to fourth regions 21 to 24 are provided. A sensing element is provided in each region. For example, in these sensors, the orientations of the currents intersect (e.g., are orthogonal to) each other between the multiple sensing elements. For example, the sensing elements are arranged in the directions in which the change of the piezoresistance becomes large. The change of the resistance can be utilized efficiently.

Figure 34:
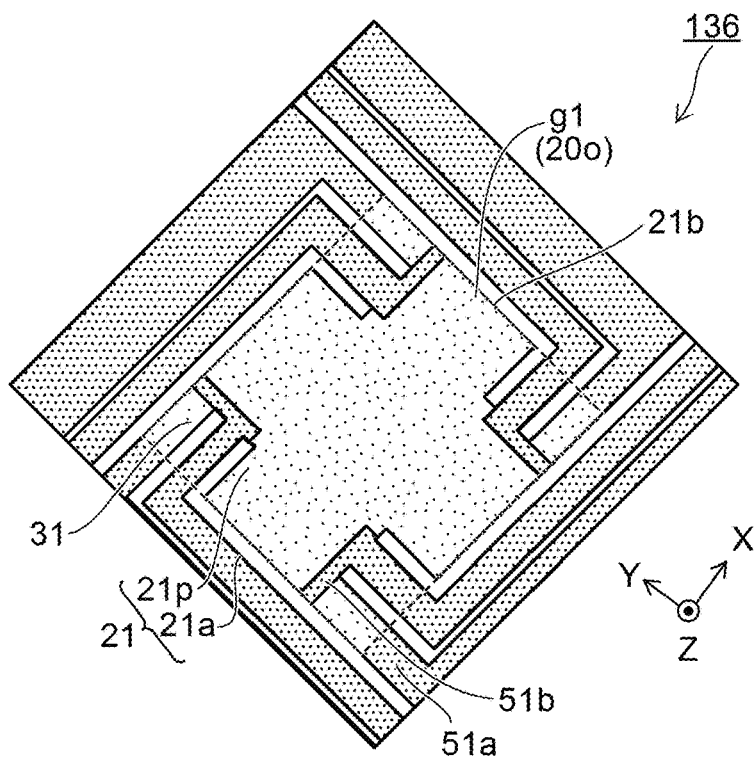
FIG. 34 is a schematic plan view showing other sensors according to the first embodiment.

In a sensor 136 according to the embodiment as illustrated in FIG. 34, four combinations of an electrode set (the first electrode 51a and the second electrode 51b) are provided in the film unit 20. The electrode sets have configurations having point symmetry with each other.

In the sensors 131 to 136 as well, highly-sensitive sensing can be performed.

Second Embodiment

FIG. 35A and FIG. 35B are schematic cross-sectional views illustrating sensors according to a second embodiment.

The sensing elements are not shown in these drawings.

In sensors 140 and 141 according to the embodiment as shown in FIG. 35A and FIG. 35B, the lower surface of the liquid 45 has a lens configuration.

In other words, the liquid 45 has a second liquid surface 45b and a surface (a first liquid surface 45a) on the film unit 20 side. The second liquid surface 45b is the surface on the side opposite to the first liquid surface 45a.

The second liquid surface 45b includes a portion 45p that is tilted. The tilted portion 45p is tilted with respect to the X-Y plane (i.e., a plane perpendicular to the Z-axis direction from the container 40 toward the supporter 10).

In the sensor 140, the film unit 20 further includes the second region 22 in addition to the first region 21. The second region 22 includes the second end portion 22a supported by the supporter 10, and the second opposite end 22b on the side opposite to the second end portion 22a. The opening 20o is provided between the first end portion 21a and the second end portion 22a. In the example, the opening 20o is provided between the first opposite end 21b and the second opposite end 22b.

The second liquid surface 45b has a first front surface 47a on the first end portion 21a side, and a second front surface 47b on the second end portion 22a side. The tilt direction of the first front surface 47a with respect to the X-Y plane is reverse to the tilt direction of the second front surface 47b with respect to the X-Y plane.

By such a tilt, the propagation direction of the sound wave 80 can be changed. In the sensors 140 and 141, the propagation direction of the sound wave 80 can be changed by providing the tilted portion 45p in the second liquid surface 45b of the liquid 45.

FIG. 36 is a schematic view illustrating a characteristic of the sensor according to the second embodiment.

FIG. 36 illustrates a characteristic of a sound wave propagating through different media.

As shown in FIG. 36, the speed of sound in a first medium m1 is a first speed of sound c1. The speed of sound in a second medium m2 is a second speed of sound c2. The angle of the propagation direction of the sound wave in the first medium m1 is taken as a first angle $\theta 1$. The first angle $\theta 1$ is the angle between a direction perpendicular to the interface between the first medium m1 and the second medium m2 and the propagation direction of the sound wave in the first medium m1. The angle of the propagation direction of the sound wave in the second medium m2 is taken as a second angle $\theta 2$. The second angle $\theta 2$ is the angle between a direction perpendicular to the interface between the first medium m1 and the second medium m2 and the propagation direction of the sound wave in the second medium m2. In such a case, for example, the relationship $\sin(\theta 1)/\sin(\theta 2)=c2/c1$ is satisfied. The refraction of the sound wave at the interface occurs due to the tilt of the interface of the liquid. The propagation direction of the sound wave can be changed. In other words, an acoustic lens can be formed.

For example, in the sensors 140 and 141, the material properties of the wall 40w and the material properties of the liquid 45 are selected appropriately. It becomes possible to refract the traveling wave between the wall 40w and the liquid 45. For example, the planar dimensions of the liquid 45 are set to be large; and the refracted traveling wave is caused to travel toward the center of the sensor. A greater vibration of the front surface of the liquid 45 can be caused. For example, the displacement Ds of the film unit 20 (e.g., the cantilever) can be increased. A highly-sensitive sensor can be provided.

In the embodiment, the vibrations are concentrated in the sensing unit 30 by utilizing the difference of the physical properties between the container 40 (the wall 40w) and the liquid 45. In other words, the traveling wave is refracted between the container 40 and the liquid 45; and the traveling wave is concentrated at the vibrating body mounted at the front surface of the liquid 45. Thereby, the sensitivity of the sensing is increased.

In the sensors 140 and 141, the container 40 includes the wall 40w and a thin film portion 41. The thin film portion 41 is disposed between the wall 40w and the liquid 45. The wall 40w includes, for example, PDMS. The thin film portion 41 includes, for example, a paraxylene polymer. The thin film portion 41 may be omitted.

Third Embodiment

Figure 37A:
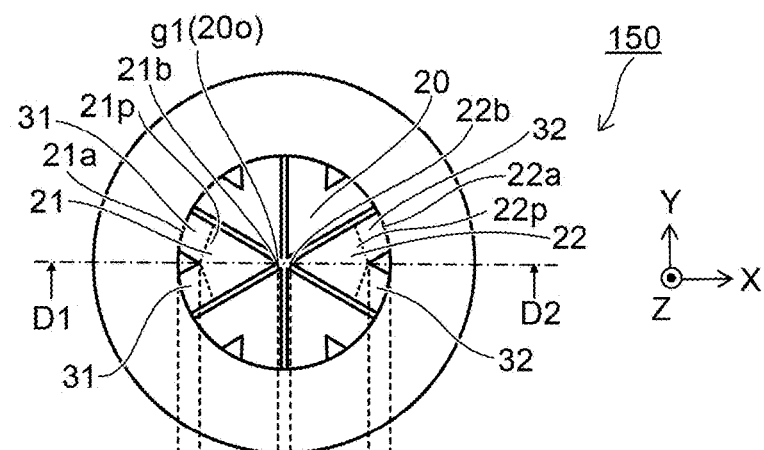
FIG. 37A and FIG. 37B are schematic views showing a sensor according to a third embodiment.
Figure 37B:
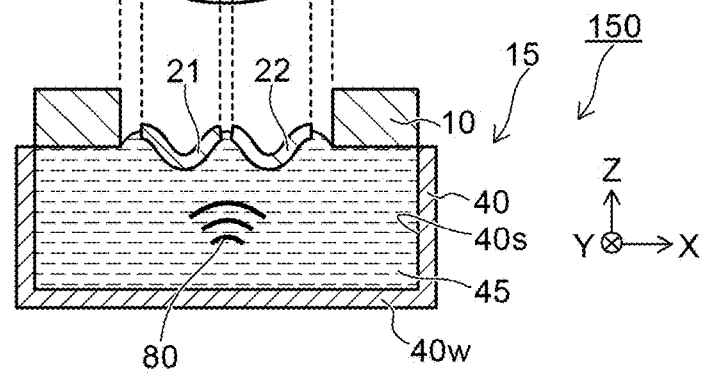

FIG. 37A and FIG. 37B are schematic views illustrating a sensor according to a third embodiment.

FIG. 37A is a schematic plan view. FIG. 37B is a line D1-D2 cross-sectional view of FIG. 37A.

As shown in FIG. 37A and FIG. 37B, the sensor 150 according to the embodiment also includes the structure body 15, the container 40, and the liquid 45. For example, the first region 21 and the second region 22 are provided in the film unit 20. The first sensing element 31 is provided in the first region 21. The second sensing element 32 is provided in the second region 22.

For example, the first sensing element 31 is provided at the first portion 21p of the first region 21. The distance from the first end portion 21a of the first portion 21p is, for example, not more than about ¼ of the wavelength of the surface wave occurring in the front surface in the opening 20o.

For example, to increase the sensitivity in a designated frequency domain in the sensor 150, the region where the sensing element is provided is set according to the wavelength of the surface wave of the liquid 45. Thereby, one of tensile strain or compressive strain can be applied to the sensing element. In the example, the first sensing element 31 is disposed in the region of the cantilever configuration at the vicinity of the first end portion 21a of the first region 21. The wavelength of the surface wave occurring in the front surface in the opening 20o is taken as λ. For example, the first sensing element 31 is disposed so that the distance from the first end portion 21a is within the range of λ/4.

In the case where an object having a film-like configuration deforms in a sinusoidal configuration, the direction of the strain occurring in the front surface inside a region of λ/2 can be limited to one of tension or compression by appropriately selecting the position, where a is the wavelength of the sine wave. In the case where the end portion 21a is a fixed end, it is desirable to dispose the first sensing element 31 within the range of λ/4 because the direction of the strain switches at a position λ/4 away from the end portion.

Thereby, one of tensile strain or compressive strain can be applied to the first sensing element 31. It becomes possible to obtain higher sensitivity.

As shown in FIG. 7 to FIG. 11, the wavelength of the surface wave occurring in the front surface changes according to the frequency of the sound wave 80. For example, the relationship between the frequency of the sound wave 80 and the wavelength λ of the surface wave is verified by experiments and/or simulations beforehand. For example, the first sensing element 31 is disposed in the region of λ/4 by using the wavelength λ of the surface wave occurring at the frequency at which the sensitivity is to be increased. Thereby, higher sensitivity is obtained in the intended frequency band.

For example, the size of the first sensing element 31 is set to be about λ/4. For example, the first sensing element 31 includes the crystal layer 13a of silicon including the impurity, the first electrode 51a connected to one portion of the crystal layer 13a, and the second electrode 51b connected to one other portion of the crystal layer 13a (referring to FIG. 1B, etc.). Also, the displacement Ds of the liquid 45 includes a surface wave including the first wavelength λ. In such a case, the distance (the distance along the X-Y plane) between the first electrode 51a and the second electrode 51b is not more than about ¼ of the first wavelength λ. In other words, the distance is not more than 0.28 times the first wavelength λ. The distance may be, for example, not less than 0.22 times the first wavelength λ. Thereby, an effective strain can be caused to occur in the first sensing element 31.

Figure 38A:
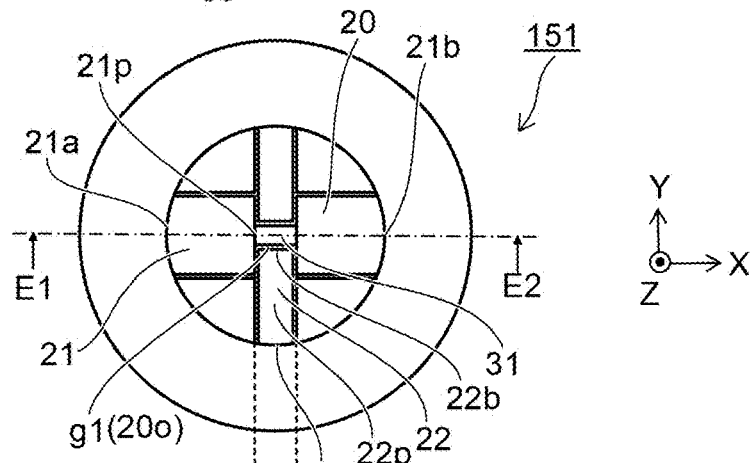
FIG. 38A and FIG. 38B are schematic views showing another sensor according to the third embodiment.
Figure 38B:
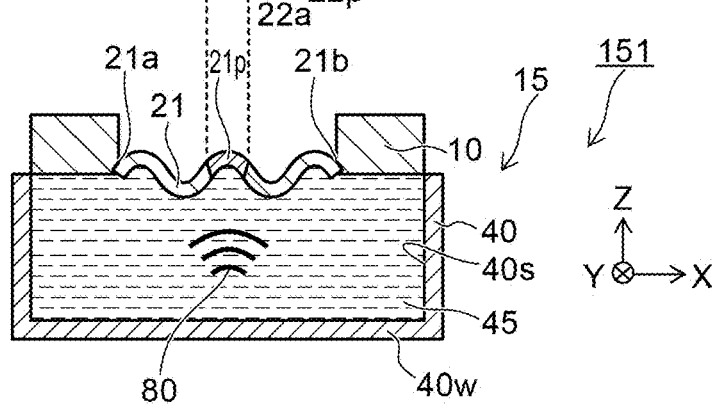

FIG. 38A and FIG. 38B are schematic views illustrating another sensor according to the third embodiment.

FIG. 38A is a schematic plan view. FIG. 38B is a line E1-E2 cross-sectional view of FIG. 38A.

As shown in FIG. 38A and FIG. 38B, the sensor 151 according to the embodiment also includes the structure body 15, the container 40, and the liquid 45. For example, the first region 21 and the second region 22 are provided in the film unit 20. The first sensing element 31 is provided in the first region 21. The first region 21 has, for example, a two-end-supported configuration.

In such a case, for example, the size of the sensing element (the first sensing element 31) is set to about ½ of the wavelength λ of the surface wave occurring in the front surface in the opening 20o. In FIG. 38A and FIG. 38B, the two ends of the first sensing element 31 are not used as fixed ends because the first sensing element 31 is disposed at a location distal to the end portion 21a. By selecting the position of the anti-node of the surface wave to be the center of the first sensing element 31, the strain occurs in a uniform direction inside the region of λ/2.

For example, in the case where the first electrode 51a and the second electrode 51b are provided in the first sensing element 31, the distance (the distance along the X-Y plane) between the first electrode 51a and the second electrode 51b is not more than about ½ of the first wavelength λ. In other words, the distance is not more than 0.6 times the first wavelength λ. The distance may be, for example, not less than 0.4 times the first wavelength h. Thereby, an effective strain can be caused to occur in the first sensing element 31. For example, strain occurs in a uniform direction in the film unit 20. For example, the relationship between the frequency of the sound wave 80 and the wavelength λ of the surface wave is verified by experiments and/or simulations beforehand. For example, the first sensing element 31 is disposed in the region of λ/2 by using the wavelength λ of the surface wave occurring at the frequency at which the sensitivity is to be increased. Thereby, higher sensitivity is obtained in the intended frequency band.

Fourth Embodiment

Figures 39A, 39B:
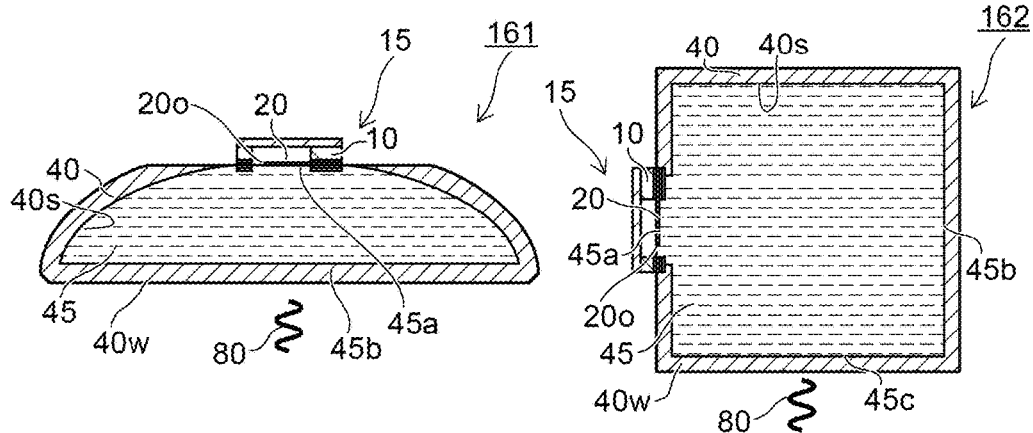
FIG. 39A and FIG. 39B are schematic cross-sectional views showing sensors according to a fourth embodiment.

FIG. 39A and FIG. 39B are schematic cross-sectional views illustrating sensors according to a fourth embodiment.

In a sensor 161 according to the embodiment as shown in FIG. 39A, the sound wave 80 enters from the second liquid surface 45b of the liquid 45. In the example, the first liquid surface 45a has a curved configuration. The first liquid surface 45a may have a planar configuration.

In a sensor 162 according to the embodiment as shown in FIG. 39B, the sound wave 80 is incident on a side surface of the liquid 45. In other words, the liquid 45 has a third liquid surface 45c in addition to the first liquid surface 45a and the second liquid surface 45b. The third liquid surface 45c intersects the first liquid surface 45a and further intersects the second liquid surface 45b. Thus, in the embodiment, the direction of the sound wave 80 incident on the liquid 45 is arbitrary.

In the embodiment, for example, the film unit 20 (and the opening 20o of the film unit 20) are substantially perpendicular to the propagation direction of the sound wave 80. Or, the film unit 20 (and the opening 20o of the film unit 20) may be substantially parallel to the propagation direction of the sound wave 80.

Figure 40:
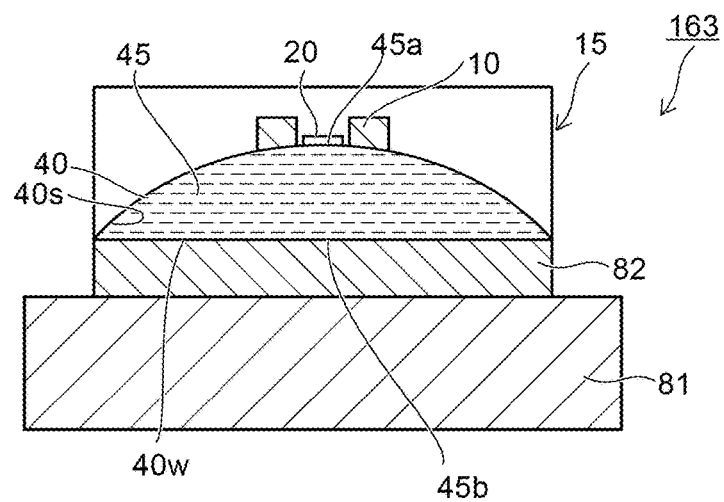
FIG. 40 is a schematic cross-sectional view showing another sensor according to the fourth embodiment.

FIG. 40 is a schematic cross-sectional view illustrating another sensor according to the fourth embodiment.

As shown in FIG. 40, an intermediate layer 82 is provided in the sensor 163 according to the embodiment. At least one portion of the wall 40w of the container 40 is disposed between the intermediate layer 82 and the liquid 45. For example, the intermediate layer 82 is disposed between the measurement object 81 and the wall 40w when using the sensor 163.

For example, the acoustic impedance of the intermediate layer 82 is between the impedance of the measurement object 81 and the acoustic impedance of the wall 40w. For example, the intermediate layer 82 may include a magnet.

For example, the intermediate layer 82 contacts the measurement object 81. For example, the intermediate layer 82 contacts the wall 40w.

For example, the intermediate layer 82 matches the acoustic impedance between the measurement object 81 and the wall 40w. For example, the material of the intermediate layer 82 and the configuration of the first space 40s in which the liquid 45 is contained are designed appropriately. Thereby, for example, the matching of the acoustic impedance and the control of the propagation direction of the sound wave by an acoustic lens can be performed.

In the embodiment, for example, the natural frequency of the liquid 45 can be set to substantially an integer multiple (the integer being an integer not less than 1) times the natural frequency of the container 40. For example, the natural frequency of the liquid 45 is not less than 0.8 times and not more than 1.2 times the integer multiple of the natural frequency of the container 40. For example, the thickness of the liquid 45 is set to be markedly thin compared to the thickness of the container 40. The characteristic vibration of the container 40 becomes substantially dominant; and the effects of the characteristic vibration of the liquid 45 become small. Such a configuration also can be realized artificially. Thereby, the vibrations in the container 40 are applied efficiently to the liquid 45.

Fifth Embodiment

FIG. 41 is a schematic cross-sectional view illustrating a sensor according to a fifth embodiment.

As shown in FIG. 41, the structure body 15, the container, and the liquid 45 are provided in the sensor 170 according to the embodiment as well. In the example, the sensing unit 30 senses the deformation of the film unit 20 by utilizing light.

In other words, the sensing unit 30 includes a light source 71 that emits light 74, and a sensing element 73 that senses the light reflected by the first region 21 of the film unit 20. The light source 71 includes, for example, a laser. In the example, a beam splitter 72 is provided in the optical path of the light 74. The light 74 that is emitted from the light source 71 passes through the beam splitter 72 and is incident on the film unit 20. The propagation direction of the light reflected by the film unit 20 is changed by the beam splitter 72. The light that is changed is incident on the sensing element 73. Thereby, the displacement Ds of the film unit 20 can be sensed optically.

In the embodiment, for example, the displacement Ds of the film unit 20 is sensed optically by the sensing unit 30. In the embodiment, the sensing of the film unit 20 can be performed by any method. For example, the sensing unit 30 may have at least one of the change of the resistance occurring with the displacement of the first portion 21p, the change of the voltage of the piezoelectricity occurring with the displacement of the first portion 21p, or the change of the electrostatic capacitance occurring with the displacement of the first portion 21p.

In the sensor according to the embodiment, for example, the sound wave 80 that propagates through the measurement object 81 is sensed via the liquid 45. The frequency of the sound wave 80 is, for example, not less than 10 kHz and not more than 3 MHz. For example, the liquid 45 is constrained by the wall 40w. The liquid 45 has a free interface in the opening 20o provided in the film unit 20. For example, the film unit 20 deforms due to the vibrations of the liquid 45. The deformation of the film unit 20 is sensed by the sensing unit 30 (e.g., the first sensing element 31, etc.).

In the embodiment, a reflective film or a transmitting film for the sound wave 80 is provided at the surface where the liquid 45 is constrained.

It may be possible to control matching and mismatching with the sound wave 80. The volume, thickness, and material of the liquid 45 are designed to match the sound wave 80 to be sensed.

Sixth Embodiment

FIG. 42A and FIG. 42B are schematic views illustrating a sensor according to a sixth embodiment.

FIG. 42A is a schematic plan view. FIG. 42B is a line E1-E2 cross-sectional view of FIG. 42A.

As shown in FIG. 42A and FIG. 42B, the structure body 15, the container 40, and the liquid 45 are provided in the sensor 201 according to the embodiment as well. For example, the first to seventh regions 21 to 27 are provided in the film unit 20.

The first sensing element 31 is provided in the first region 21. For example, the first region 21 has a two-end-supported configuration. In other words, the first region 21 includes the first end portion 21a, the first portion 21p that is displaceable, and the first opposite end 21b on the side opposite to the first end portion 21a. The first portion 21p is provided between the first end portion 21a and the first opposite end 21b. The first end portion 21a is connected to and supported by a first portion of the supporter 10. The first opposite end 21b is connected to and supported by another portion (a second portion) of the supporter 10. In the example, the width of the first portion 21p in the Y-axis direction is narrower than the width of the first end portion 21a in the Y-axis direction and narrower than the width of the first opposite end 21b in the Y-axis direction. In the example, the Y-axis direction is a direction intersecting (orthogonal to)

the direction from the first end portion 21a toward the first portion 21p. The Y-axis direction is a direction intersecting (orthogonal to) the direction from the first end portion 21a toward the first opposite end 21b. Also, the Y-axis direction is perpendicular to the Z-axis direction from the container 40 toward the supporter 10. Because the width in the Y-axis direction of the first portion 21p is narrow, the first portion 21p deforms easily. High sensitivity becomes easy to obtain.

The first portion 21p of the first region 21 is disposed between the second region 22 and the third region 23. The direction from the second region 22 toward the third region 23 intersects (e.g., is orthogonal to) the direction from the first end portion 21a toward the first opposite end 21b. A gap (the opening 20o) is provided between the second region 22 and the first portion 21p. A gap (the opening 20o) is provided between the third region 23 and the first portion 21p. By providing the gaps, the first portion 21p deforms easily.

The direction from the fourth region 24 toward the fifth region 25 is aligned with the direction from the first end portion 21a toward the first opposite end 21b. The direction from the sixth region 26 toward the seventh region 27 is aligned with the direction from the first end portion 21a toward the first opposite end 21b. The second region 22 is provided between the fourth region 24 and the fifth region 25. The third region 23 is provided between the sixth region 26 and the seventh region 27. The first region 21 includes a portion between the first end portion 21a and the first portion 21p. At least one portion of the portion between the first end portion 21a and the first portion 21p is disposed between the fourth region 24 and the sixth region 26. The first region 21 includes a portion between the first opposite end 21b and the first portion 21p. At least one portion of the portion between the first opposite end 21b and the first portion 21p is disposed between the fifth region 25 and the seventh region 27.

The gaps are provided between the multiple regions (between the mutually-adjacent regions). Thereby, the multiple regions of the film unit 20 each deform easily. The deformation of the film unit 20 follows the surface wave 46 of the liquid 45 easily. If it is difficult for the film unit 20 to deform, the surface wave 46 is suppressed by the film unit 20; and it becomes difficult for the surface wave 46 based on the sound wave 80 from the outside to be formed. By the film unit 20 deforming easily, the surface wave 46 based on the sound wave 80 from the outside is formed efficiently. Thereby, high sensitivity is obtained.

By providing the gaps between the multiple regions (between the mutually-adjacent regions), one portion of the liquid 45 may exude slightly from the first space 40s in the gaps. However, due to the surface tension of the liquid 45, the liquid 45 returns to the original state and is contained in the first space 40s.

It is favorable for the width of the gap between the multiple regions (the length along the direction connecting the adjacent regions to each other, i.e., the width of the opening 20o) to be, for example, not less than 10 nm and not more than 100 µm. When the gap is excessively small, it becomes difficult to pattern the film unit; and it becomes difficult for the film unit to deform. When the gap is excessively large, the liquid 45 leaks out. It is more favorable for the width of the gap between the multiple regions (the width of the opening 20o) to be, for example, not less than 1 µm and not more than 10 µm. Thereby, the leakage of the liquid 45 can be suppressed with higher certainty.

The width of the gap (the width of the opening 20o) may be determined based on at least one of the surface tension (the surface energy) of the liquid 45 or the surface tension (the surface energy) of the film unit 20. In the case where silicone oil is used as the liquid 45, the surface energy (25° C.) of the liquid 45 is not less than 30 dyne/cm and not more than 36 dyne/cm (e.g., not less than 34 dyne/cm and not more than 35 dyne/cm). For example, methyl phenyl silicone oil, etc., can be used as the silicone oil. In the case where water is used as the liquid 45, the surface energy (25° C.) of the liquid 45 is about 72.0 dyne/cm.

In the embodiment, based on experimental results, the width of the gap (the width of the opening 20o) (units: m) is set to be, for example, $\gamma c/10^5$ or less, where the surface energy of the liquid 45 is $\gamma c$ (dyne/cm). Thereby, for example, the leakage of the liquid 45 can be suppressed practically. For example, when the surface energy $\gamma c$ of the liquid 45 is 33.9 dyne/cm, the width of the gap (the width of the opening 20o) is set to be not more than 33.9 (dyne/cm)/$10^5$. In other words, the width of the gap (the width of the opening 20o) is set to be not more than $339 \times 10^{-6}$ m (i.e., 339 µm). The width of the gap (the width of the opening 20o) is greater than zero.

The width of the gap may not be constant. For example, the width of the gap positioned at the central portion inside the film unit 20 may be different from the width of the gap positioned at the peripheral portion. For example, the width of the gap positioned at the central portion is wider than the width of the gap positioned at the peripheral portion. Thereby, for example, because the film region that covers the liquid surface is narrow at the central portion, it is expected that the force of the film constraining the liquid surface will become small. As a result, the wavelength of the surface wave at some frequency becomes long in this region. An effect is expected in which the frequency domain where the sensitivity is high shifts downward.

For example, the width of the gap positioned at the central portion may be narrower than the width of the gap positioned at the peripheral portion. Thereby, for example, because the film region that covers the liquid surface is wide at the central portion, it is expected that the force of the film constraining the liquid surface will become large. As a result, the wavelength of the surface wave at some frequency becomes short in this region. An effect is expected in which the frequency domain where the sensitivity is high shifts upward. The width of the gap may be changed according to the surface wave 46 that is estimated to occur. For example, the width of the gap may be changed according to the position of the anti-node of the surface wave 46, etc.

In the sensor 201, the first sensing element 31 is provided in the first portion 21p of the first region 21. Further, the second sensing element 32 is provided in the second region 22; and the third sensing element 33 is provided in the third region 23.

In the example, the second sensing element 32 is provided at the vicinity of the second end portion 22a of the second region 22. In other words, the distance between the second end portion 22a and the second sensing element 32 is shorter than the distance between the second sensing element 32 and the second opposite end 22b of the second region 22. The third sensing element 33 is provided at the vicinity of the third end portion 23a of the third region 23. In other words, the distance between the third end portion 23a and the third sensing element 33 is shorter than the distance between the third sensing element 33 and the third opposite end 23b of the third region 23.

The distance between the second sensing element 32 and the center position 20c of the film unit 20 is different from the distance between the center position 20c and the first sensing element 31. The distance between the third sensing element 33 and the center position 20c of the film unit 20 is different from the distance between the center position 20c and the first sensing element 31. Specifically, the second sensing element 32 and the third sensing element 33 each are provided at the peripheral portion of the film unit 20. The first sensing element 31 is provided at the central portion of the film unit 20.

The frequency of the surface wave 46 at which the large amplitude occurs is different between the central portion and the peripheral portion of the film unit 20. For example, the frequencies in the regions corresponding to the second sensing element 32 and the third sensing element 33 are lower than the frequency in the region corresponding to the first sensing element 31. For example, waves of different frequencies can be sensed with high sensitivity.

In the sensor 201, the first sensing element 31 is provided at the fixed beam portion of the central portion; and the second sensing element 32 and the third sensing element 33 are provided at the cantilever portions. The frequencies of high sensitivity for the fixed beam portion of the central portion are different from the frequencies of high sensitivity for the cantilever portions. In the sensor 201, sensors are obtained in which the response of one sensor is for frequencies in a wide range. For example, the rigidity for bending is high for the fixed beam portion compared to the cantilever portions (the cantilever beam portions). In the case of the same thickness, the highly-sensitive frequencies of the fixed beam portion are higher than the highly-sensitive frequencies of the cantilever portions. For example, for the fixed beam portion, the sound waves (the vibrations) in the high frequency band of 100 kHz or more are sensed by the fixed beam portion. On the other hand, the sound waves (the vibrations) in the low frequency band of less than 100 kHz are sensed by the cantilever portions. Band separation becomes possible.

For example, the fixed beam portion and the cantilever portions are formed by a silicon process. Sensing regions are disposed in multiple regions inside one sensor. The interconnects and/or preamplifier units can be used commonly. Downsizing becomes possible. Compared to the case where multiple sensors are used, size reduction is possible; and the cost also can be reduced.

Figure 43:
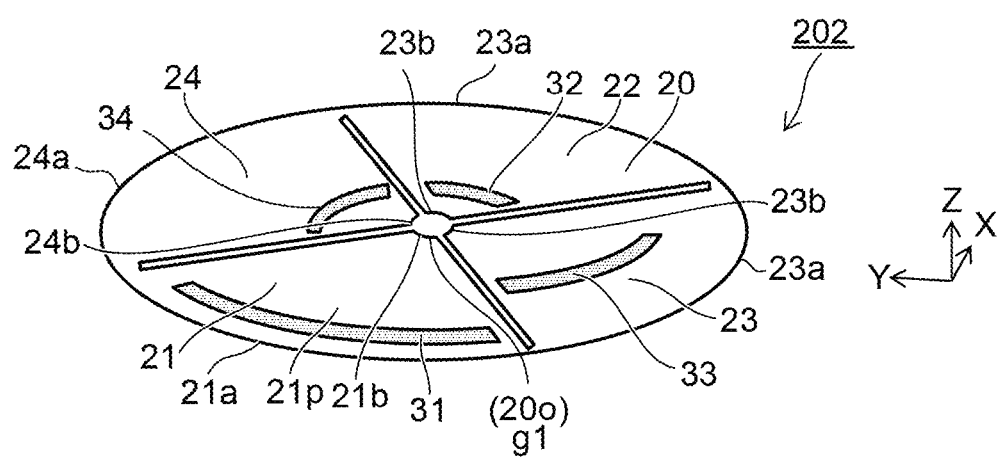
FIG. 43 is a schematic perspective view showing another sensor according to the sixth embodiment.

FIG. 43 is a schematic perspective view illustrating another sensor according to the sixth embodiment.

As shown in FIG. 43, the structure body 15, the container 40, and the liquid 45 are provided in the sensor 202 according to the embodiment as well. For example, the first to fourth regions 21 to 24 are provided in the film unit 20. The first to fourth sensing elements 31 to 34 are provided respectively in the first to fourth regions 21 to 24.

The distances from the center of the film unit 20 to the first to fourth sensing elements 31 to 34 are different from each other.

The ratio (a first ratio) of the distance between the first sensing element 31 and the first end portion 21a to the distance between the first sensing element 31 and the first opposite end 21b is low.

The ratio (a fourth ratio) of the distance between the fourth sensing element 34 and the fourth end portion 24a to the distance between the fourth sensing element 34 and the fourth opposite end 24b is high.

The ratio (a second ratio) of the distance between the second sensing element 32 and the second end portion 22a to the distance between the second sensing element 32 and the second opposite end 22b is between the first ratio and the fourth ratio.

The ratio (a third ratio) of the distance between the third sensing element 33 and the third end portion 23a to the distance between the third sensing element 33 and the third opposite end 23b is between the second ratio and the fourth ratio.

Thus, the positions of the multiple sensing elements (the distances from the center of the film unit 20) are different from each other. Thereby, each of the waves can be sensed with high sensitivity.

In the sensor 202, the multiple sensing elements are provided respectively at the four cantilever portions (the regions of the film unit 20). The positions in the direction from the center of the film unit 20 toward the outside for the multiple sensing elements are different from each other. The cantilever portions vibrate in configurations along the surface wave 46 occurring at the front surface of the liquid 45. In the case where the configuration of the front surface of the liquid 45 is a circular configuration, the surface wave 46 is a standing wave having a concentric circular configuration. The wave number increases as the frequency of the standing wave increases. The positions of the sensing elements are arranged to be shifted in the radial direction for each of the multiple cantilever portions. The frequencies at which the position of the anti-node of the standing wave and the position of the sensing element match are different from each other. The frequency domains where the sensitivity is high are different between the multiple cantilever portions. High sensitivity is obtained by one sensor in multiple frequency domains.

In a sensor 203, the sensor 127a, the sensor 127b, etc., the positions of the multiple sensing elements (e.g., the distances from the center of the film unit 20) are different from each other. By such a configuration, the phase difference of the surface wave 46 can be sensed by multiple sensing elements. For example, the difference between the resistance corresponding to tension of the surface wave 46 and the resistance corresponding to compression of the surface wave 46 is sensed by multiple sensing elements.

For example, compared to the case where sensing elements are disposed on the entire surface of the cantilever, because the sensing elements in the regions other than the positions of the anti-nodes are excluded, a sensitivity increase corresponding to the ratio of the surface area of the position of the anti-nodes of the surface wave occurring at some frequency to the surface area of the other regions is expected.

FIG. 44A to FIG. 44E are schematic views illustrating another sensor according to the sixth embodiment.

FIG. 44A is a schematic plan view. FIG. 44B is a line E1-E2 cross-sectional view of FIG. 44A. FIG. 44C to FIG. 44E are cross-sectional views corresponding to line E1-E2 of FIG. 44A for other examples.

As shown in FIG. 44A and FIG. 44B, the structure body 15, the container 40, and the liquid 45 are included in the sensor 203 according to the embodiment as well. For example, the first to seventh regions 21 to 27 are provided in the film unit 20. The first sensing element 31 is provided in the first portion 21p of the first region 21 of the film unit 20.

In the examples, the thicknesses of the film unit 20 are different in the plane. In other words, the thickness (the length aligned with the Z-axis direction) of the first portion 21p of the first region 21 is thinner than the thickness of the first end portion 21a and thinner than the thickness of the first opposite end 21b. Thereby, the first portion 21p deforms easily. The strain becomes large at the first portion 21p. For example, a three-dimensional notch is formed easily.

In the case where the entire film unit 20 is set to be thin, for example, the strength of the film unit 20 may decrease and the reliability may decrease. Also, the patterning may be difficult.

Conversely, as in the examples, the first portion 21p can be made to deform easily by setting the thickness of the first portion 21p to be thinner than the other portions. For example, the tensile strain can be large. For example, the bending strain can be large. Then, a high strength can be maintained; and high productivity can be maintained.

For example, the thickness of the first portion 21p of the first region 21 is not less than 0.1 times and not more than 0.8 times (e.g., not more than 0.5 times) the thickness of the first end portion 21a. For tensile deformation, the rigidity is proportional to the thickness. By setting the thickness of the first portion 21p of the first region 21 to be 0.5 times the thickness of the first end portion 21a, twice the strain can be caused to occur using the same force. For bending deformation, the rigidity is proportional to the third power of the thickness. By setting the thickness of the first portion 21p of the first region 21 to be about 0.8 times the thickness of the first end portion 21a, twice the strain can be caused to occur using the same force. By setting the thickness of the first portion 21p of the first region 21 to be thin, the resistance value increases. By setting the thicknesses such as those recited above for the frequencies of the regions where bending deformation is to be caused to occur in the first portion 21p, the sensitivity is increased further because the degree of the decrease of the rigidity for tension is larger than the degree of the decrease of the rigidity for bending.

For example, the thickness of the first portion 21p of the first region 21 is not less than 10 nm and not less than 240 nm. For example, the thickness may be not less than 10 nm and not more than 150 nm. On the other hand, the thickness of the first end portion 21a is not less than 300 nm and not more than 1000 nm. For example, when the thickness of the first end portion 21a is not less than 280 nm and not more than 320 nm, the thickness of the first portion 21p of the first region 21 is 240 nm or less (or 150 nm or less).

As illustrated in FIG. 44C, the thickness of the first region 21 (the film unit 20) may change between the regions of the first end portion 21a and the first portion 21p. The thickness of the first region 21 (the film unit 20) may change between the regions of the first opposite end 21b and the first portion 21p.

As illustrated in FIG. 44D, the thickness of the first region 21 (the film unit 20) may change at the boundary between the first end portion 21a and the first portion 21p. The thickness of the first region 21 (the film unit 20) may change at the boundary between the first opposite end 21b and the first portion 21p.

As illustrated in FIG. 44E, the change of the thickness of the first region 21 (the film unit 20) may be continuous. The thickness may have a step configuration. The number of steps of the change of the thickness may be one or may be multiple.

In the sensor 203, vibrations such as AE, etc., are sensed as the size of the strain occurring in the first sensing element 31. When the energy of the vibration is applied, a larger strain is caused to occur. Thereby, the sensitivity as a sensor is higher. By setting the sensing element portion to be thin, a larger strain is obtained. For example, the thickness of the film unit 20 can be modified by controlling the process conditions of the etching, etc.

FIG. 45 is a schematic perspective view illustrating another sensor according to the sixth embodiment.

In the sensor 204 as illustrated in FIG. 45, the first to fourth sensing elements 31 to 34 are provided respectively in the first to fourth regions 21 to 24 of the film unit 20.

The first to fourth sensing elements 31 to 34 each include multiple portions. The multiple portions are connected in a zigzag configuration. The multiple portions are arranged along a side (e.g., the side of the first end portion 21a) of the fixed end of the film unit 20. The multiple portions each extend along a direction substantially perpendicular to the side of the fixed end. In such a configuration, the number of sensing elements provided in a limited region inside the film unit 20 can be increased. The total surface area of the sensing elements can be increased. Thereby, for example, the fluctuation can be suppressed.

Seventh Embodiment

FIG. 46A and FIG. 46B are schematic views illustrating a sensor according to a seventh embodiment.

FIG. 46A is a schematic plan view. FIG. 46B is a line E1-E2 cross-sectional view of FIG. 46A.

As shown in FIG. 46A and FIG. 46B, the structure body 15, the container 40, and the liquid 45 are provided in the sensor 210 according to the embodiment as well. For example, the first to sixth regions 21 to 26 are provided in the film unit 20.

The first sensing element 31 is provided in the first region 21. The first sensing element 31 includes a current path 31el. The current path 31el is substantially aligned with a crystal orientation Dc of the film unit 20.

In the example, the current path 31el has a zigzag configuration. In other words, the current path 31el includes multiple extension portions, and connectors that connect the ends of the mutually-adjacent multiple extension portions. The extension direction of the extension portions are aligned with the crystal orientation Dc.

The crystal orientation Dc is, for example, one of the <110> direction or the <100> direction of the silicon. For example, the film unit 20 includes an n-type silicon crystal; and the direction of the current path 31el (the extension direction of the extension portions) is aligned with the <100> direction. On the other hand, for example, the film unit 20 includes a crystal of p-type silicon; and the direction of the current path 31el (the extension direction of the extension portions) is aligned with the <110> direction. Thereby, sensing with higher sensitivity becomes possible.

In the example, for example, electrodes, etc., may be provided without providing sensing elements in the regions where the crystal orientation Dc does not match the direction connecting the fixed end (the end portion) of the film unit 20 to the opposite end.

In the sensor 210, the sensing elements are arranged along designated directions in which the sensitivity is high. The long sides of the sensing elements are aligned with the direction in which the sensitivity is high by setting the arrangement direction of the sensing elements to meander. By performing etching, etc., the configurations of the sensing elements may be patterned and may be, for example, subdivided. The current path 31el of the sensing elements may be controlled by the arrangement of the electrodes. The regions where the current path 31el is long are arranged along the direction in which the sensing sensitivity is high. Thereby, the sensitivity per unit length can be increased.

Eighth Embodiment

Figure 47:
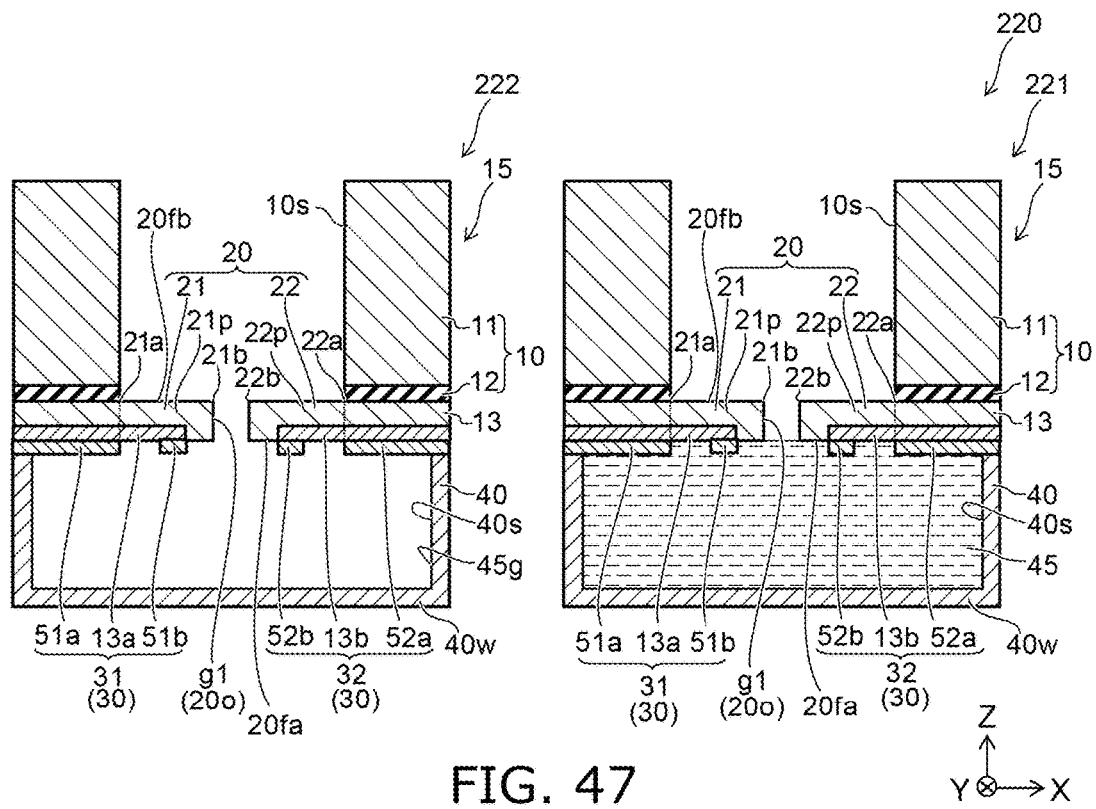
FIG. 47 is a schematic cross-sectional view showing a sensor according to an eighth embodiment.

FIG. 47 is a schematic cross-sectional view illustrating a sensor according to an eighth embodiment.

In the sensor 220 according to the embodiment as shown in FIG. 47, a set that includes the structure body 15 and the container 40 is multiply provided. There are two sets in the example. In one set (a sensor 221), the liquid 45 is disposed inside the first space 40s defined by the structure body 15 and the container 40. In the other one set (a sensor 222), the interior of the first space 40s that is defined by the structure body 15 and the container 40 is different from the interior of the first space 40s of the sensor 221. For example, a gas 45g (e.g., air) is disposed inside the first space 40s of the sensor 222. A liquid that is different from the liquid 45 may be provided in the sensor 221.

For example, the set (the sensor 222) in which the gas 45g is provided functions as a microphone. On the other hand, for example, the set (the sensor 221) in which the liquid 45 is provided functions as an acoustic sensor. For example, by sensing the difference between these sets, the desired acoustic wave can be selectively sensed. For example, by sensing the difference, noise can be suppressed (e.g., canceled). For example, a bypass filter effect is obtained. Thereby, highly-sensitive sensing becomes possible.

In the sensor 220, the reception characteristics are modified by the structure of the interior of the first space 40s. Two or more sensors having different reception characteristics are mounted in parallel; and the difference between the signals obtained by the sensors is obtained. Thereby, it becomes possible to selectively obtain the signal in the necessary band.

For example, the major band of AE in iron and steel materials is not less than 100 kHz and not more than 200 kHz. For example, the sensitivity of a first sensor is high in this band (a first band). The sensitivity of a second sensor is high in a second band that is different from the first band. Using such a combination, the difference between the signals obtained by the sensors is obtained. Thereby, the target band can be obtained selectively with high sensitivity. For example, signals the other than the target band are damped (excluded). Thereby, the noise can be suppressed.

The sensors and modifications of the sensors described in reference to the first to seventh embodiments are applicable to the configurations of the sensors used in such two sets.

Ninth Embodiment

Figure 48:
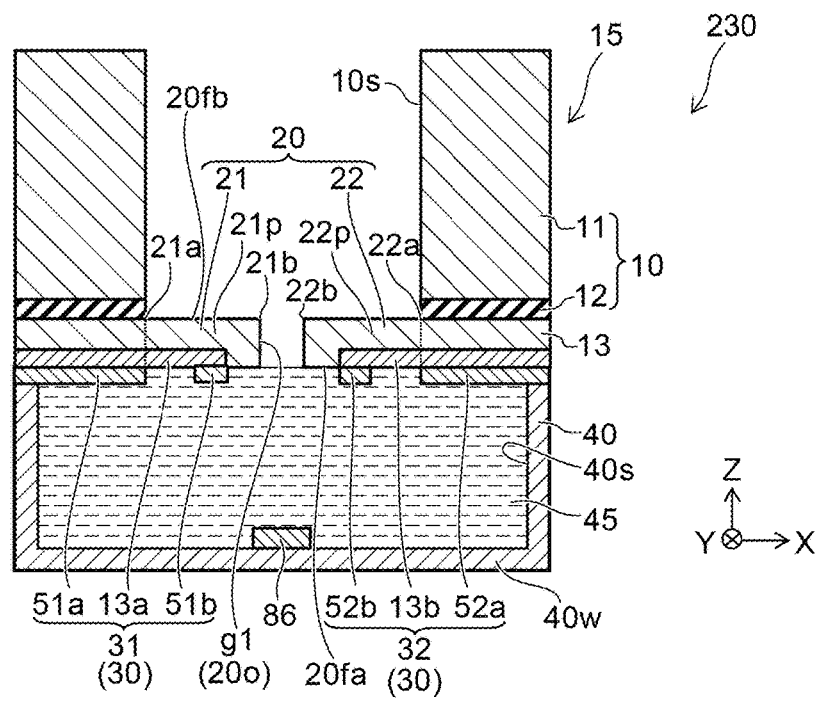
FIG. 48 is a schematic cross-sectional view showing a sensor according to a ninth embodiment.

FIG. 48 is a schematic cross-sectional view illustrating a sensor according to a ninth embodiment.

As shown in FIG. 48, the structure body 15, the container 40, and the liquid 45 are provided in the sensor 230 according to the embodiment as well. In the sensor 230, an oscillator 86 is provided in the first space 40s inside the container 40. In the example, the oscillator 86 is provided at the inner surface of the container 40. The liquid 45 is disposed between the oscillator 86 and the film unit 20.

For example, an acoustic wave is emitted from the oscillator 86. The oscillator 86 includes, for example, an electrostrictive oscillation element, a thermoacoustic oscillation element, a thermosonic oscillation element, a laser, a heater, etc. For example, for a thermoacoustic oscillation element or a thermosonic oscillation element, heat that corresponds to the period of the applied voltage is generated; and a vibration occurs in, for example, a medium such as a liquid, etc., due to the heat. The vibration is emitted as a sound wave or an ultrasonic wave.

In the sensor 230, the oscillator 86 can be used when self-testing. For example, the sensing by the sensing element of the vibration of the oscillator 86 is tested. By including the oscillator 86 used in the self-testing, the state of the sensor and/or the mounting state of the sensor can be ascertained. Sensing with high precision possible and is stable.

In the sensor 230, a device (an oscillator) for self-testing is provided to sense that the sensor 230 is operating normally. An operation test for the sensor is performed to confirm that the sensor is operating normally when using (when mounting). A transmitting device such as an oscillator, a vibrator, or the like is provided for the operation test. In the case of a reference example in which a transmitting device and a sensor (a receiving device) are provided separately, the transfer function between the transmitting device and the sensor is dependent on the mounting state. Therefore, in the reference example, a comparison with the normal transfer function is performed to confirm that the mount is normal. Conversely, because the transmitting device and the sensor are formed as one body in the sensor 230, the comparison with the normal transfer function is omitted; and the mounting state can be evaluated accurately. The cost can be reduced by forming as one body.

Tenth Embodiment

FIG. 49A to FIG. 49D are schematic views illustrating a sensor according to a tenth embodiment.

Figures 49A, 49B:
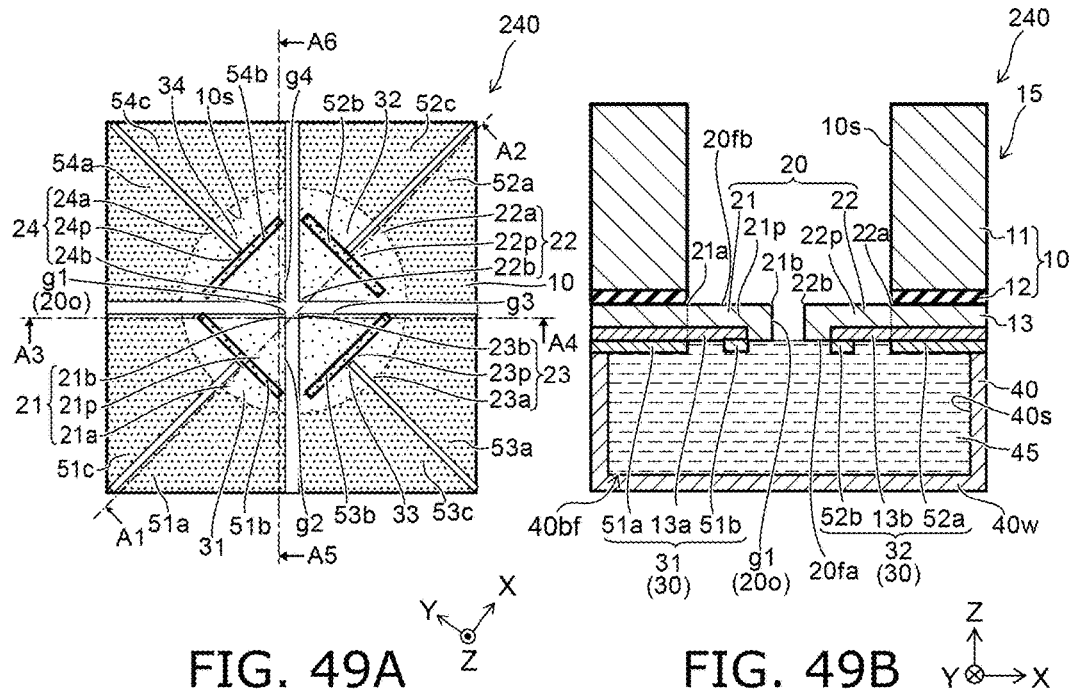
FIG. 49A to FIG. 49D are schematic views showing a sensor according to a tenth embodiment.
Figures 49C, 49D:
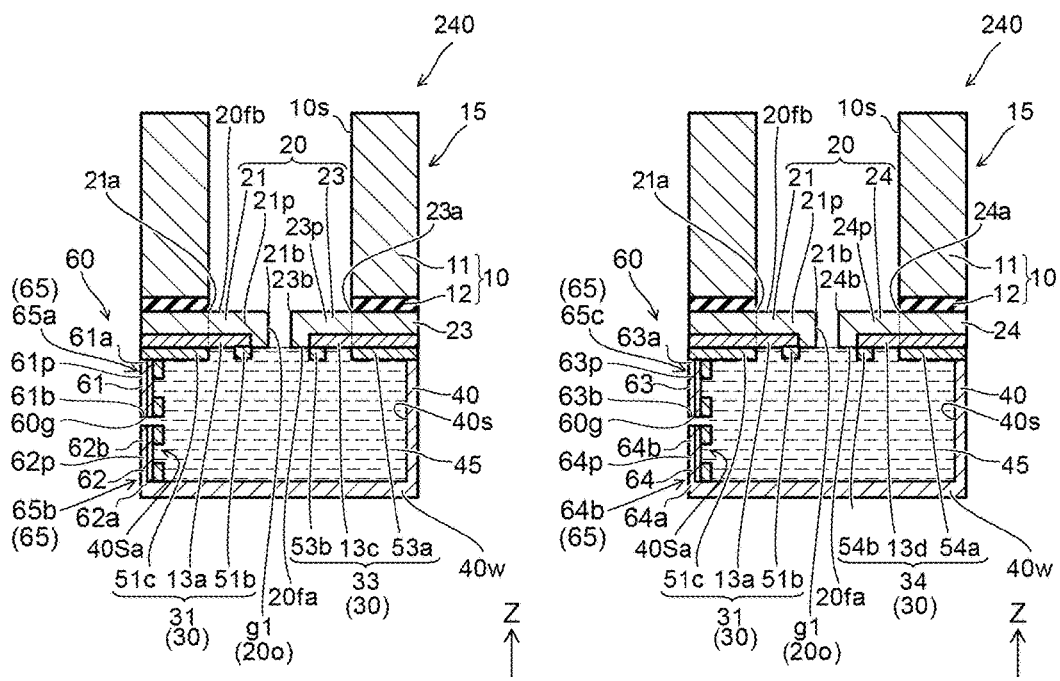

FIG. 49A is a schematic see-through plan view. FIG. 49B is a schematic cross-sectional view along line A1-A2 of FIG. 49A. FIG. 49C is a schematic cross-sectional view along line A3-A4 of FIG. 49A. FIG. 49D is a schematic cross-sectional view along line A5-A6 of FIG. 49A.

Similarly to the sensor 110, the structure body 15, the container 40, the liquid 45, and the sensing unit 30 are provided in the sensor 240 according to the embodiment. Also, the supporter 10 and the film unit 20 are provided in the structure body 15. In other words, the vibrations are sensed from the displacement of the film unit 20 opposing a bottom surface 40bf of the container 40. The first to fourth sensing elements 31 to 34 are provided respectively in the first to fourth regions 21 to 24 of the film unit 20. The first to fourth sensing elements 31 to 34 respectively include the crystal layers 13a to 13d. These sensing elements are provided on the liquid 45 on the bottom surface 40bf of the container 40.

In the sensor 240, other film units (side surface film units 60) are provided at the side surfaces (a first side surface 40sa and a second side surface 40sb) of the container 40. Also, other sensing units (side surface sensing units 65) that sense the deformation of the side surface film units 60 are provided.

For example, the first side surface 40sa of the container 40 intersects the second side surface 40sb of the container. The side surface film unit 60 is provided at each of the two intersecting side surfaces. Based on the vibration applied from the outside, the liquid 45 vibrates; and the side surface film units 60 are displaced (deform). These displacements of the side surface film units 60 are sensed by the side surface sensing units 65. Thereby, vibrations in three directions can be sensed. Thereby, sensing with even higher precision becomes possible.

A region 61 and a region 62 of the side surface film unit 60 are provided at the first side surface 40sa. The region 61 includes an end portion 61a and an opposite end 61b. One portion 61p of the region 61 is displaceable. The region 62 includes an end portion 62*a* and an opposite end 62*b*. One portion 62*p* of the region 62 is displaceable.

A region 63 and a region 64 of the side surface film unit 60 are provided at the second side surface 40*sb*. The region 63 includes an end portion 63*a* and an opposite end 63*b*. One portion 63*p* of the region 63 is displaceable. The region 64 includes an end portion 64*a* and an opposite end 64*b*. One portion 64*p* of the region 64 is displaceable.

These displacements of the one portions 61*p* to 64*p* of the side surface film unit 60 are sensed respectively by sensing elements 65*a* to 65*d* of the side surface sensing unit 65.

Eleventh Embodiment

Figure 50:
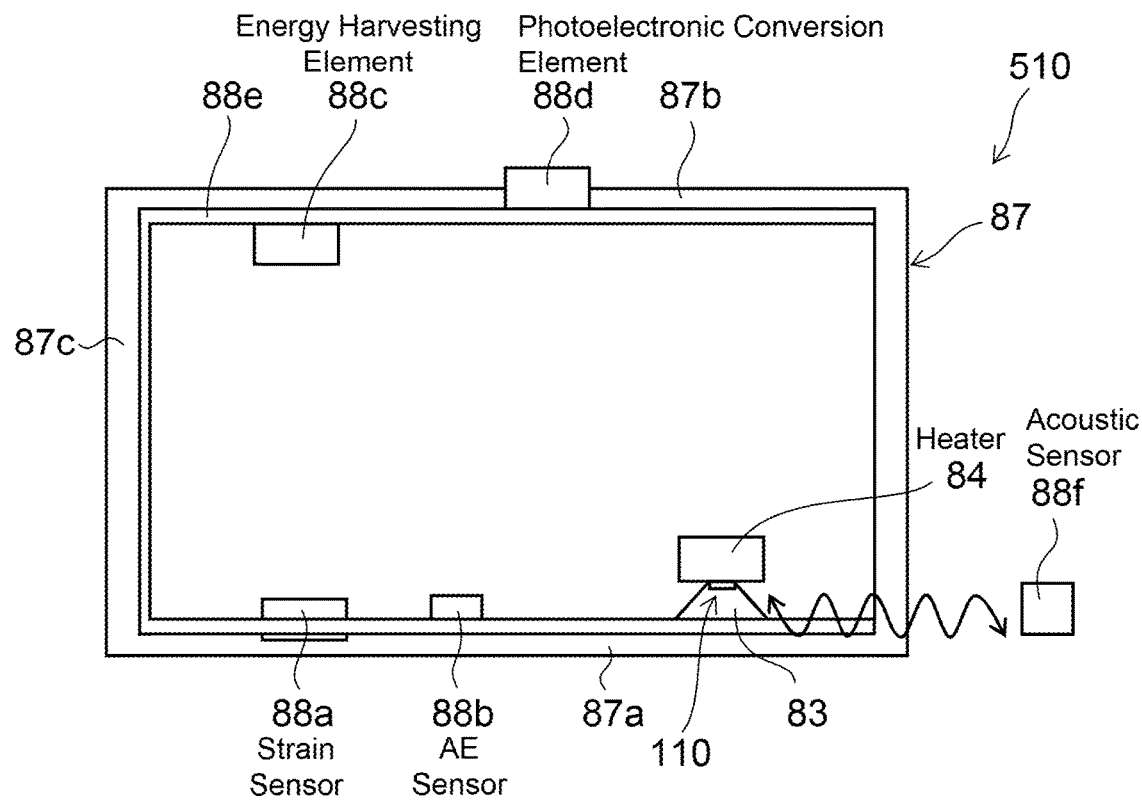
FIG. 50 is a schematic cross-sectional view showing a sensor unit according to an eleventh embodiment.

FIG. 50 is a schematic cross-sectional view illustrating a sensor unit according to an eleventh embodiment.

As shown in FIG. 50, a housing 87 is provided in a sensor unit 510 according to the embodiment. The housing 87 includes, for example, a bottom surface portion 87*a*, an opposing portion 87*b*, and a side surface portion 87*c*. The opposing portion 87*b* opposes the bottom surface portion 87*a*. The side surface portion 87*c* connects the bottom surface portion 87*a* to the opposing portion 87*b*.

In the example, any sensor and modifications of any sensor according to the embodiment recited above is provided at the bottom surface portion 87*a*. In the example, the sensor 110 is provided at the bottom surface portion 87*a*. In the example, a sound collector 83 is provided at the bottom surface portion 87*a*. The sound collector 83 has an acoustic lens effect. The sensor 110 is provided on the sound collector 83.

In the example, a heater 84 is further provided on the sensor 110. The heater 84 controls the temperature of the sensor 110. For example, the heater 84 is used in the calibration.

In the example, a strain sensor 88*a* and an AE sensor 88*b* are further provided in the bottom surface portion 87*a*. The strain sensor 88*a* is, for example, a strain gauge. For example, the AE sensor 88*b* is used when ascertaining the mounting state. The sensor 110, the strain sensor 88*a*, and the AE sensor 88*b* are provided on the inner side of the housing 87.

In the example, a photoelectric conversion element 88*d* is provided at the opposing portion 87*b*. The photoelectric conversion element 88*d* includes, for example, a solar cell (a photovoltaic power generation element), etc. Further, an energy harvesting element 88*c* may be provided at the opposing portion 87*b*. The energy harvesting element 88*c* includes, for example, a vibrational power generation element, etc.

An interconnect layer 88*e* is provided at the opposing portion 87*b*, the side surface portion 87*c*, and the bottom surface portion 87*a*. For example, the sensor 110 is connected to at least one of the photoelectric conversion element 88*d* or the energy harvesting element 88*c*. The strain sensor 88*a* and the AE sensor 88*b* are further connected.

In the example, an acoustic sensor 88*f* is disposed outside the housing 87. For example, the acoustic sensor 88*f* is used when ascertaining the mounting state.

Thus, in the sensor unit 510, multiple sensors that include the sensor 110 are mounted to the housing 87 as a composite sensor. In other words, the sensor 110, the strain sensor 88*a*, and the AE sensor 88*b* are mounted inside one package. The sensor 110 is provided at the bottom surface portion 87*a*. The bottom surface portion 87*a* is on the bonding side of the package. AE is conducted from the bottom surface portion 87*a* to the sensor 110. The sound collector 83 is provided on the inner surface of the bottom surface portion 87*a*. By disposing the sensor 110 on the sound collector 83, AE can be acquired efficiently inside the composite package.

A plate may be provided between the strain sensor 88*a* and the bottom surface portion 87*a* of the housing 87. The plate may include, for example, stainless steel, etc. The thickness of the plate is, for example, not less than 0.2 mm and not more than 0.3 mm. By providing the plate, the environmental resistance improves and the acquisition efficiency of the strain sensing increases for the strain sensor 88*a*.

The sensor unit 510 is used for continuous monitoring. A self-supporting power supply of a solar panel, etc., is formed integrally. Thereby, for example, the electrical power loss due to power transmission is low; and the electrical power decreases.

A preamplifier of the sensor 110, etc., may be built into the interior of the sensor unit 510. The distance between the sensor 110 and the preamplifier can be short. For example, the noise can be reduced. By including the preamplifier, monitoring by long-distance cable transmission becomes possible. The external power supply can be omitted.

Figure 51:
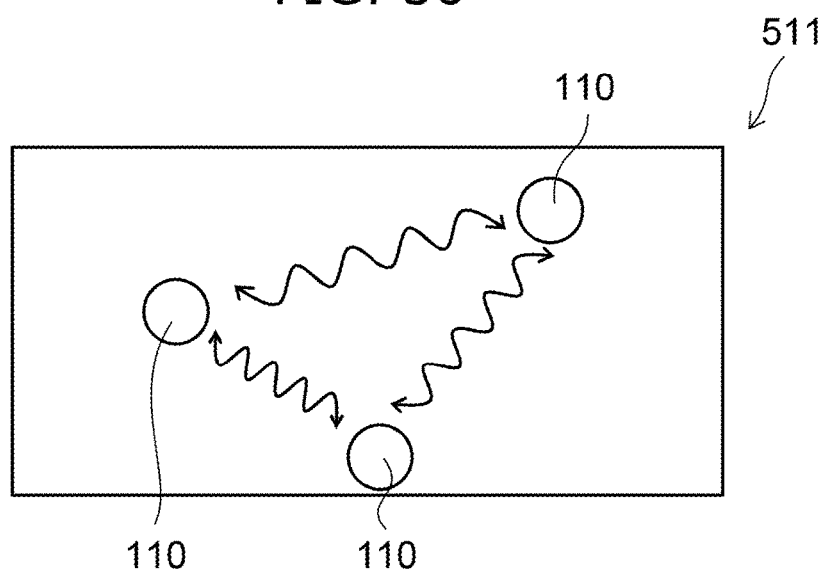
FIG. 51 is a schematic cross-sectional view showing another sensor unit according to the eleventh embodiment.

FIG. 51 is a schematic cross-sectional view illustrating another sensor unit according to the eleventh embodiment.

As shown in FIG. 51, three sensors 110 are provided in a sensor unit 511 according to the embodiment. By providing three or more sensors 110 in one sensor unit 511, the mounting state of the multiple sensors can be ascertained. In the example, any sensor according to the embodiment recited above may be used.

Figure 52:
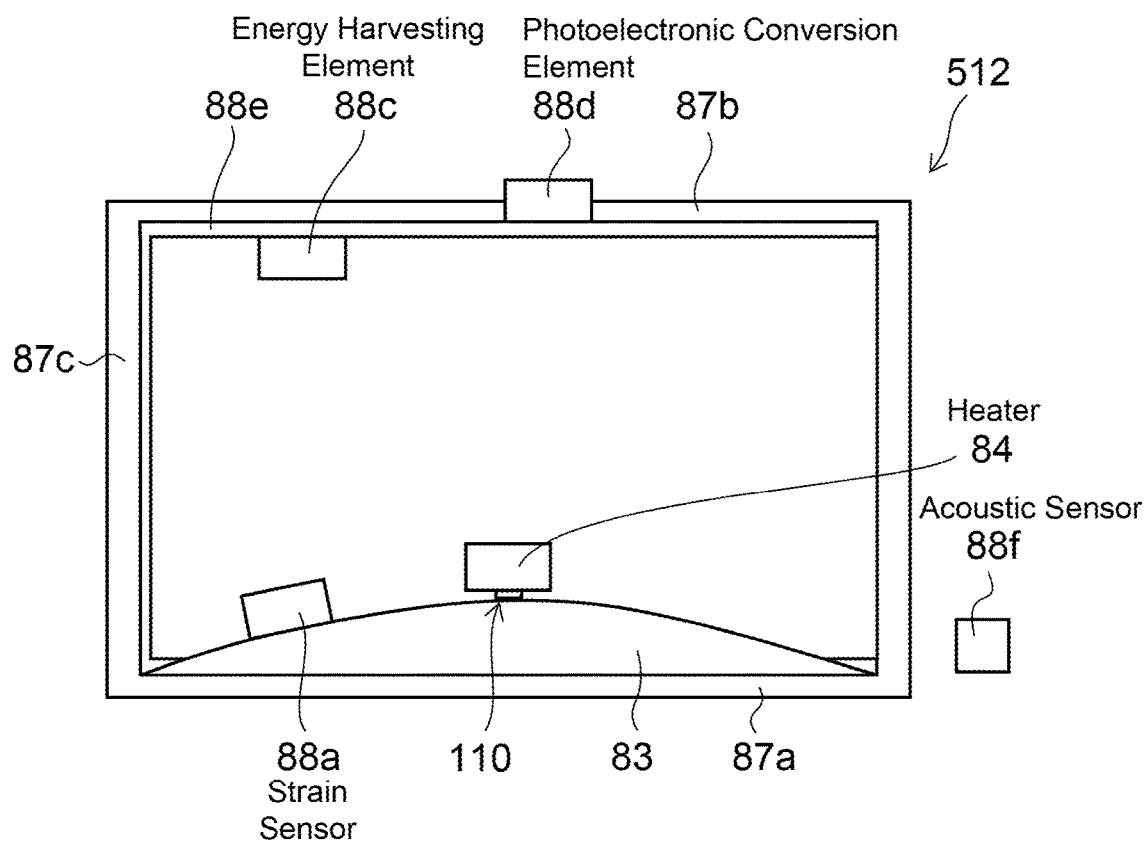
FIG. 52 is a schematic cross-sectional view showing another sensor unit according to the eleventh embodiment.

FIG. 52 is a schematic cross-sectional view illustrating another sensor unit according to the eleventh embodiment.

In the sensor unit 512 according to the embodiment, the bottom surface portion 87*a* of the housing 87 has an acoustic lens structure. AE collects at the central portion of the bottom surface portion 87*a*. The sensor 110 is disposed on the central portion of the bottom surface portion 87*a*. For example, a sound collection structure is formed on the entire bottom surface portion 87*a*. The AE that is conducted from the bottom surface portion 87*a* side concentrates in the sensor 110. More vibration energy can be obtained; and higher sensitivity is obtained.

According to the embodiments, a highly-sensitive sensor and sensor unit can be provided.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as structure bodies, supporters, film units, side surface film units, containers, liquids, and sensing units, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors practicable by an appropriate design modification by one skilled in the art based on the sensors described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention. The above embodiments can be practiced in combination with each other.

What is claimed is:

1. A sensor, comprising:
   a structure body including a supporter, and
   a film unit including a first region and an opening, the first region including a first end portion and a first portion, the first end portion being supported by the supporter, the first portion being displaceable;
   a container connected to the structure body, a liquid being provided between the film unit and the container; and
   a sensing unit sensing a first portion displacement accompanying a liquid displacement.

2. The sensor according to claim 1, wherein the liquid displacement occurs based on a sound wave applied to the container.

3. The sensor according to claim 1, wherein
   the film unit further includes a second region, the second region including a second end portion and
   a second portion, the second end portion being supported by the supporter, and a first gap used as the opening is provided between the first portion and the second portion.

4. The sensor according to claim 3, wherein
   the second portion is displaceable,
   the film unit includes:
      a third region including a third end portion and a third portion, the third end portion being supported by the supporter, the third portion being displaceable; and
      a fourth region including a fourth end portion and a fourth portion, the fourth end portion being supported by the supporter, the fourth portion being displaceable,
   a second gap is provided between the first portion and the third portion,
   a third gap is provided between the second portion and the third portion,
   a fourth gap is provided between the second portion and the fourth portion, and
   the sensing unit further senses:
      a second portion displacement accompanying the liquid displacement;
      a third portion displacement accompanying the liquid displacement; and
      a fourth portion displacement accompanying the liquid displacement.

5. The sensor according to claim 1, wherein
   the supporter defines a space, and
   at least one portion of the first portion is disposed between the space and the liquid.

6. The sensor according to claim 1, wherein
   the sensing unit includes a first sensing element provided at the first portion, and
   the first sensing element has at least one of:
      a change of a resistance occurring with the first portion displacement;
      a change of a voltage of piezoelectricity occurring with the first portion displacement; or
      a change of an electrostatic capacitance occurring with the first portion displacement.

7. The sensor according to claim 6, wherein
   the first sensing element includes:
      a crystal layer of silicon including an impurity;
      a first electrode connected to one portion of the crystal layer; and
      a second electrode connected to one other portion of the crystal layer,
   the liquid displacement includes a surface wave including a first wavelength, and
   a distance between the first electrode and the second electrode is not less than 0.4 times and not more than 0.6 times the first wavelength or not less than 0.22 times and not more than 0.28 times the first wavelength.

8. The sensor according to claim 1, wherein
   the sensing unit includes a first sensing element provided at the first portion, and
   the first sensing element has a change of a resistance accompanying the first portion displacement.

9. The sensor according to claim 8, wherein
   the first sensing element includes:
      a crystal layer of silicon including an impurity;
      a first electrode connected to one portion of the crystal layer; and
      a second electrode connected to one other portion of the crystal layer, and
   a direction from the first electrode toward the second electrode is aligned with one direction of the <110> direction or the <100> direction of the crystal layer.

10. The sensor according to claim 1, wherein
    the liquid has a first liquid surface and a second liquid surface, the first liquid surface being on the film unit side, the second liquid surface being on a side opposite to the first liquid surface, and
    the second liquid surface includes a portion tilted with respect to a plane, the plane being perpendicular to a first direction from the container toward the supporter.

11. The sensor according to claim 10, wherein
    the film unit further includes a second region including a second end portion supported by the supporter,
    the second liquid surface has a first front surface and a second front surface, the first front surface being on a side of the first end portion, the second front surface being on a side of the second end portion, and
    a tilt direction with respect to the plane of the first front surface is reverse to a tilt direction with respect to the plane of the second front surface.

12. The sensor according to claim 1, wherein a natural frequency of the liquid is not less than 0.8 times and not more than 1.2 times an integer multiple of 1 or more times a natural frequency of the container.

13. The sensor according to claim 1, wherein
    the first region includes a first opposite end on a side opposite to the first end portion,
    the sensing unit includes a first sensing element disposed at a first position inside the first portion, and
    a distance between the first end portion and the first position is shorter than a distance between the first opposite end and the first position.

14. The sensor according to claim 1, wherein a length of the first region along an extension direction is shorter than a length perpendicular to a first direction and perpendicular to the extension direction, the extension direction being from the first end portion toward the first portion, the first direction being from the container toward the supporter.

15. The sensor according to claim 14, wherein
the sensing unit includes a second sensing element and a first sensing element provided at the first portion, and
a direction from the first sensing element toward the second sensing element intersects the extension direction.

16. The sensor according to claim 1, wherein the opening is positioned at a central portion of the film unit.

17. The sensor according to claim 1, wherein
the film unit includes a central portion and a peripheral portion, the peripheral portion being around the central portion, and
the opening is positioned at the peripheral portion.

18. The sensor according to claim 1, wherein the film unit has a gammadion cross configuration.

19. The sensor according to claim 1, wherein
the sensing unit includes:
    a first sensing element provided at a first position of the first portion; and
    a second sensing element provided at a second position of the first portion, the first region includes a first opposite end on a side opposite to the first end portion, and
a direction from the first position toward the second position is aligned with a direction from the first end portion toward the first opposite end.

20. The sensor according to claim 1, wherein
the film unit has a first surface and a second surface, the first surface being on a side of the liquid, the second surface being on a side opposite to the first surface,
the sensing unit includes:
    a first sensing element provided at the first surface of the first portion; and
    a second sensing element provided at the second surface of the first portion, and
at least one of the first sensing element or the second sensing element has at least one of:
    a change of a resistance accompanying the first portion displacement;
    a change of an electrostatic capacitance accompanying the first portion displacement; or
    a change of a voltage of piezoelectricity accompanying the first portion displacement.

* * * * *